(12) United States Patent
Zhu

(10) Patent No.: US 8,070,682 B2
(45) Date of Patent: Dec. 6, 2011

(54) METHOD AND APPARATUS FOR MEDICAL IMAGING USING COMBINED NEAR-INFRARED OPTICAL TOMOGRAPHY, FLUORESCENT TOMOGRAPHY AND ULTRASOUND

(75) Inventor: Quing Zhu, Mansfield Center, CT (US)

(73) Assignee: The University of Connecticut, Farmington, CT (US)

( * ) Notice: Subject to any disclaimer, the term of this patent is extended or adjusted under 35 U.S.C. 154(b) by 1095 days.

(21) Appl. No.: 11/780,200

(22) Filed: Jul. 19, 2007

(65) Prior Publication Data
US 2010/0256496 A1 Oct. 7, 2010

Related U.S. Application Data

(60) Provisional application No. 60/832,002, filed on Jul. 19, 2006.

(51) Int. Cl.
*A61B 8/00* (2006.01)

(52) U.S. Cl. ........ 600/437; 600/438; 600/443; 600/447; 600/448; 600/459; 600/473; 600/476

(58) Field of Classification Search .................. 600/407, 600/437, 439, 443, 459, 473
See application file for complete search history.

(56) References Cited

U.S. PATENT DOCUMENTS

| | | | | |
|---|---|---|---|---|
| 5,818,583 A | * | 10/1998 | Sevick-Muraca et al. | 356/336 |
| 6,016,439 A | * | 1/2000 | Acker | 600/411 |
| 6,138,045 A | | 10/2000 | Kupinski et al. | |
| 6,185,320 B1 | | 2/2001 | Bick et al. | |
| 6,264,610 B1 | * | 7/2001 | Zhu | 600/443 |
| 6,524,254 B2 | * | 2/2003 | Erikson | 600/447 |
| 6,615,063 B1 | | 9/2003 | Ntziachristos et al. | |
| 6,690,958 B1 | * | 2/2004 | Walker et al. | 600/323 |
| 6,752,763 B2 | * | 6/2004 | Erikson | 600/459 |
| 7,179,449 B2 | * | 2/2007 | Lanza et al. | 424/9.321 |
| 7,349,731 B2 | * | 3/2008 | Jiang | 600/473 |
| 2004/0215072 A1 | * | 10/2004 | Zhu | 600/407 |
| 2004/0220465 A1 | * | 11/2004 | Cafarella | 600/407 |
| 2010/0129410 A1 | * | 5/2010 | Eisenbach et al. | 424/277.1 |

FOREIGN PATENT DOCUMENTS
WO   WO 03000137   1/2003
(Continued)

OTHER PUBLICATIONS

Huang et al., "Dual-mesh optical tomography reconstruction method with a depth correction that uses a prior ultrasound information", Applied Optics, vol. 43, No. 8, pp. 1654-1662, Mar. 10, 2004.

(Continued)

*Primary Examiner* — Tse Chen
*Assistant Examiner* — Baisakhi Roy
(74) *Attorney, Agent, or Firm* — Cantor Colburn LLP

(57) ABSTRACT

Methods and apparatus for medical imaging using diffusive optical tomography and fluorescent diffusive optical tomography and ultrasound are disclosed. In one embodiment, the probe comprises emitters and detectors that are inclined at an angle of about 1 to about 30 degrees to a surface of the probe that contacts tissue. In another embodiment, the scanned volume is divided into an inclusion region and a background region. Different voxel sizes are used in the inclusion region and the background region. Appropriate algorithms facilitate a reconstruction of the inclusion region to determine structural and functional features of the inclusion.

14 Claims, 59 Drawing Sheets

FOREIGN PATENT DOCUMENTS

| | | |
|---|---|---|
| WO | WO 03077744 | 9/2003 |
| WO | WO 03055383 | 10/2003 |

OTHER PUBLICATIONS

Q. Zhu et al., "Imager that combines near-infrared diffusive light and ultrasound", Optics Letters, vol. 24, No. 15, pp. 1050-1052 Aug. 1, 1999.

Danen et al., "Regional Imager for Low-Resolution Functional Imaging of the Brain with Diffusing Near-Infrared Light", Photochemistry and Photobiology, 1998, 67(1): pp. 33-40.

Zhu et al., Imaging tumor angiogenesis by use of combined near-infrared diffusive light and ultrasound, Optics letters, vol. 28 No. 5, pp. 337-339 Mar. 1, 2003.

Chen et al., "Simultaneous near-infrared diffusive light and ultrasound imaging", Applied Optics, vol. 40 No. 34 pp. 6367-6380 Dec. 1, 2001.

Ebers et al., "Thermal Stability of Polyester-Styrene Resin Systems", Industrial and Engineering Chemistry, vol. 42, No. 1, pp. 114-119 Jan. 1950.

Zhu et al. "Ultrasound-Guided Optical Tomographic Imaging of Malignant and Benign Breast Lesions: Initial Clinical Results of 19 Cases" Neoplasia vol. 5 No. 5, pp. 1-11 Jul. 18, 2003.

Yuan et al., "Separately reconstructing the structural and functional parameters of a fluorescent inclusion embedded in a turbid medium" Optics Express vol. 14, No. 16 Aug. 1, 2006.

A. H. Hielscher, et al., Image Reconstruction Schemes for Optical Tomography; Engineering in Medicine and Biology Society (1998); 20th Annual International Conference of the IEEE Hong Kong, China on Oct. 29-Nov. 1, 1998 Piscataway, NJ USA. pp. 876-879, vol. 2; XP010320534; ISBN: 0-7803-5164-9.

M. Huang, et al., 2-D NIR Imaging Reconstruction with Ultrasound Guidance, Biomedical Imaging (2002); IEEE International Symposium on Jul. 7-10, 2002, Piscataway, NJ USA. pp. 1031-1034; XP010600770; ISBN: 0-7803-7584-X.

D.N. Ivanov, Iterative Reconstruction Algorithms in Optical Tomography in Frequency Domain Case; Science and Technology (2005), KORUS (2005); The Ninth Russian-Korean International Symposium on Novosibirsk, Russia on Jun. 26-Jul. 2, 2005, Piscataway, NJ, USA. pp. 163-166; XP010836966; ISBN:0-7803-8943-3.

H. Dehghani, et al., Image Reconstruction Strategies Using Dual Modality MRI-NIR Data; Biomedical Imaging: Macro to Nano (2006) IEEE International Symposium on Apr. 6, 2006, Piscataway, NJ, USA. pp. 682-685; XP010912722; ISBN: 0-7803-9576-X.

International Search Report dated Mar. 7, 2008 for App. #PCT/US2007/016390.

* cited by examiner

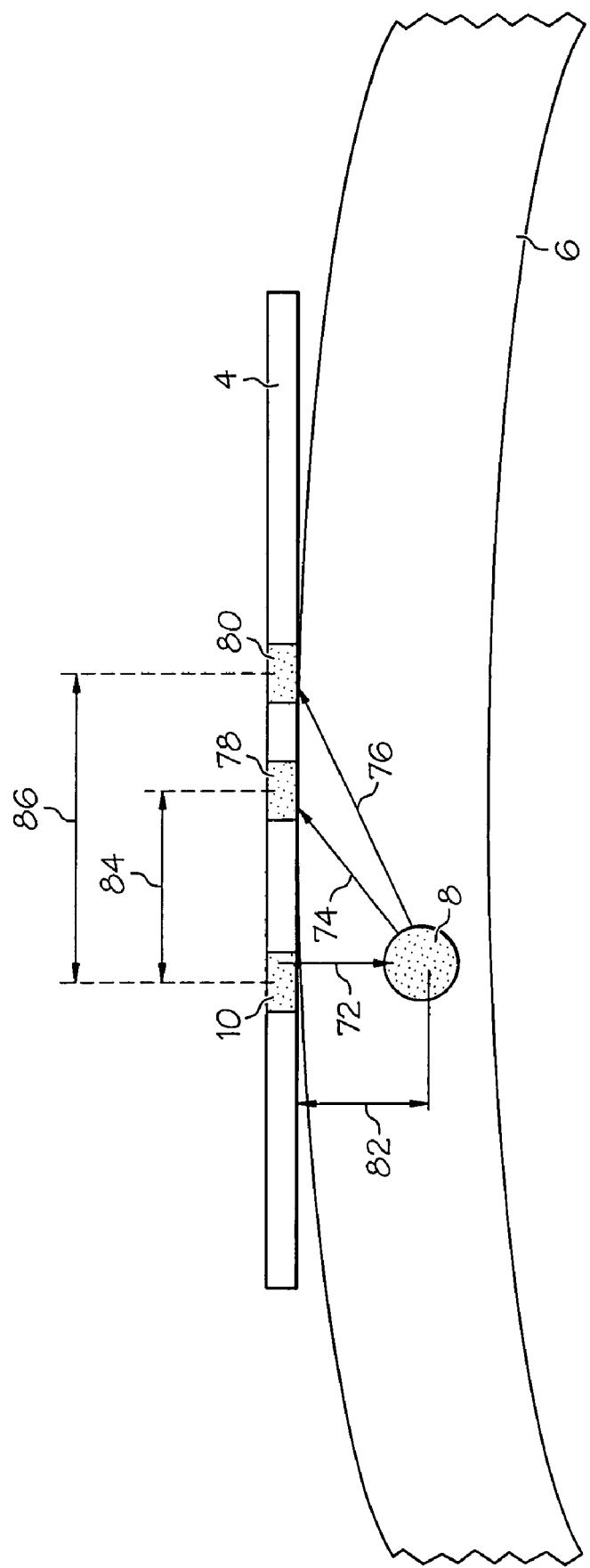

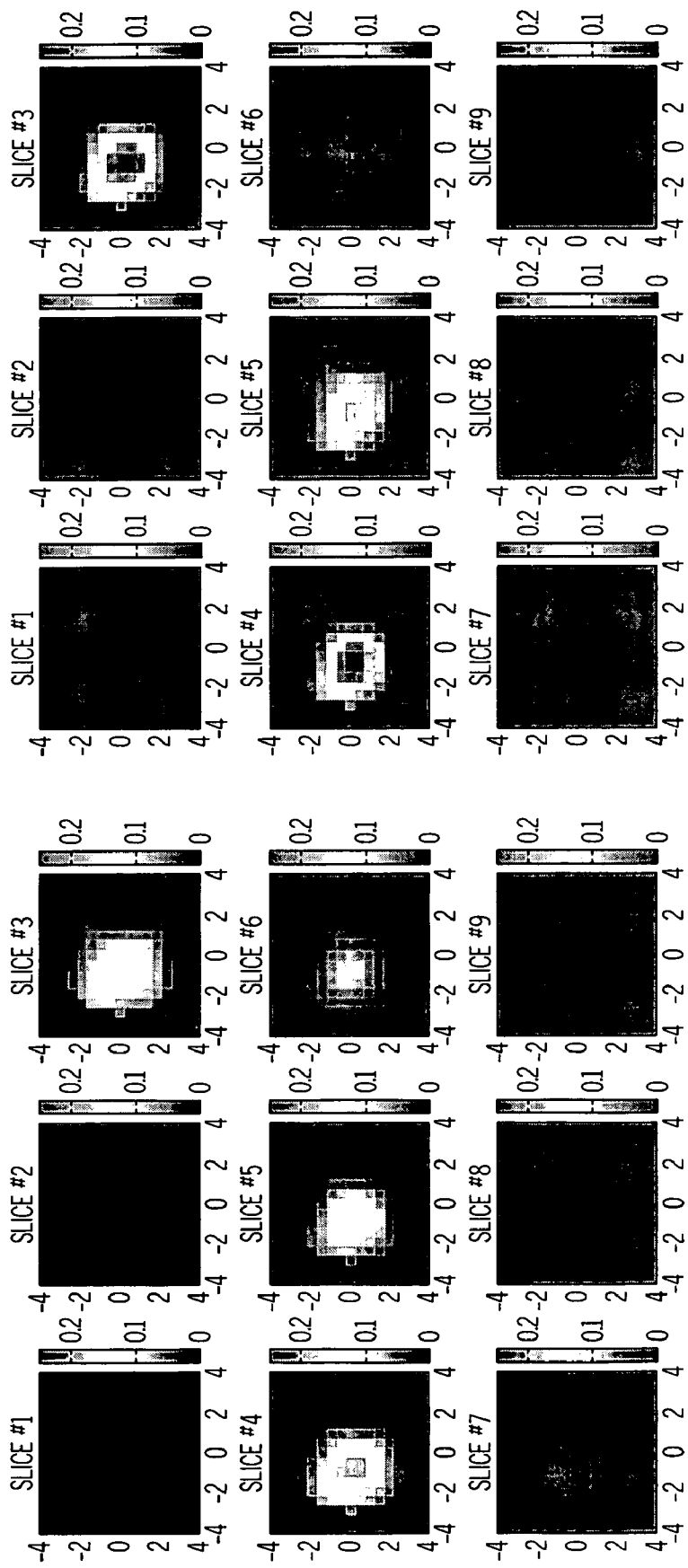
FIG. 13H  350Mhz, 780nm
FIG. 13G  140Mhz, 780nm

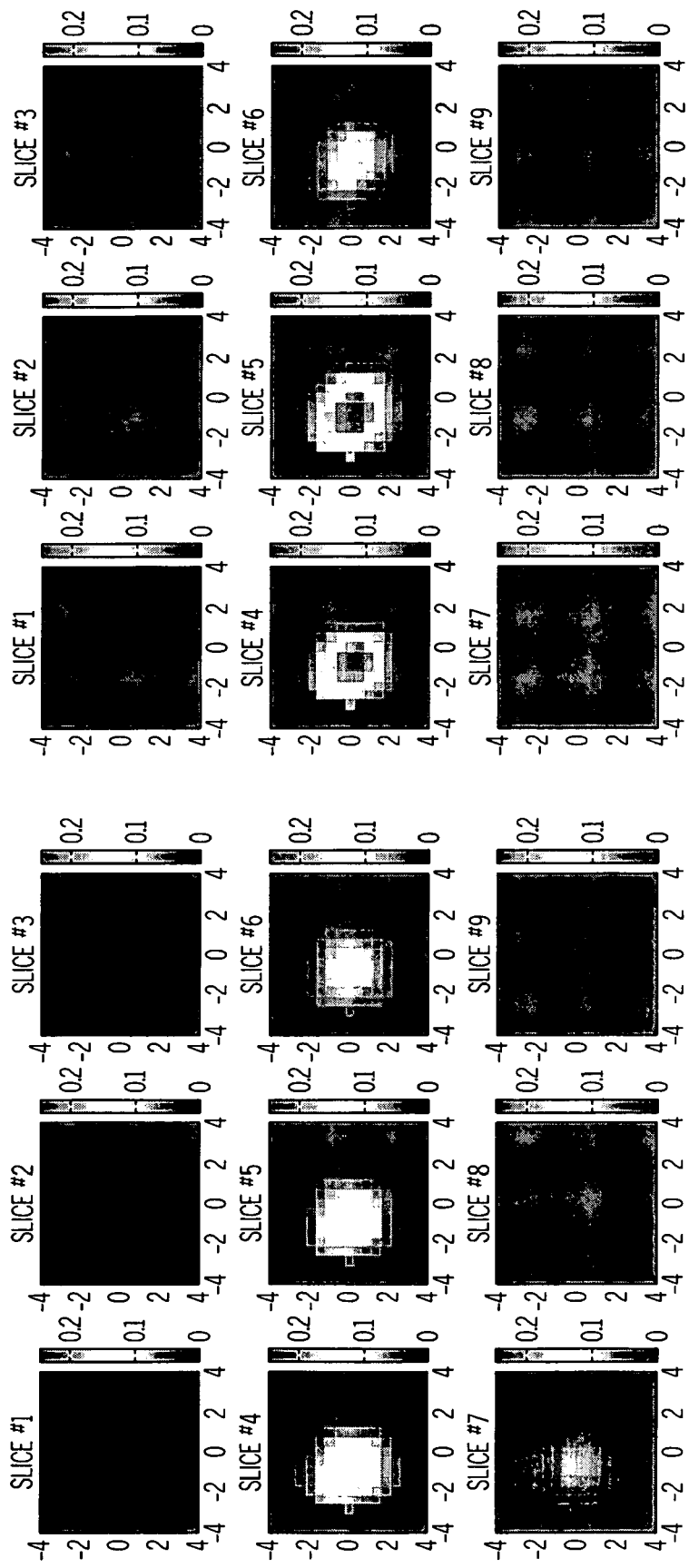
FIG. 13L (350Mhz, 780nm)
FIG. 13K (140Mhz, 780nm)

50Mhz, 780nm

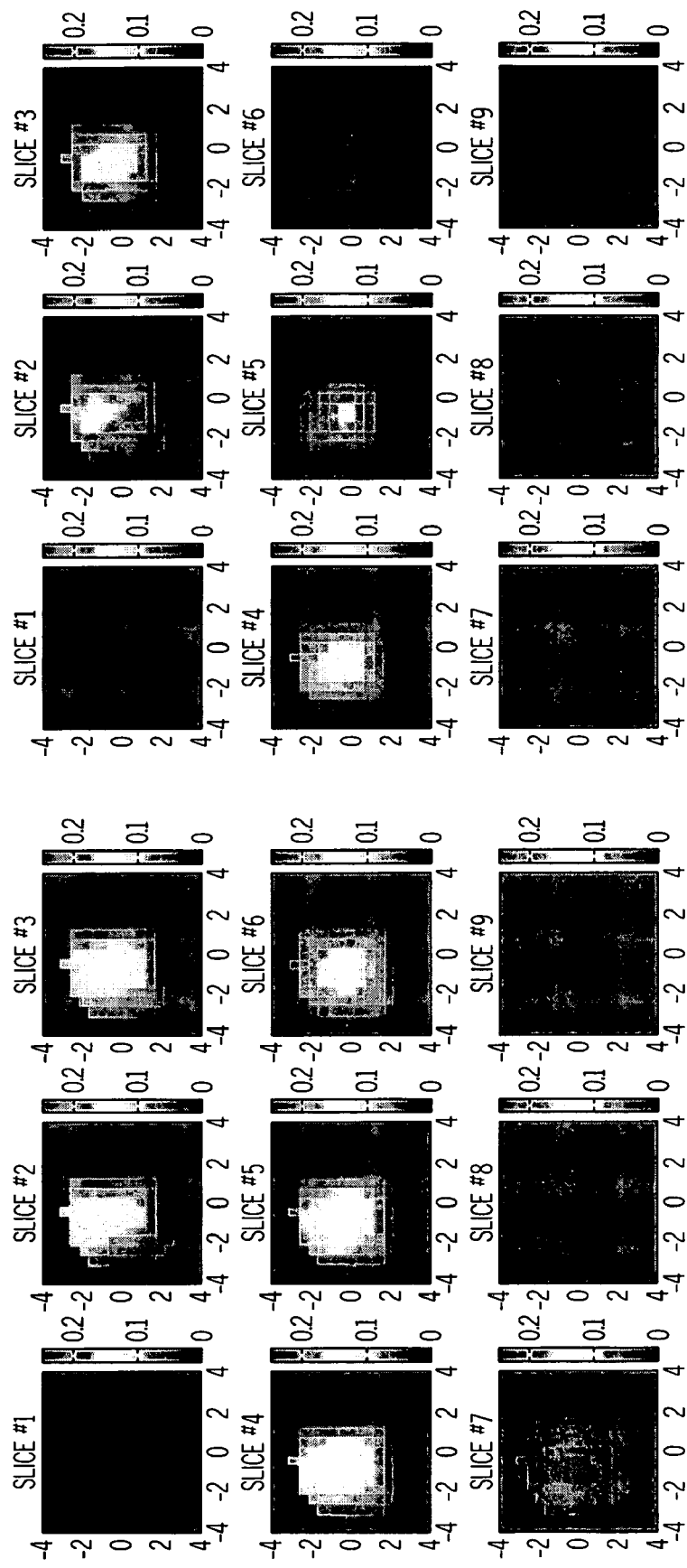
FIG. 14B 140Mhz, 780nm
FIG. 14A 50Mhz, 780nm

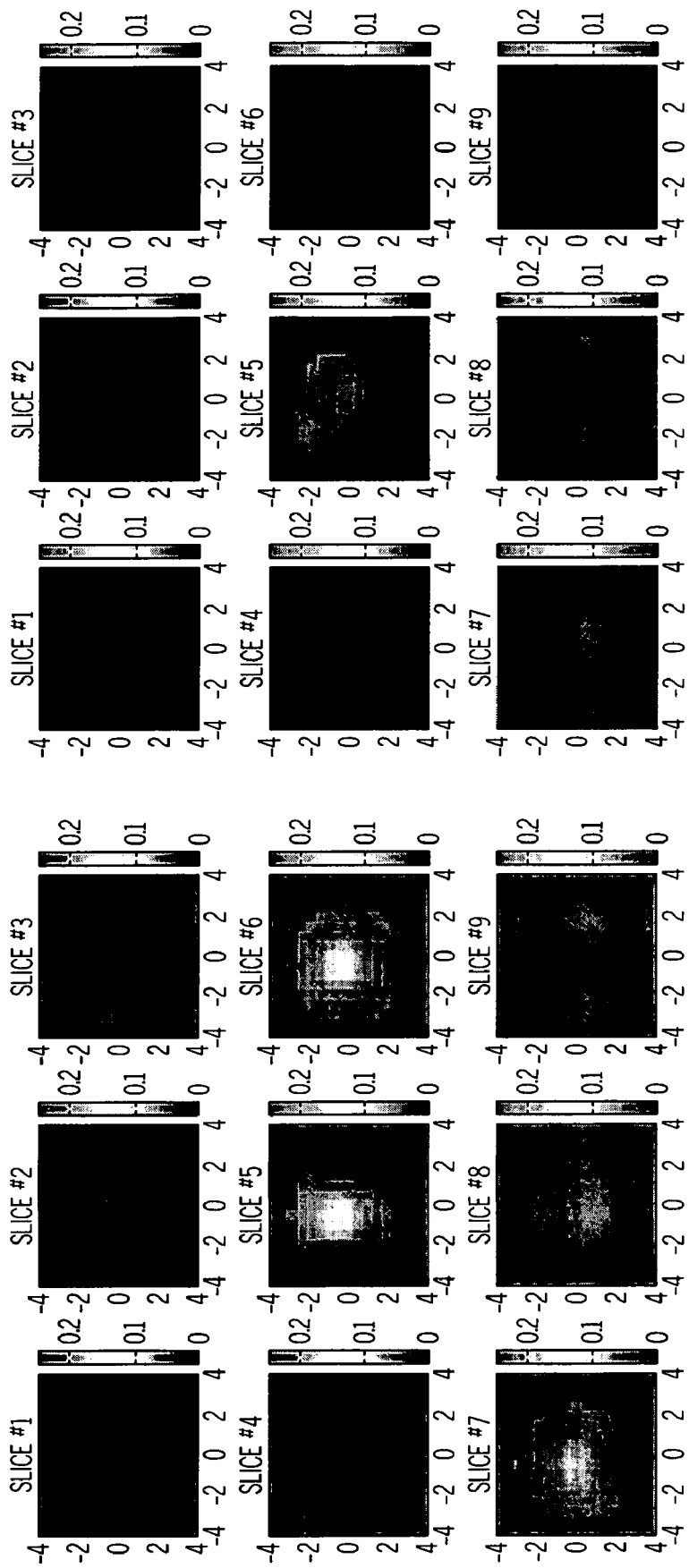

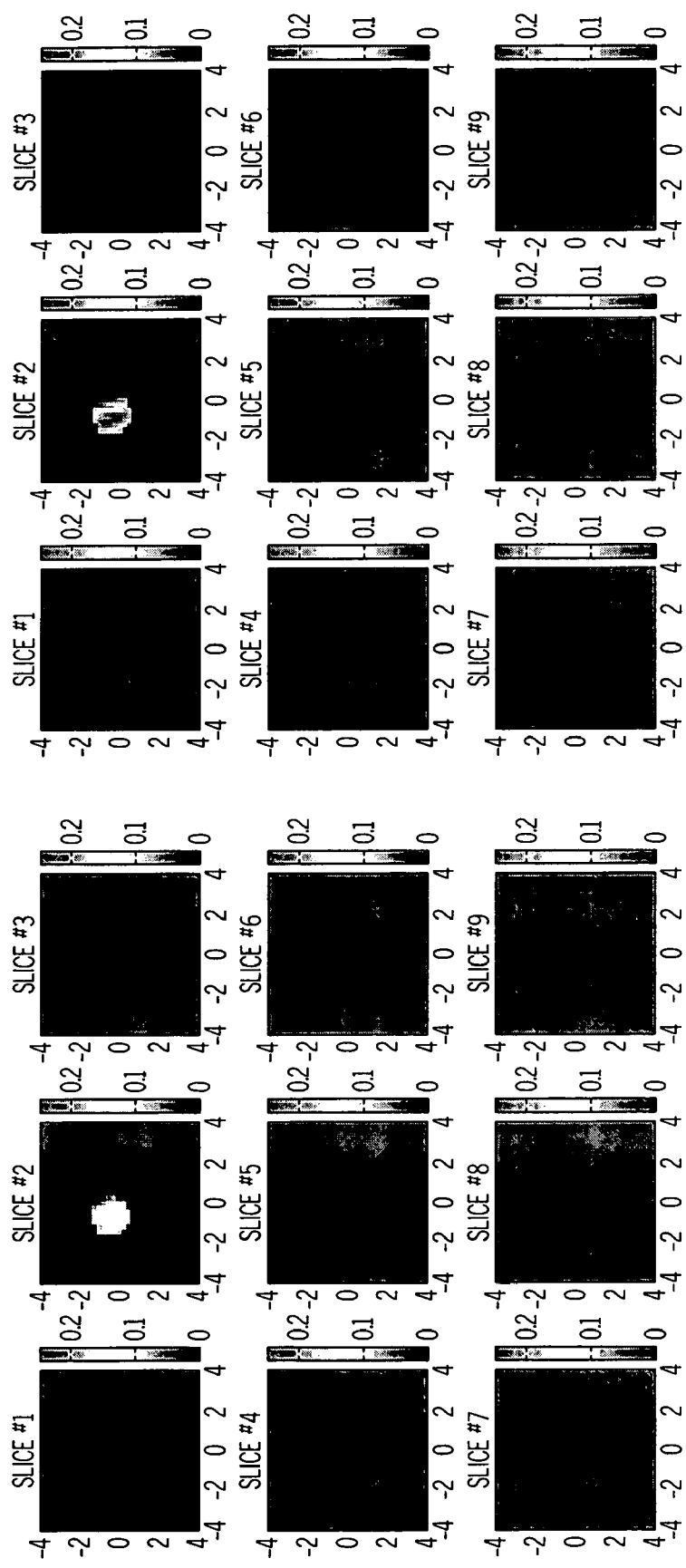
FIG. 15D  350Mhz, 780nm
FIG. 15C  140Mhz, 780nm

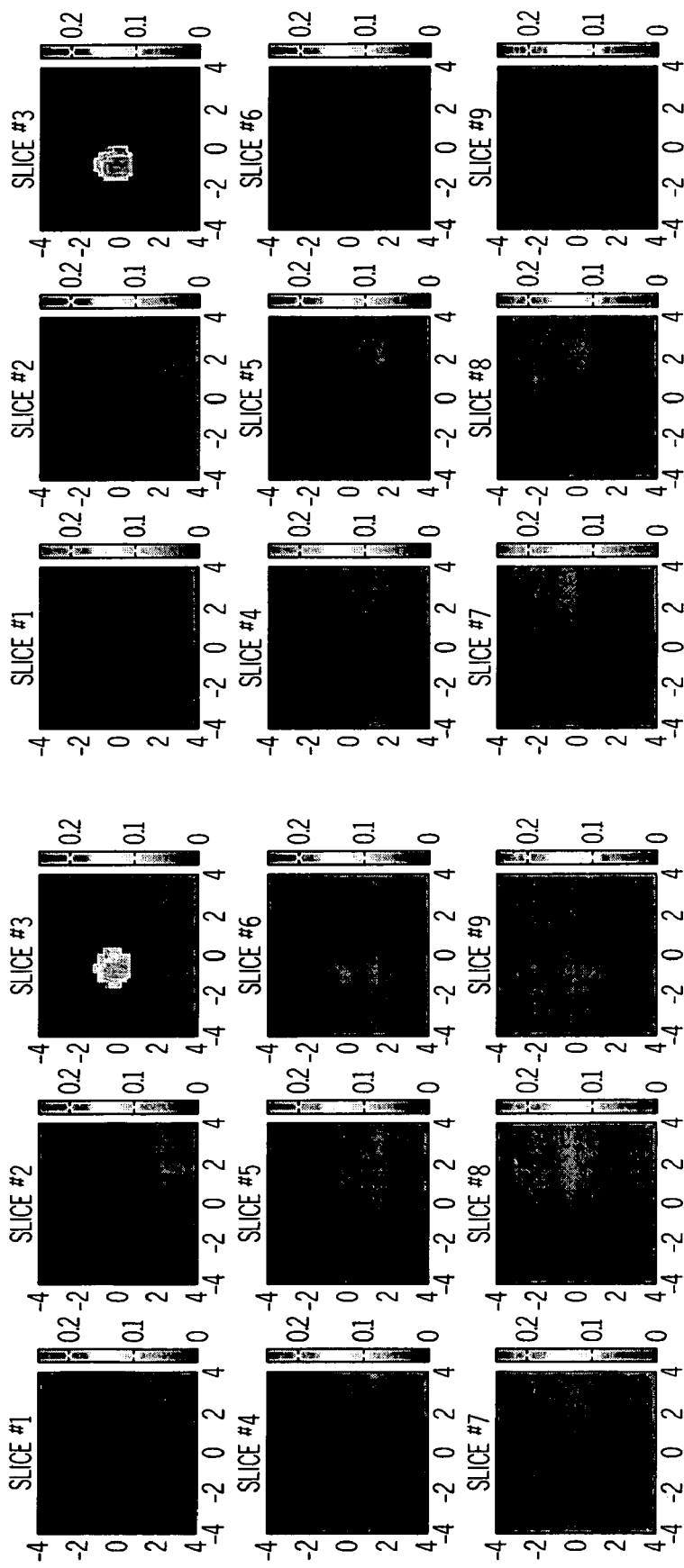

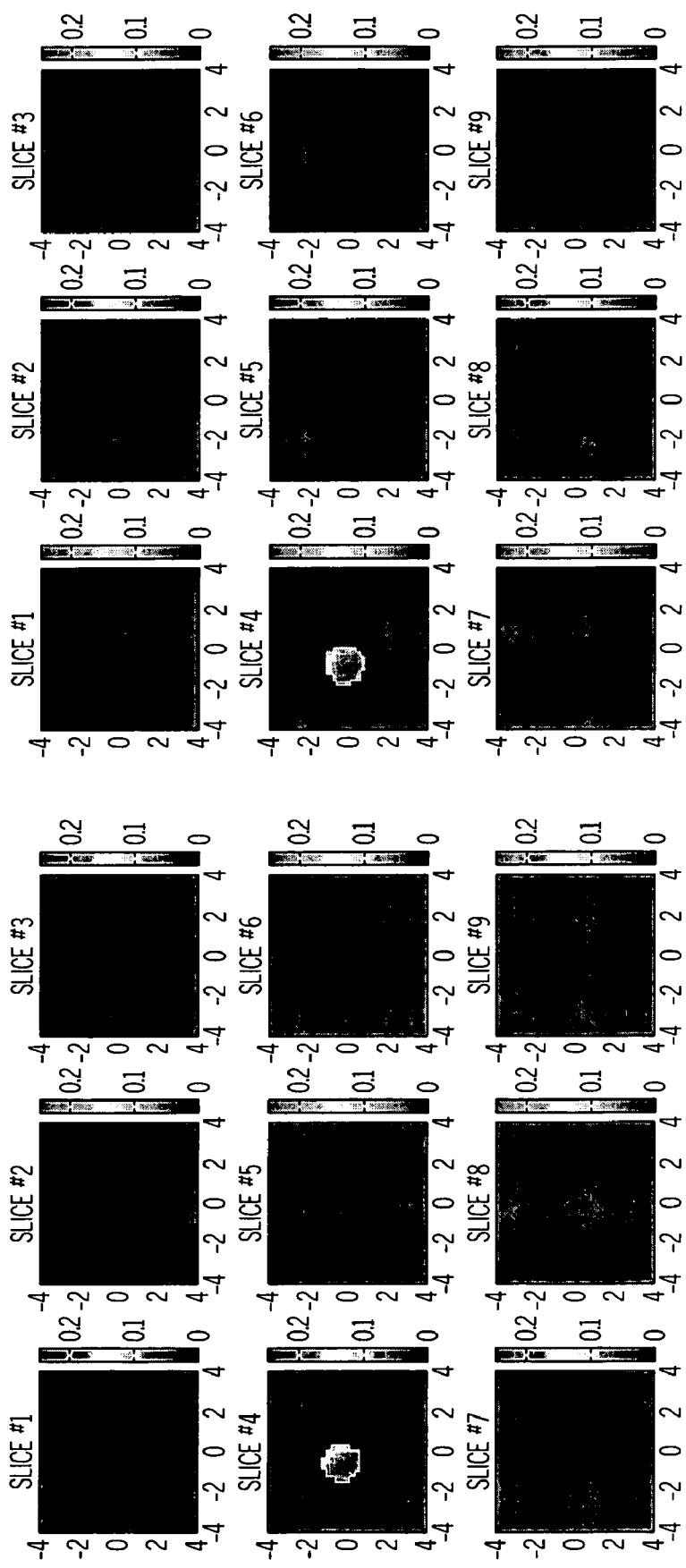

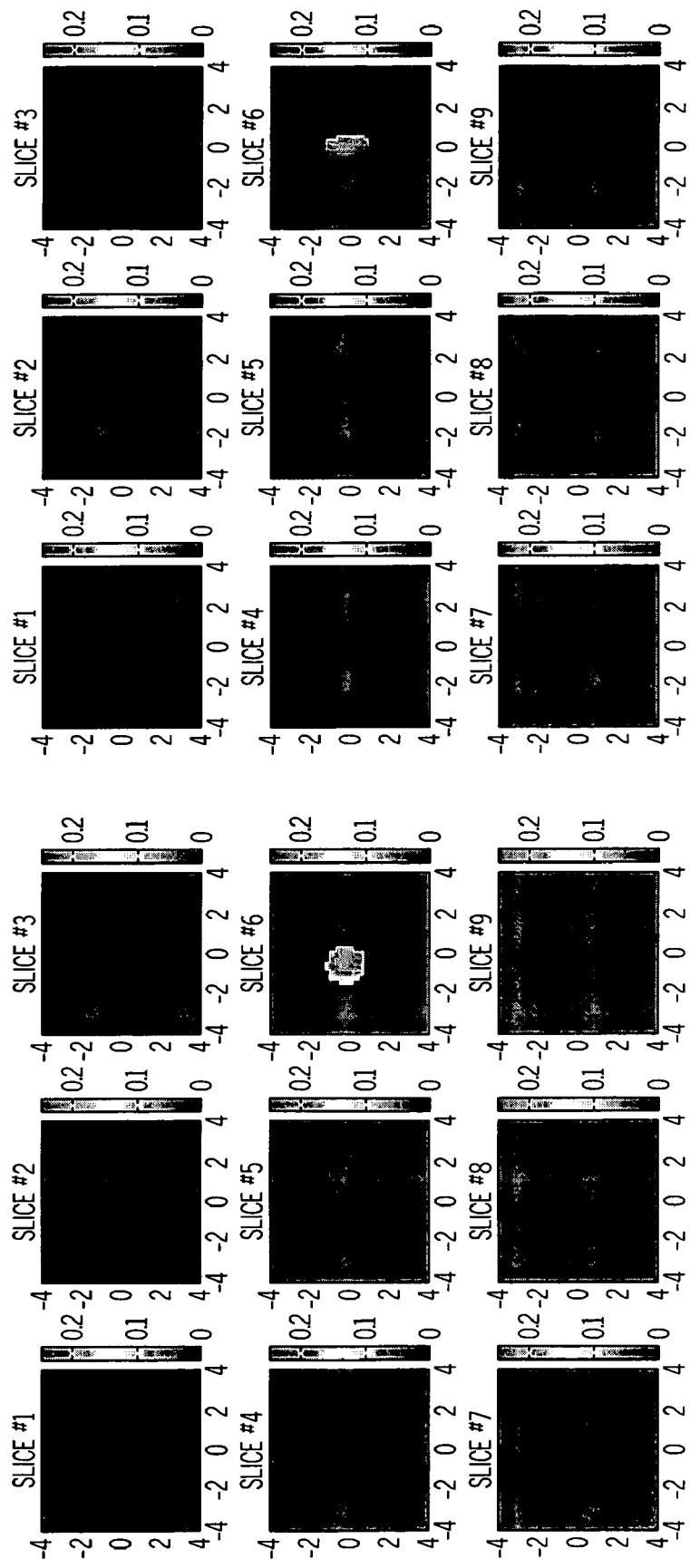

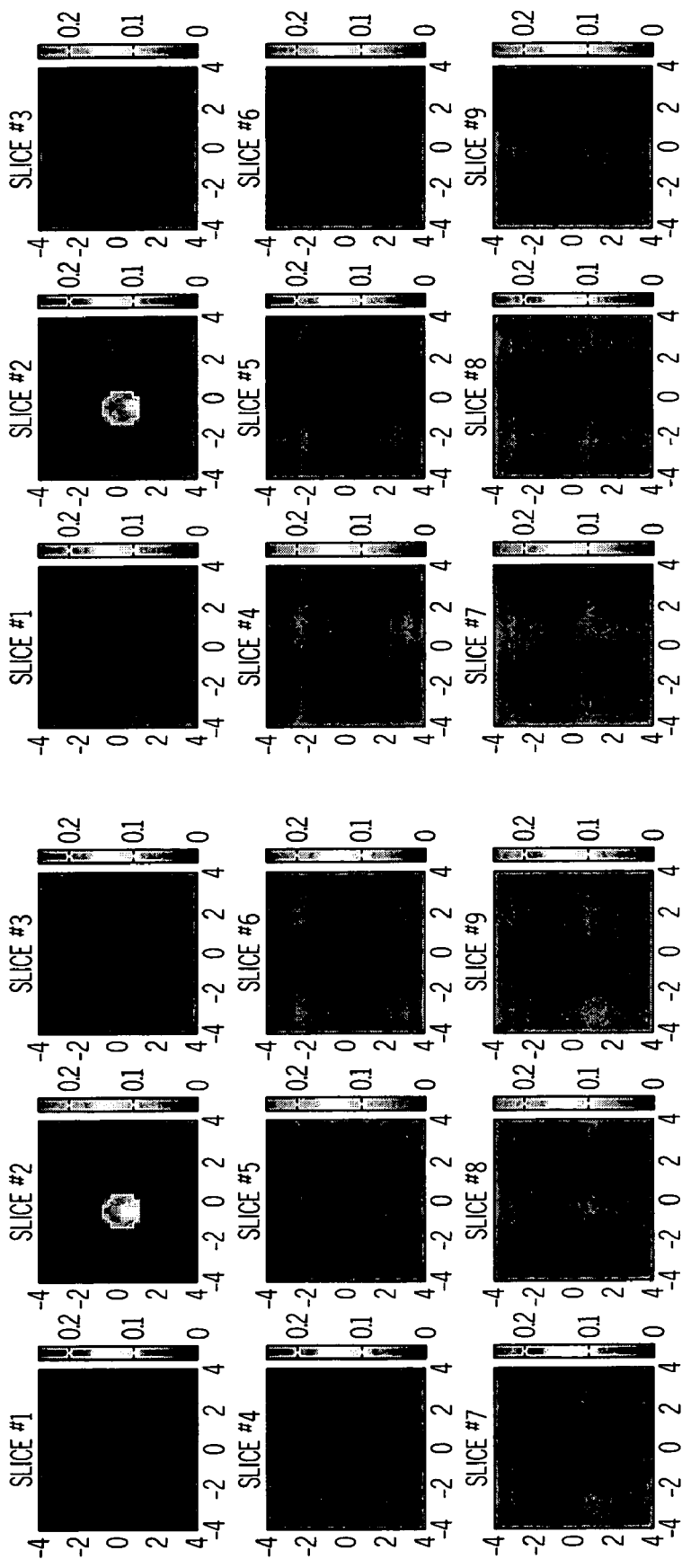
FIG. 16B 140Mhz, 780nm
FIG. 16A 50Mhz, 780nm

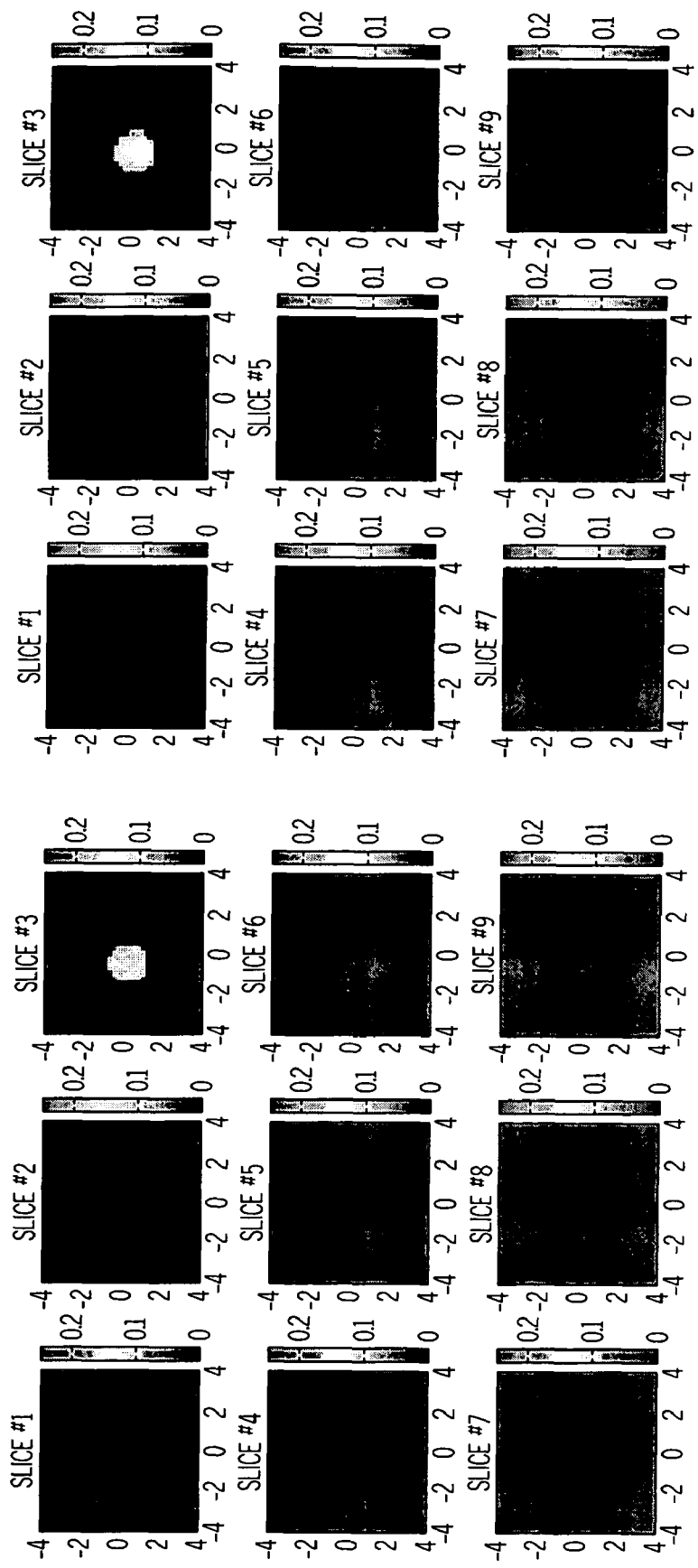

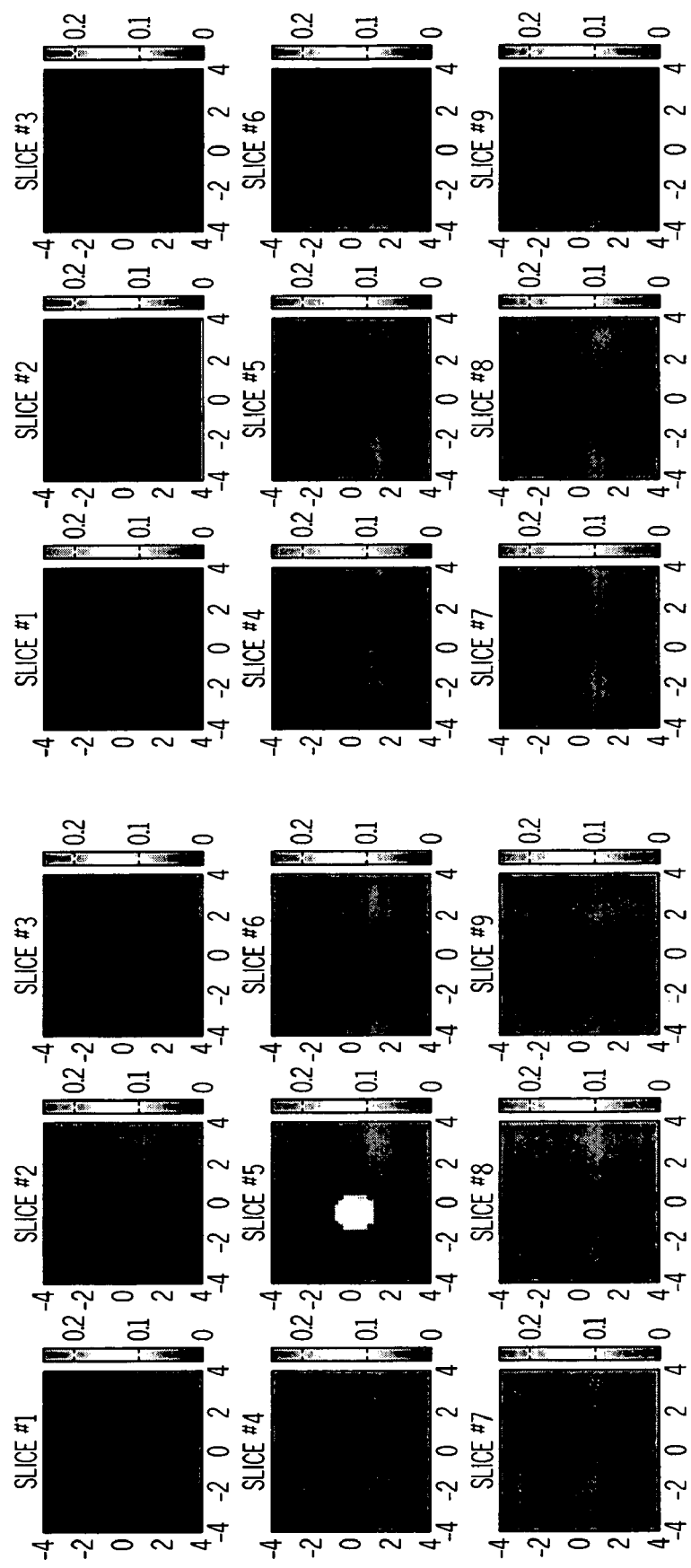

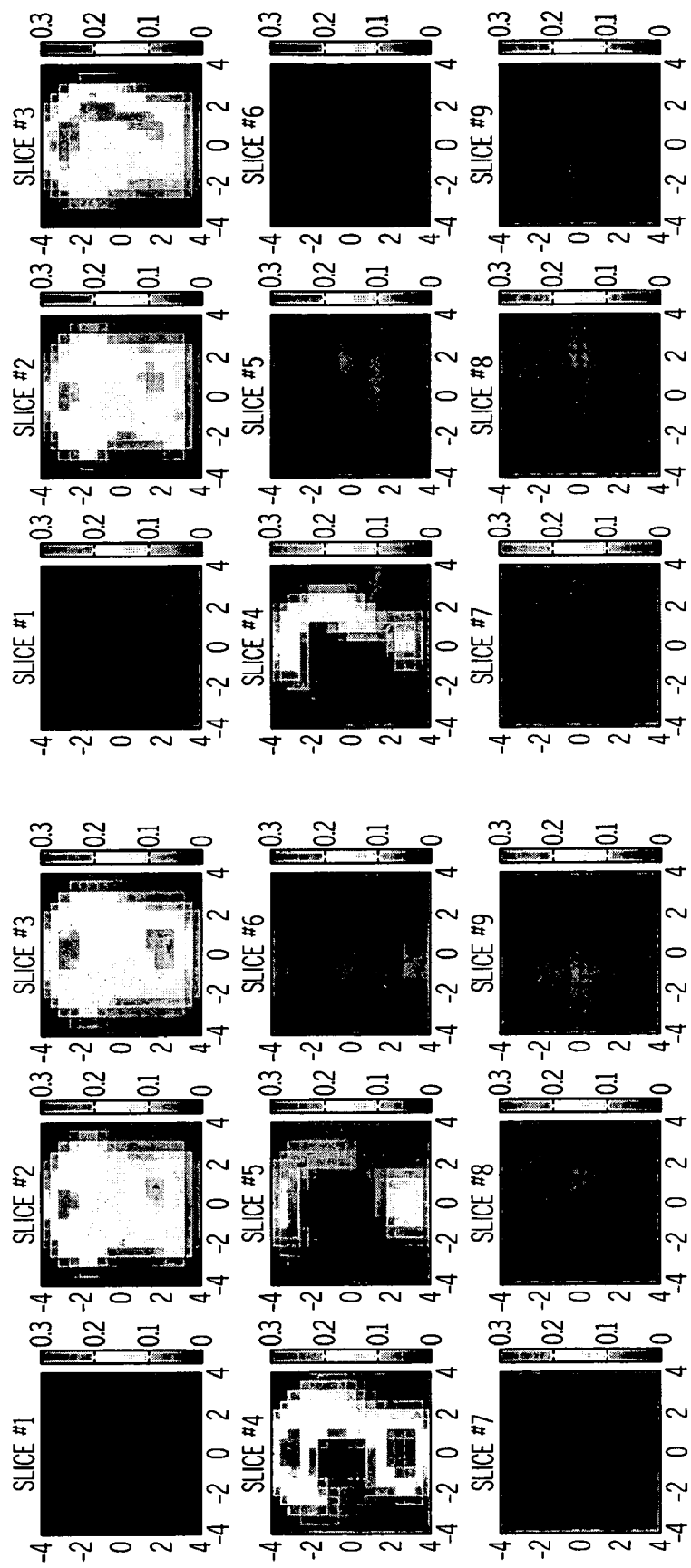

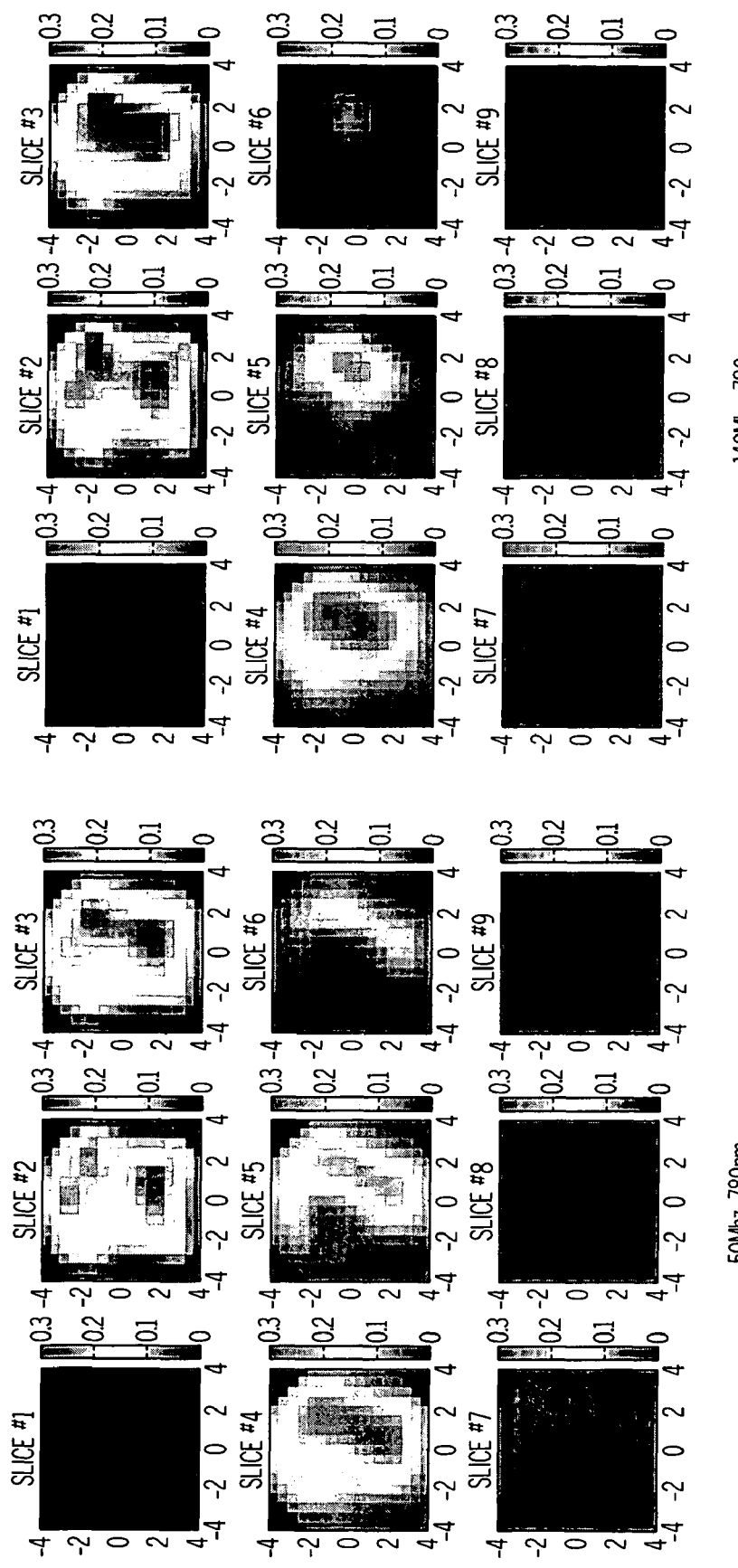
FIG. 17C(2)
FIG. 17C(1)

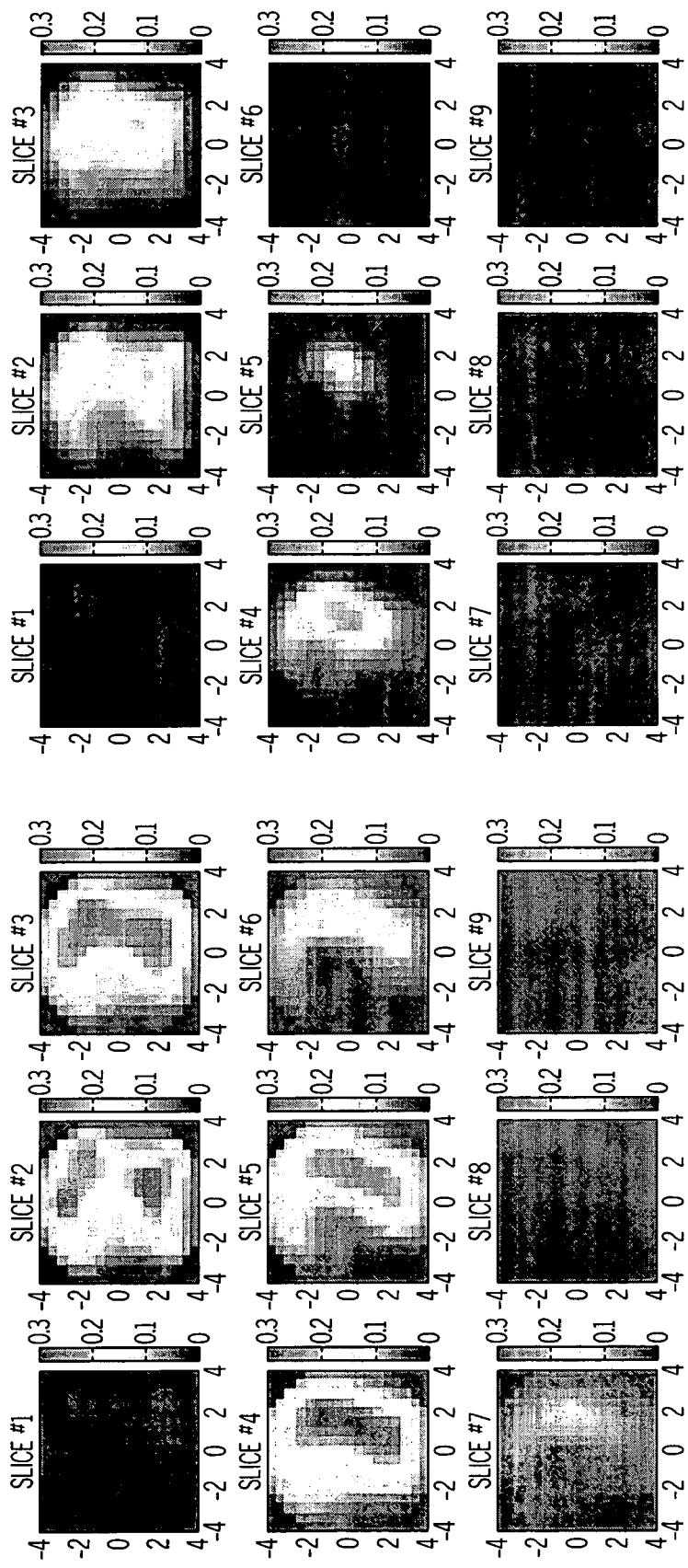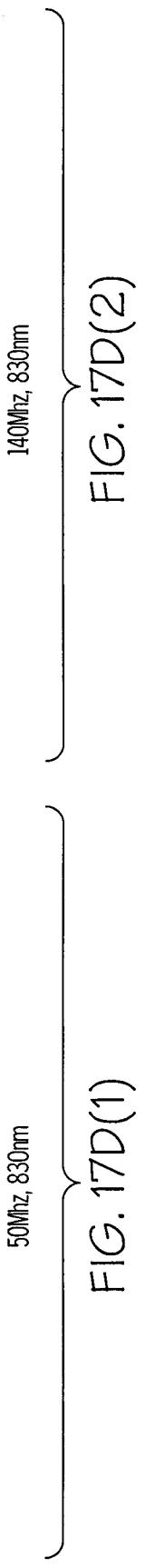
FIG. 17D(2)
140Mhz, 830nm
FIG. 17D(1)
50Mhz, 830nm

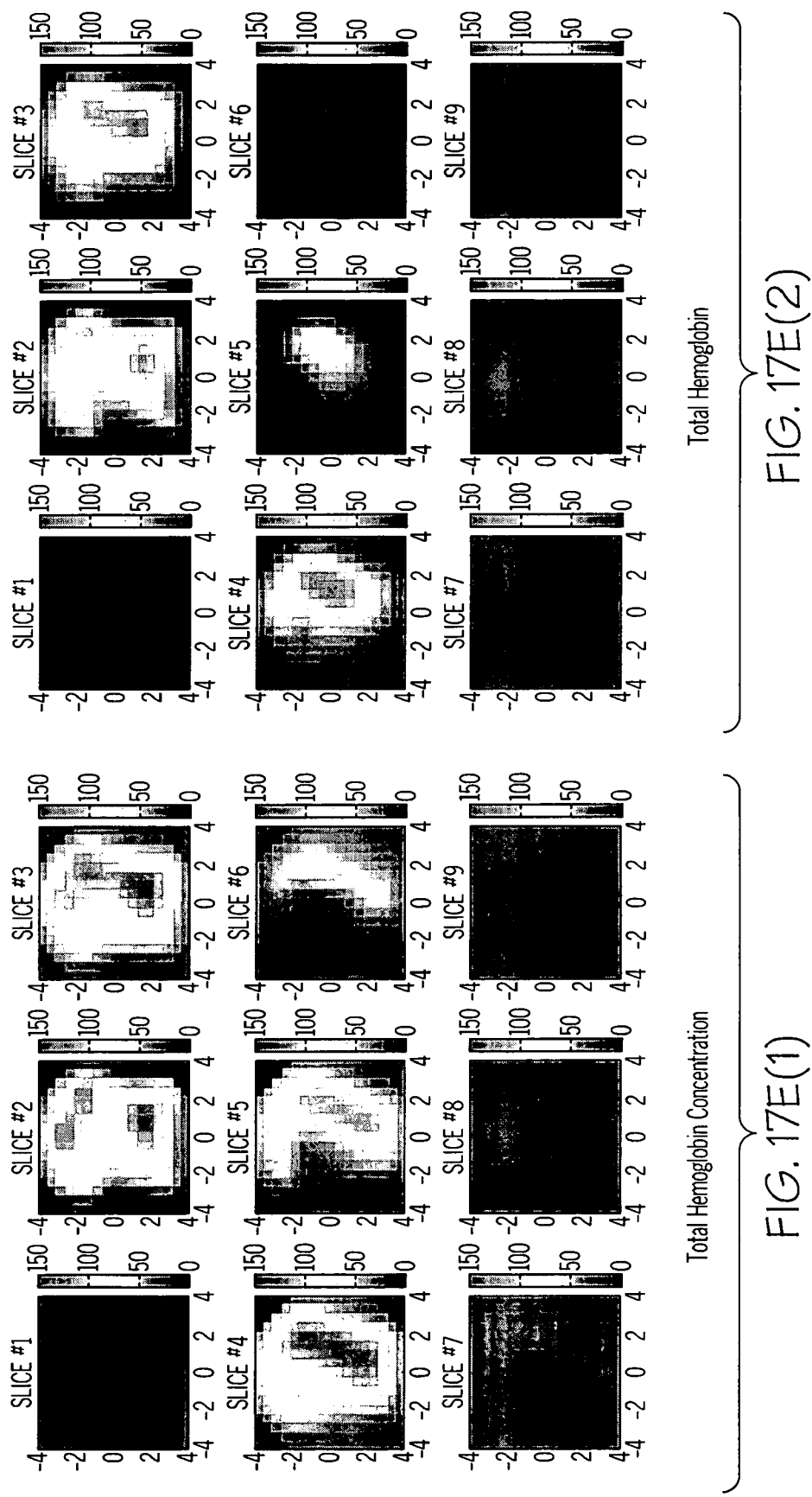

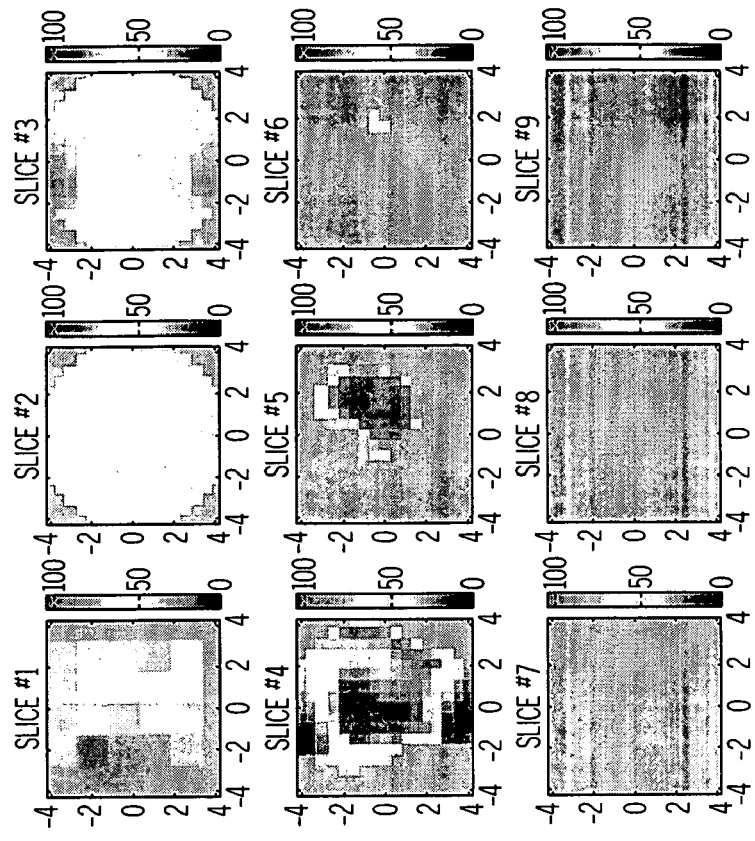
FIG. 17F(2)
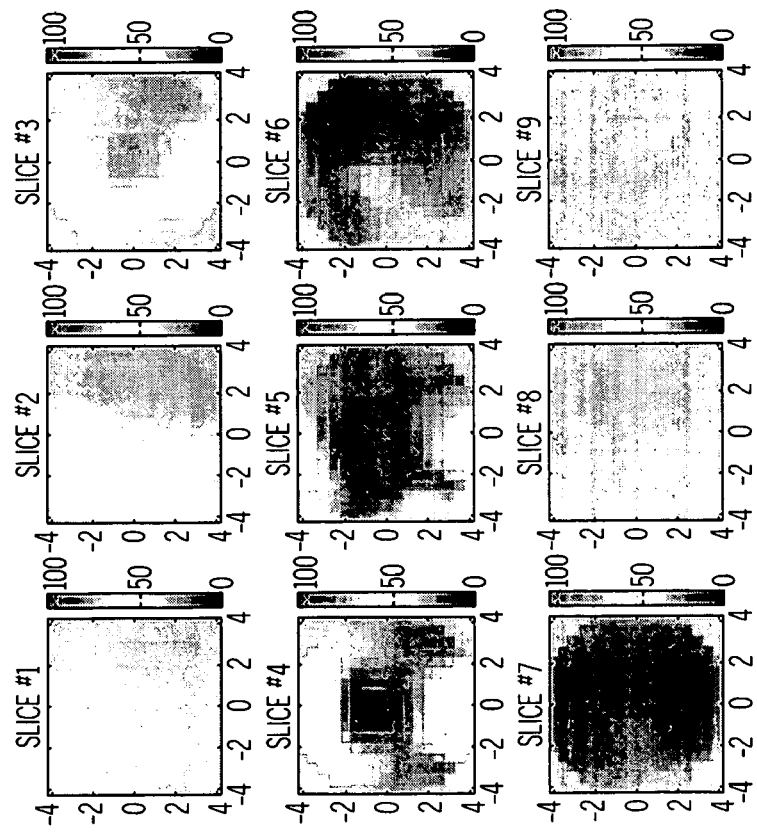
FIG. 17F(1)

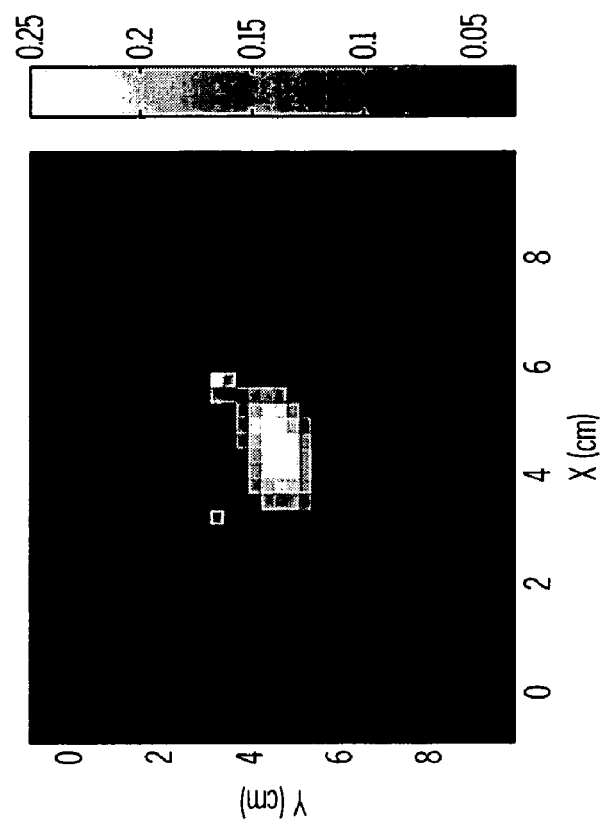
FIG. 19A(2)
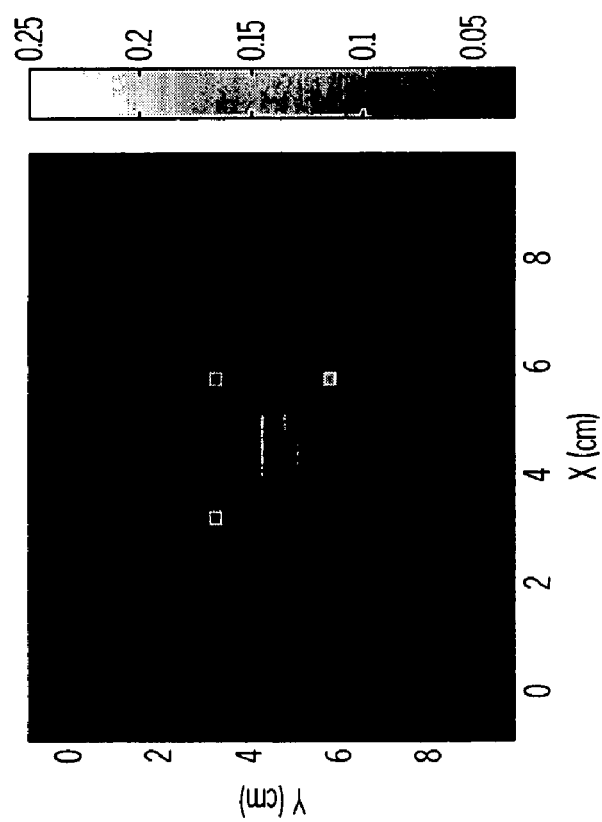
FIG. 19A(1)

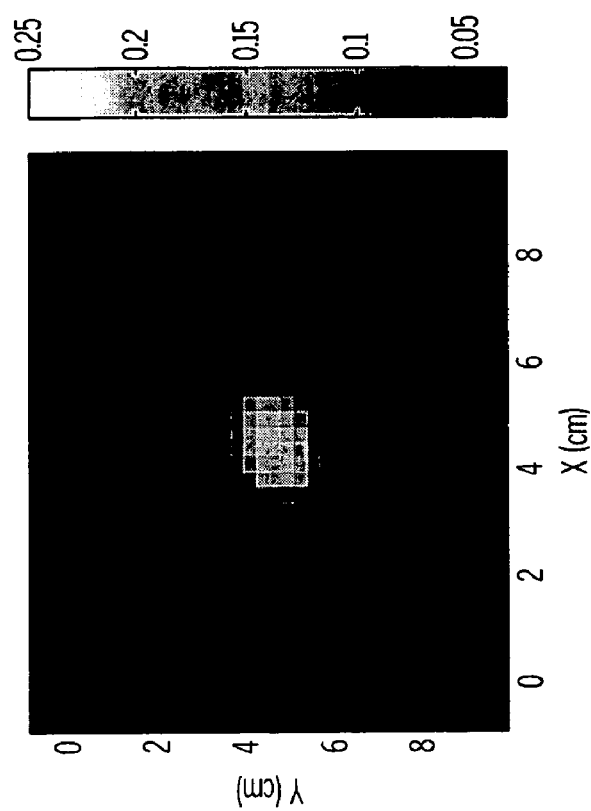
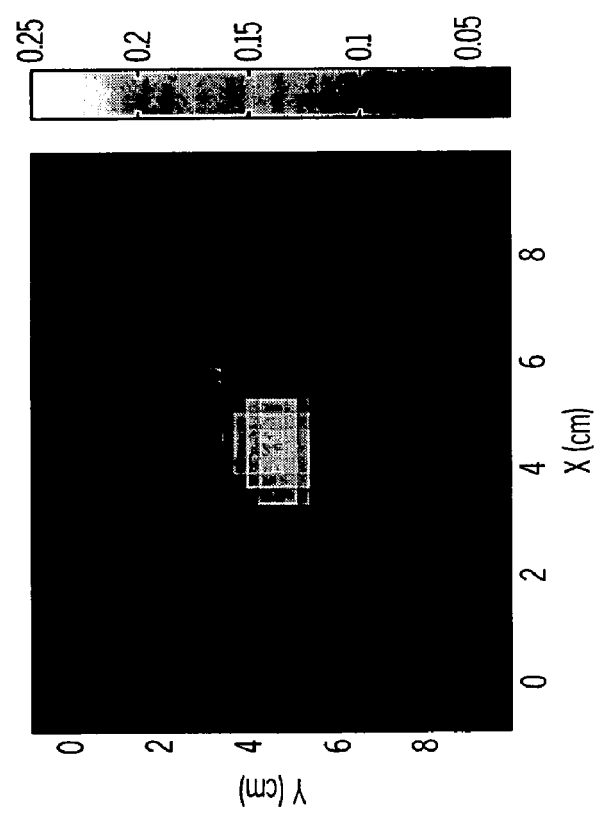
FIG. 19B(2)
FIG. 19B(1)

METHOD AND APPARATUS FOR MEDICAL IMAGING USING COMBINED NEAR-INFRARED OPTICAL TOMOGRAPHY, FLUORESCENT TOMOGRAPHY AND ULTRASOUND

CROSS-REFERENCE TO RELATED APPLICATIONS

This application claims priority to Provisional Application No. 60/832,002 filed Jul. 19, 2006, the entire contents of which are hereby incorporated by reference.

STATEMENT OF FEDERALLY FUNDED RESEARCH

This invention was made with support from the United States Government under contract number R01EB002136 awarded by the National Institutes of Health and contract number DANK) 17-03-1-0690 awarded by the Department of Defense. The Government has certain rights in the invention.

BACKGROUND

This disclosure relates primarily to the field of biological imaging, particularly to medical imaging. More specifically, to medical imaging equipment and methods for medical imaging using combined near-infrared optical tomography, fluorescent tomography and/or ultrasound.

Diffusive optical tomography (DOT) is a form of computer-generated tomography wherein near-infrared light (NIR) is directed at a inclusion (e.g., a lesion, a tumor, a cancer, and so forth) and the amount of light transmitted and/or diffused through the object, and/or reflected from the object, is detected and utilized to reconstruct a digital image of the target area (e.g., the object can exhibit a differential in transmission and/or diffusion from surrounding tissues). This method of imaging is of interest for several reasons, for example, differing soft tissues exhibit differing absorption, transmission and/or scattering of near-infrared light. Therefore, DOT is capable of differentiating optical properties between inclusions and normal soft tissues, wherein alternative tomography methods (e.g., Positron Emission Tomography, Magnetic Resonance Imaging, X-Ray, and so forth) cannot. Another example is that near-infrared light is non-ionizing to bodily tissues, and therefore patients can be subjected to repeated light illumination without harm. This in turn allows physicians to increase the frequency at which they monitor and/or track change in areas of interest (e.g., lesions, tumors, and so forth). Yet further, due to differences at which natural chromophores (e.g., oxygen-hemoglobin) adsorb light differently at different wavelengths, optical tomography is capable of supplying functional information such as hemoglobin concentration and oxygen saturation. For these reasons there is much interest in employing optical tomography for the detection and monitoring of cancerous tissues, especially in breast cancer applications.

Although diffusive optical tomography is a promising medical imaging technique, DOT imaging methods and DOT apparatus have yet to yield high quality reconstructions of inclusions due to fundamental issues with intense light scattering.

Another method of tomography imaging that is of interest is fluorescent diffusive optical tomography (FDOT). Fluorescent diffusive optical tomography is a form of computer-generated tomography wherein an excitation source (e.g., near-infrared light) is directed at an inclusion labeled by a fluorescence targets or dyes or fluorophores. Upon excitation of the fluorophore, the wavelength of the excitation source is shifted to a differing wavelength (e.g., a Stokes-shift) as it is emitted by the fluorophore. The emitted light is then detected and utilized to reconstruct a digital image of the target area, which can exhibit a differential in fluorophore concentration from surrounding tissues (e.g., fluorophore take-up). The digital image can be employed to provide functional characteristics about the inclusion, such as vascular endothelial growth factor (VEGF) conjugated with a dye fluorophore. However, FDOT methods have exhibited less than desirable reconstruction accuracy due to imperfect uptake of the fluorophore and background fluorophore noise.

While diffusive optical tomography provides benefits over alternative imaging methods, they suffer from drawbacks. Each of these imaging methods is confronted with challenges that impede widespread acceptance and implementation. One of the drawbacks is that the accuracy of reconstructed hemoglobin concentration and oxygen saturation is low without location information about the inclusion. It is therefore desirable to develop methods that can provide structural and functional characteristics about inclusions while at the same time facilitating accuracy in inclusion location so that accurate information about hemoglobin concentration and oxygen saturation can be obtained.

SUMMARY

Disclosed herein is a method for medical imaging of an inclusion comprising imaging a tissue volume with a probe comprising: an ultrasound transducer that is operative to provide an on-site estimation of inclusion size and location; a first emitter and a first detector; the first emitter having light of a wavelength of about 400 to about 900 nanometers; the first detector detecting light of a wavelength of about 400 to about 900 nanometers; a source circuit connected in operational communication to the emitter; a detector circuit connected in operational communication to the detector; and a central processing unit connected to the source circuit and the detector circuit; scanning the tissue volume with light having a wavelength of about 400 to about 900 nanometers; the tissue volume comprising a first layer and a second layer; segmenting the scanned tissue volume into an inclusion region comprising a plurality of first voxels and a background region comprising a plurality of second voxels; the volume of each second voxel being larger than the volume of each first voxel; identifying a tissue layer thickness and an approximate tilting angle between the tissue layer and the probe; estimating photon density: $\phi(r,\omega)=f(\mu_{a1},\mu'_{s1},\mu_{a2},\mu'_{s2})$, where $\mu_{a1}$, $\mu_{a2}$, $\mu'_{s1}$, and $\mu'_{s2}$ are absorption and reduced scattering coefficients of first and second layers, respectively; wherein absorption coefficients have the subscript "a", scattering coefficients have the subscript "s", wherein the subscript "1" represents the first layer, the subscript "2" represents the second layer, and the superscript (') stands for the reduced scattering coefficient; applying a conjugate gradient method to estimate fitted optical properties of the first layer and the second layer; minimizing a least-square objective function given as $\min \|\phi(r,\omega)-\phi_0(r,\omega)\|^2$; wherein a forward Jacobian weight matrix $$W_{ij} = \left[\frac{\partial \phi_{ij}}{\partial \mu_{aj}}, \frac{\partial \phi_{ij}}{\partial D_j}\right],$$

that relates the photon density perturbation at detector i and imaging voxel j with absorption coefficient change $\Delta\mu_{aj}$ and diffusion coefficient change $\Delta D_j$, is calculated by using the bulk optical properties simulated from the two-layer layer model and given in equation (1) as:

$$[W_{ij}] = \begin{bmatrix} \frac{\partial \phi_{11}}{\partial \mu_{a1}} & \cdots & \frac{\partial \phi_{1L}}{\partial \mu_{aL}} & \frac{\partial \phi_{11}}{\partial D_1} & \cdots & \frac{\partial \phi_{1L}}{\partial D_L} \\ \frac{\partial \phi_{21}}{\partial \mu_{a1}} & \cdots & \frac{\partial \phi_{2L}}{\partial \mu_{aL}} & \frac{\partial \phi_{21}}{\partial D_1} & \cdots & \frac{\partial \phi_{2L}}{\partial D_L} \\ \vdots & \ddots & \vdots & \vdots & \ddots & \vdots \\ \frac{\partial \phi_{M1}}{\partial \mu_{a1}} & \cdots & \frac{\partial \phi_{ML}}{\partial \mu_{aL}} & \frac{\partial \phi_{M1}}{\partial D_1} & \cdots & \frac{\partial \phi_{ML}}{\partial D_L} \end{bmatrix}, \quad (1)$$

where M is the total number of detector readings; L is the total number of imaging voxels and $\phi_0(r,\omega)$ is the photon density of the first layer.

Disclosed herein too is a method comprising obtaining an image of a tissue volume with a probe comprising an ultrasound transducer that is operative to provide an on-site estimation of inclusion size and location; a first emitter and a first detector; the first emitter having light of a wavelength of about 400 to about 900 nanometers; the first detector detecting light of a wavelength of about 400 to about 900 nanometers; a source circuit connected in operational communication to the emitter; a detector circuit connected in operational communication to the detector; and a central processing unit connected to the source circuit and the detector circuit; scanning the tissue volume with light having a wavelength of about 400 to about 900 nanometers; the tissue volume comprising a first layer and a second layer; segmenting the scanned tissue volume into an inclusion region comprising a plurality of first voxels and a background region comprising a plurality of second voxels; the volume of each second voxel being larger than the volume of each first voxel; reconstructing the image using the equation (2)

$$[U_{sd}]_{M\times 1} = [W_L, W_B]_{M\times N} \times [M_L, M_B]^T_{N\times 1} \quad (2)$$

where $W_L$ and $W_B$ are weight matrices for the inclusion and background regions, respectively;

$$[M_L] = \left[ \int_{1_L} \Delta\mu_a(r')d^3r', \ldots \int_{N_L} \Delta\mu_a(r')d^3r' \right]$$

and $$[M_B] = \left[ \int_{1_B} \Delta\mu_a(r')d^3r', \ldots \int_{N_B} \Delta\mu_a(r')d^3r' \right]$$

are the total absorption distributions of inclusion and background regions, respectively; the weight matrices being calculated based on the background absorption coefficient $\bar{\mu}_a$ and reduced scattering coefficient $\bar{\mu}'_s$ measurements obtained from the normal contralateral breast; a Born approximation being used to relate a scattered field $U_{sd}(r_{si}, r_{di}, \omega)$ measured at the source (s) and detector (d) pair i to absorption variations $\Delta\mu_a(r')$ in each volume element of the two regions within the sample.

Disclosed herein too is an apparatus for medical imaging using diffusive optical tomography and fluorescent diffusive optical tomography comprising; a probe comprising a first emitter and a first detector; the first emitter or the first detector being inclined at an angle θ of up to about 30 degrees to a surface of the probe that contacts tissue; the probe comprising a an ultrasound transducer; a source circuit connected in operational communication to the emitter; a detector circuit connected in operational communication to the detector; a central processing unit connected to the source circuit and the detector circuit; a display operably connected to the central processing unit; and wherein the central processing unit is capable of processing information to provide diffusive optical tomography and fluorescent diffusive optical tomography.

BRIEF DESCRIPTION OF FIGURES

Referring now to the figures, which are exemplary embodiments, and wherein the like elements are numbered alike.

FIG. 4 (a) is an exemplary illustration of the emission and detection of radiation using one emitter and two detectors;

FIG. 7 (b) is an ultrasound image of a small cyst (red arrow) with titled chest wall marked with an array of white arrows;

FIG. 7 (c) is a plot showing the light reflectance R(ρ) ($\log(\rho^2 R(\rho))$) vs. ρ, where R(ρ) is measured at the surface of the breast, ρ is the source detector separation. The curve was linear up to about 4 cm of source-detector separation marked by the arrow;

FIG. 12 (b) depicts a B-scan ultrasound image of a target located on top of the second layer;

FIG. 12 (c) depicts an absorption map at 780 nm from the semi-infinite model;

FIG. 12 (d) depicts a diffusion map at 780 nm from the semi-infinite model;

FIG. 12 (e) depicts an absorption map at 780 nm from the layered model;

FIG. 12 (f) depicts a diffusion map at 780 nm from the layered model;

FIG. 17 (b1, b2), (c1, c2) and (d1, d2) respectively are reconstructed absorption maps obtained from 50 MHz and 140 Mhz at 690 nm, 780 nm and 830 nm, respectively of the cancer shown in the FIG. 17 (a);

FIG. 17 (e1, e2) and (f1, f2) respectively depict the total hemoglobin maps and the blood oxygen saturation maps at 50 MHz and 140 MHz;

FIG. 18 (b) is a graphical representation showing phase versus effective reflection coefficient ($R_{eff}$); and FIG. 19 shows images reconstructed from phantom experimental data: (a) absorbing boundary ($R_{eff}{\approx}0$), (b) partial reflecting boundary ($R_{eff}{\approx}0.6$). #1 and #2 correspond to the first slice of x-y image at 0.5 cm below the surface and the second slice at 1.0 cm below the surface, respectively.

DETAILED DESCRIPTION

Figure 1:
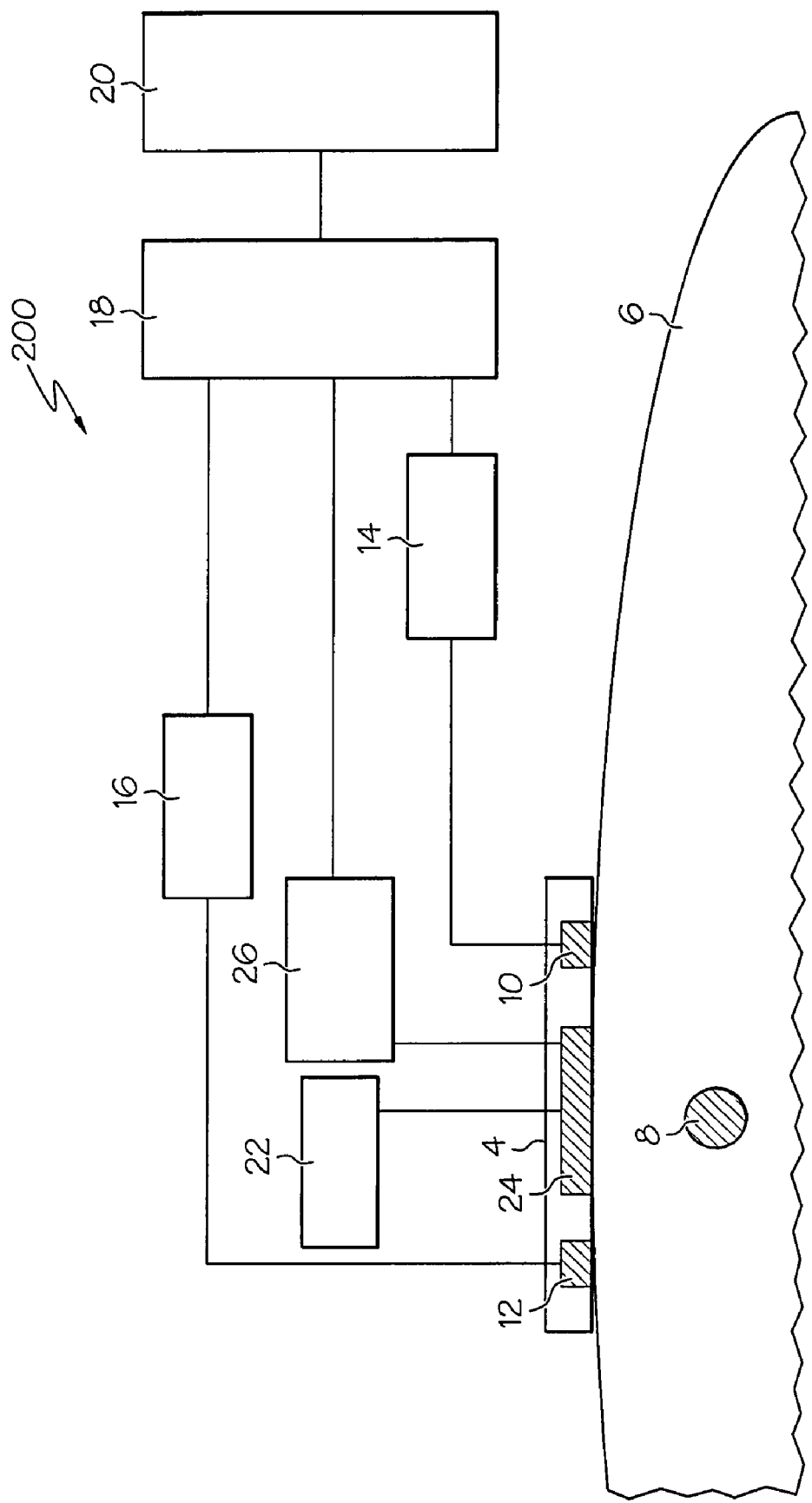
FIG. 1 is a simplified block diagram of an imaging system.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Disclosed herein is a medical imaging apparatus and methods for medical imaging wherein diffusive optical tomography (DOT) and/or fluorescent diffusive optical tomography (FDOT) is employed in conjunction with ultrasound. In one embodiment, the DOT can be employed in conjunction with the FDOT and further in conjunction with ultrasound, xrays, photoacoustic techniques and/or magnetic resonance imaging. In another exemplary embodiment, the DOT can be employed in conjunction with the FDOT and further in conjunction with ultrasound. The images can be enhanced using one or more of three algorithms provided below. The apparatus and methods yield structural information (e.g., position in X, Y, Z coordinates, radius, and so forth) as well as functional information (e.g., fluorophore concentration and hemoglobin concentration) of an absorbing and fluorescing inclusion within a turbid medium (e.g., soft tissue).

The method disclosed herein is advantageous in that it can be used for probing inclusions (e.g., cancers, tumors, lesions, and the like) having a size greater than 2 to 3 centimeters with a low optical modulation frequency to ensure deep penetration. The method can also advantageously be used to probe smaller inclusions located closer to the skin surface with a high optical modulation frequency to ensure high sensitivity. With the real-time co-registered ultrasound guidance on inclusion size and location, an optimal light modulation frequency can be selected which may yield more accurate estimates of inclusion angiogenesis and hypoxia.

Diffuse optical tomography (DOT) in the near infrared region (NIR) provides a unique approach for functional based diagnostic imaging. However, the intense light scattering in tissue produced by the DOT dominates the NIR light propagation and makes three-dimensional localization of inclusions and accurate quantification of the optical properties of these inclusions difficult. Optical tomography guided by co-registered ultrasound (US), magnetic resonance imaging (MRI), photoacoustic techniques or x-ray, has a great potential to overcome the uncertainty of location such inclusions and also to improve light quantification accuracy.

In this co-registration approach, a region of interest (ROI) can be chosen from a non-optical modality ultrasound or MRI, or photoacoustic technique, or x-ray to guide DOT on image reconstruction. However, an accurate delineation of inclusions for DOT from a non-optical modality is difficult due to different contrast mechanisms. Regions of suspicious inclusions seen by optical methods could potentially improve the accuracy of reconstructed optical properties. Described herein is a method that can optically fine tune the inclusions seen by ultrasound, photoacoustic techniques, MRI or x-rays and then reconstruct the functional optical properties of the inclusion, such as optical absorption, hemoglobin concentration and fluorescence concentration.

At the outset, it is to be understood that the term inclusion is to be interpreted as any tissue(s), biological mass(es), biological entity(ies), and/or foreign object(s) that can be differentiated from surrounding tissue(s), biological mass(es), and/or biological entity(ies), using diffusive optical tomography, ultrasound and/or fluorescent diffusive optical tomography. For example, an inclusion can be a tumor that is disposed within soft tissues, such as a tumor within a female breast, wherein the tumor (e.g., comprising epithelial tissues, masenchymal tissues, and so forth) exhibits dissimilar optical diffusion and fluorophore concentration characteristics from surrounding tissues. Also, the term inclusion as used herein can be used interchangeably with the terms biological entity and target. Further, the term structural information refers to any information gathered or determined with respect to the structure, or physical shape, of an inclusion, such as position (e.g., X, Y, Z coordinates), diameter, mass, volume, shape (e.g., circular, elliptical, and so forth), and so forth. Lastly, the term functional information is to be interpreted as any information gathered or determined that can be employed by a physician, operator, or one skilled in the art, to determine additional characteristics about the inclusion.

In one embodiment, frequency domain diffuse optical tomography is used in combination with an ultrasound scanner for probing inclusions of varying size located at different depths under the skin. The frequency domain diffuse optical tomography uses a plurality of frequencies to probe inclusions for size and location under the skin. In one embodiment, the optical tomography uses three frequencies to obtain information about In an exemplary embodiment, the ultrasound scanner is a real-time co-registered ultrasound scanner that is used to simultaneously provide an on-site estimation of inclusion size and location.

In another embodiment, the frequency domain diffuse optical tomography can be used for accurate characterization of inclusions that that are located a depths of less than or equal to about 1 centimeter from the outer surface of the skin. The location of the inclusions is identified by real-time ultrasound. This is accomplished by introducing the light at an angle into the tissue. When light is introduced into a tissue it follows a banana path, as will be depicted later. By varying the path of light in the tissue, it is possible to detect inclusions that are located at depths of less than or equal to about 1 centimeter from the outer surface of the skin.

Referring now to FIG. 1, an exemplary simplified block diagram of an imaging system 200 is illustrated, wherein the imaging system 200 comprises a probe 4 that can be disposed on bodily tissue 6 to image an inclusion 8 therein. The probe 4 comprises a first emitter 10 and a first detector 12, wherein the first emitter 10 is connected in operational communication to a source circuit 14, and the first detector 12 is connected in operational communication to a detector circuit 16. The source circuit 14 and detector circuit 16 are operably connected to a central processing unit 18 (hereinafter referred to as CPU 18), which is operably connected to a display 20 on which an image of the inclusion 8 can be generated. The CPU 18 is capable of controlling the operation of the imaging system 200. The probe also comprises a second emitter 24 for emitting and collecting ultrasonic energy into the body tissue 6.

Figure 2:
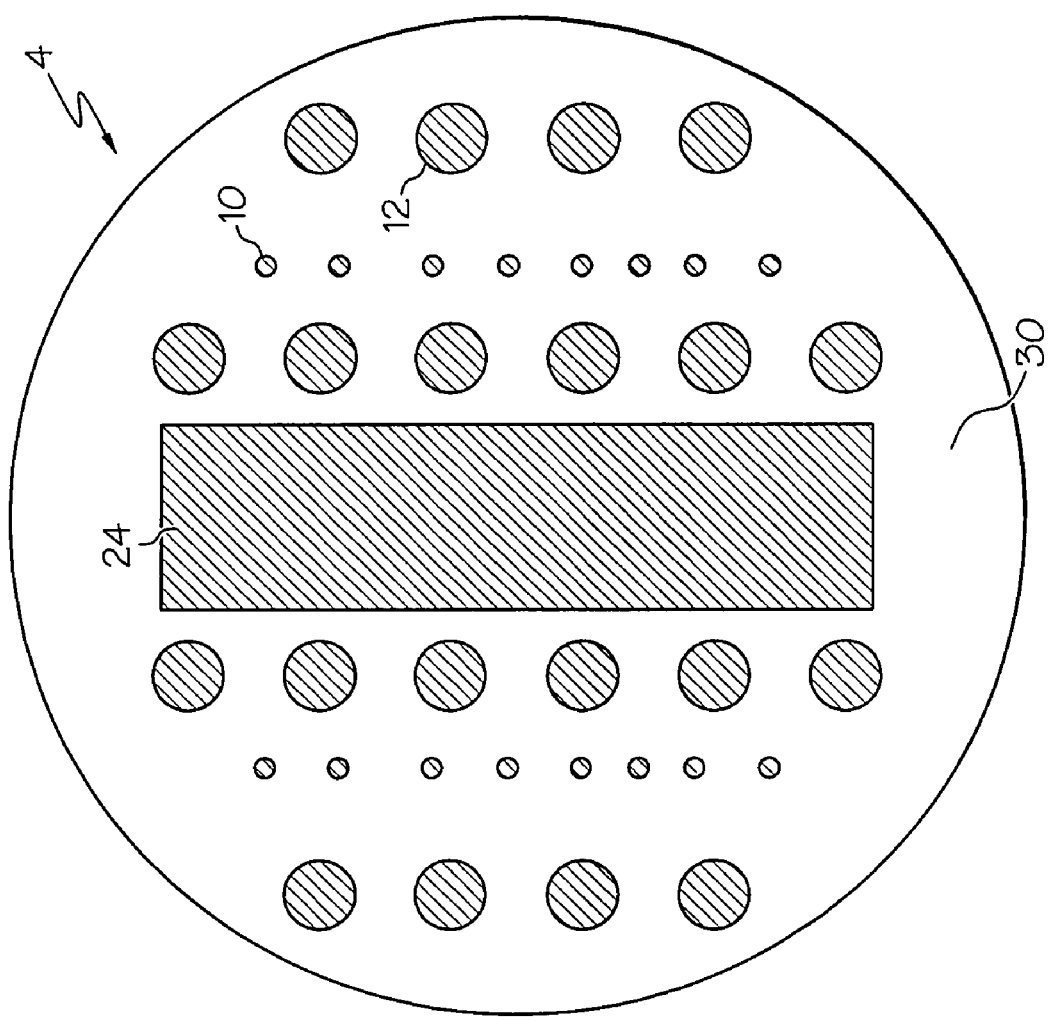
FIG. 2 is an illustration of the front of a probe, which comprising a plurality of emitters and detectors.

FIG. 2 illustrates a front view of the probe 4 having a plurality of first emitters 10 and first detectors 12 disposed on a faceplate 30. The FIG. 2 also depicts a single second emitter (e.g., an ultrasound transducer or array) for emitting and collecting ultrasonic energy into the body tissue. The first emitters 10 are capable of emitting radiation, such as near-ultraviolet light. The first detectors 12 are capable of detecting radiation emitted by the emitters 10 and fluorescence within the target area (e.g., tissue 6 and inclusion 8).

Any number of first emitters 10 and first detectors 12 can be employed to perforin the imaging function. In an exemplary embodiment, the probe 4 can comprise about 1 to about 30 first emitters, specifically about 2 to about 20 first emitters and more specifically about 5 to about 10 first emitters. A preferred number of first emitters in the probe 4 is about 9. In another exemplary embodiment, the probe 4 can comprise about 1 to about 30 first detectors, specifically about 2 to about 20 first detectors and more specifically about 5 to about 10 first detectors. A preferred number of first detectors in the probe 4 is about 10. It is noted however that as the number of first emitters 10 and/or first detectors 12 increases, the imaging time (e.g., the time elapsed before radiation received by a detector can be processed and reconstructed into an image and displayed on display 20 by CPU 18) can increase due to the additional information to be processed by the CPU 18.

The first emitters 10 and the first detectors 12 are generally disposed on the surface of the faceplate 30 so that they are in close proximity to the tissue 6 being imaged. The first emitters 10 and first detectors 12 can be disposed in any configuration, thereby allowing the imaging volume to be expanded or localized based on the number and/or spacing of first emitters 10 and first detectors 12.

Figure 4B:
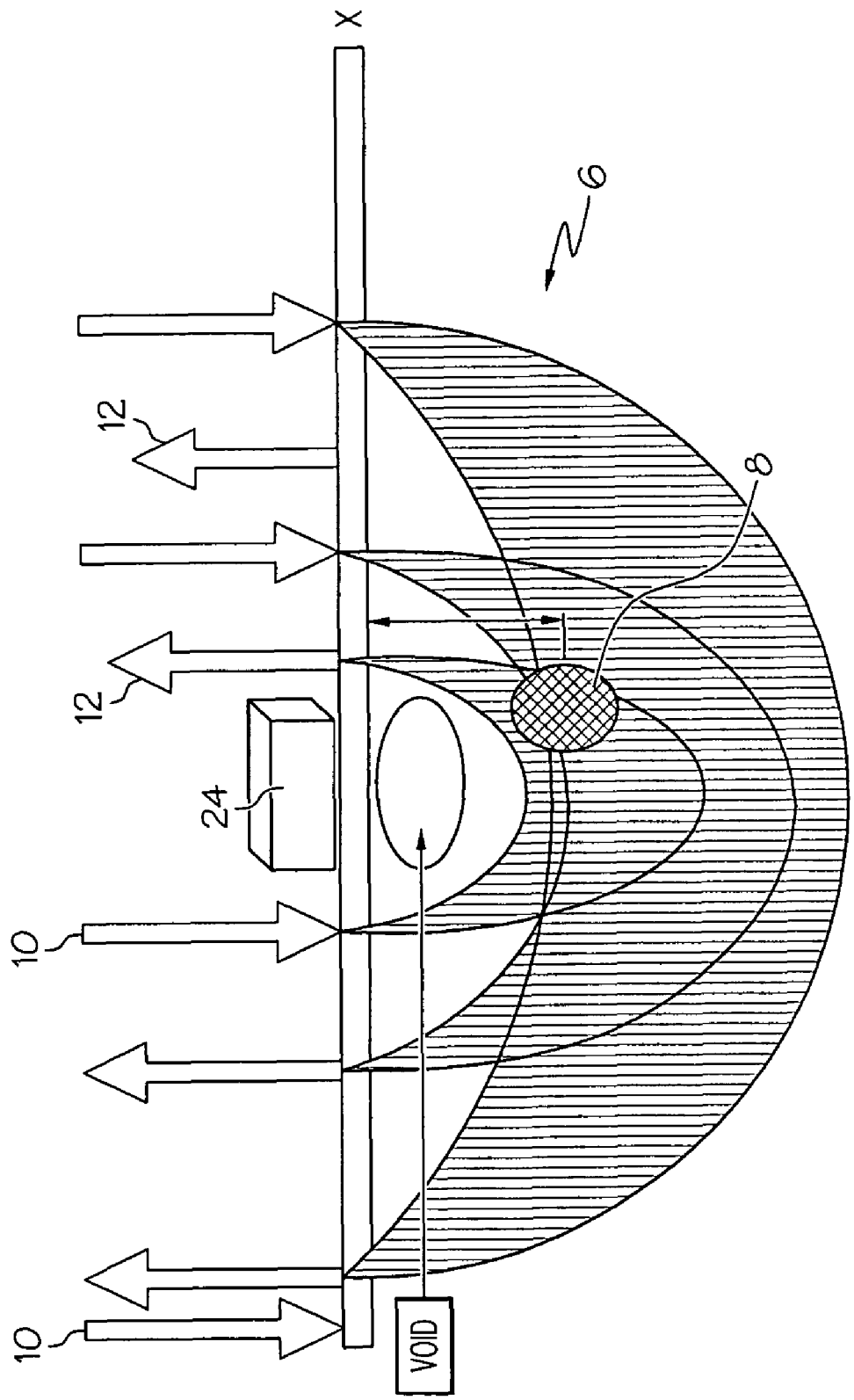
FIG. 4(b) is an exemplary depiction of the use of ultrasound and light for the detection of shallow inclusions, when the emitters are aligned to be perpendicular to the surface of the tissue.
Figure 4C:
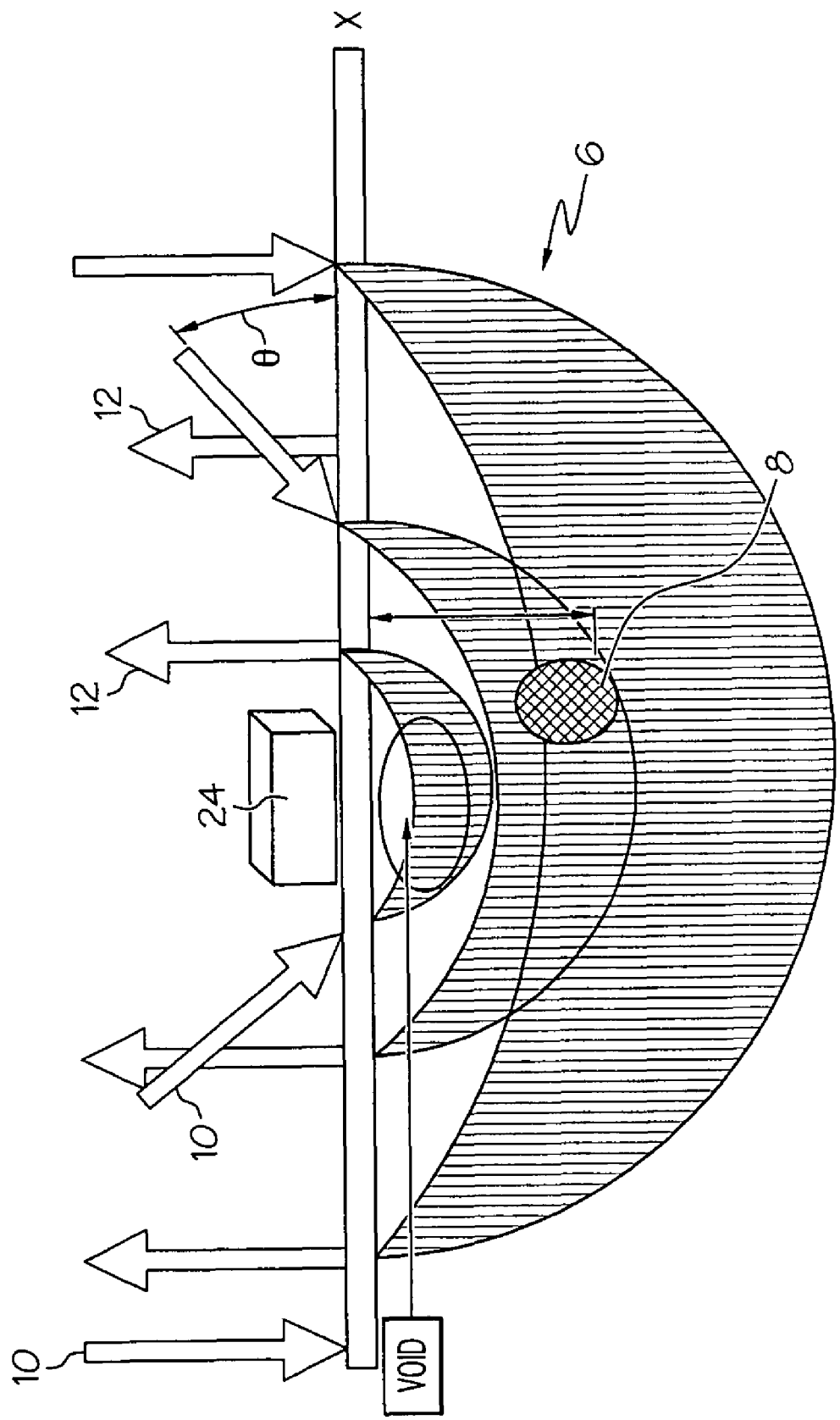
FIG. 4(c) is an exemplary depiction of the use of ultrasound and light for the detection of shallow inclusions, when the emitters are aligned at an angle of about 20 to about 30 degrees to the surface of the tissue.

In an exemplary embodiment, some of the first emitters 10 can be inclined at an angle θ to the surface of the probe 4, when the probe 4 is in its undisturbed form. This is depicted later in the FIG. 4(*c*). The inclination of the emitters improves image quality for shallow targets. The angle θ can be about 10 to about 50 degrees, specifically about 20 to about 30 degrees as shown in FIG. 4(*c*).

The probe 4 can also have a plurality of second emitters 24. In an exemplary embodiment, the second emitter is an ultrasound transducer. In one embodiment, the ultrasound transducer is an ultrasound array. It will be recognized that any ultrasound array can be used in the probe 4. For example, the ultrasound array can be 1-dimensional, 2-dimensional, 1.5-dimensional or 1.75-dimensional. In an exemplary embodiment, the probe 4 can have about 1 to about 10 ultrasound transducers. A preferred number of ultrasound transducers is 1. In the present embodiment a 1-dimensional array is used.

The ultrasound transducer uses ultrasonic energy having a frequency range of approximately 20,000 to 10 billion cycles per second (hertz). Ultrasound has different velocities in tissues that differ in density and elasticity from others. This property permits the use of ultrasound in outlining the shape of various tissues and organs in the body.

The specific shape of the probe 4 and/or the faceplate 30 is desirably configured to be an ergonomic design that is suited to traverse across the tissue 6 of a patient without causing discomfort to the patient (e.g., the faceplate 30 can comprise rounded edges, a smooth surface, and so forth). The probe can have a completely absorbing surface, i.e., it can be black in color. However, it can also have a reflecting surface, i.e., it can be non-black in color. In an exemplary embodiment, it can be white in color.

In addition, the probe 4 can be configured such that it can be hand-held by an operator. While the exemplary depiction of the probe 4 in the FIG. 2 shows a circular cross-sectional area, the cross-sectional area can have a geometry that is square, rectangular, triangular or polygonal. In addition, it is further envisioned the probe 4 can be releasably secured to the conduit (e.g., fiber optic cables, wires, and so forth) that connects the probe 4 in operable communication with the source circuit 14 and detector circuit 16. Furthermore, the optical fibers deployed on the probe 4 can be perpendicular to the probe surface or titled with certain angle to ensure best near infrared light illumination of the biological tissue under evaluation as shown in FIG. 4(*c*).

It is desirable for the surface of the probe 4 to be manufactured from an organic polymer, preferably one that is flexible at room temperature, so that it can be used to accommodate the contours of a body whose tissue is under observation. The organic polymer can comprise a wide variety of thermoplastic resins, blend of thermoplastic resins, thermosetting resins, or blends of thermoplastic resins with thermosetting resins. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, or the like, or a combination comprising at last one of the foregoing organic polymers. Exemplary organic polymers for use in the probe 4 are elastomers that have glass transition temperatures below room temperature.

Examples of the organic polymer are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, fluorinated ethylene propylene, perfluoroalkoxyethylene, polychlorotrifluoroethylene, polyvinylidene fluoride, or the like, or a combination comprising at least one of the foregoing organic polymers.

Examples of blends of thermoplastic resins include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

Examples of thermosetting resins include polyurethane, natural rubber, synthetic rubber, epoxy, phenolic, polyesters, polyamides, polysiloxanes, or the like, or a combination comprising at least one of the foregoing thermosetting resins. Blends of thermoset resins as well as blends of thermoplastic resins with thermosets can be utilized. An exemplary thermosetting resin is polydimethylsiloxane (PDMS).

Figure 3:
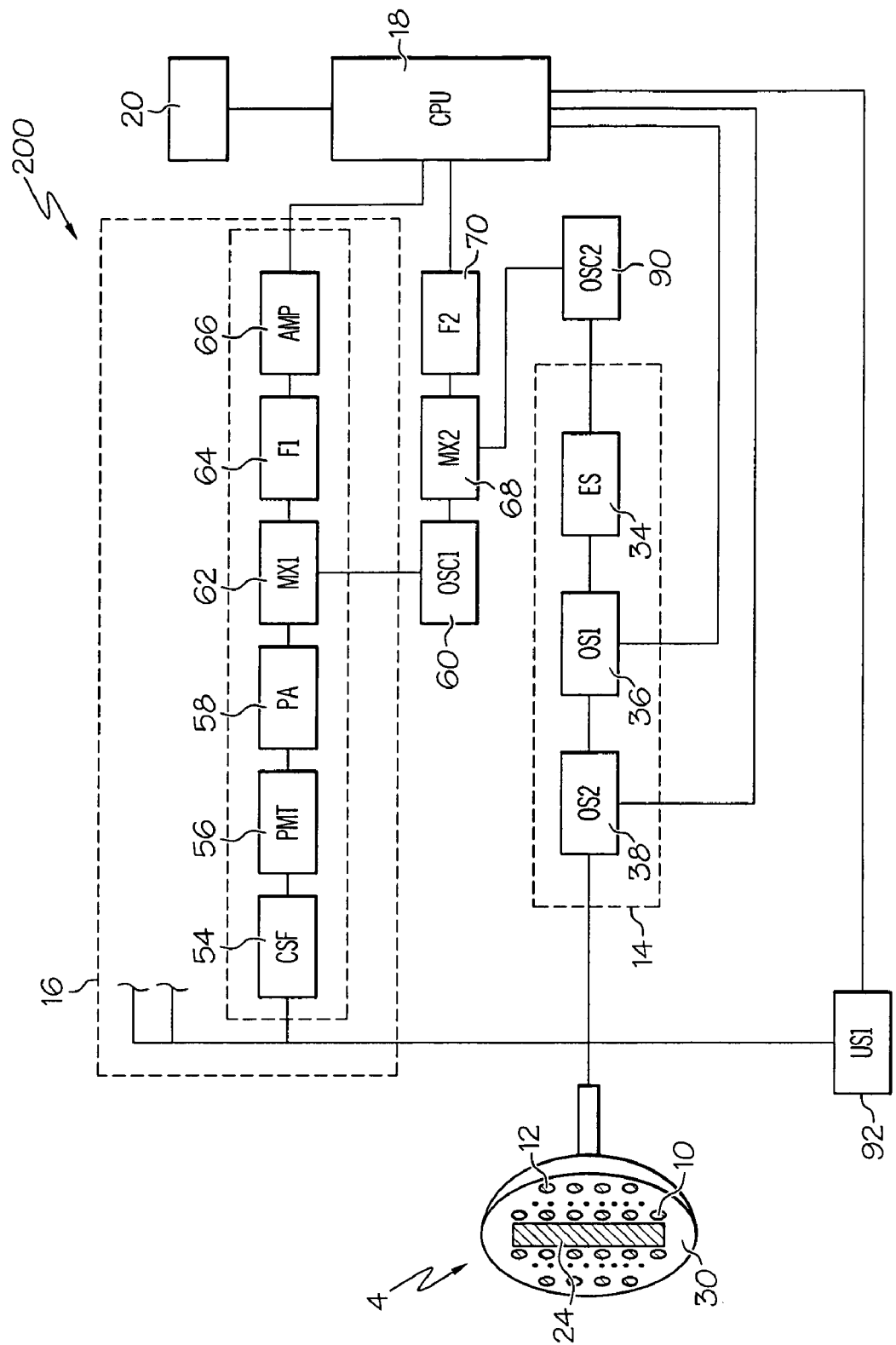
FIG. 3 is an exemplary imaging system.

Referring now to FIG. 3, an exemplary embodiment of an imaging system 200 is illustrated. The imaging system 200 comprises a probe 4 having a plurality of first emitters 10 operably connected to a source circuit 14 via optical fibers 32. In one embodiment, the probe has 9 emitters. The source circuit 14 comprises an excitation source (ES) 34 that is optically connected to a primary optical switch (OS1) 36. The excitation source (ES) 34 comprises multiple excitation elements therein (not shown), such as pigtailed laser diodes capable of emitting near-infrared radiation at 660 nm or 690 nm and near-infrared radiation at 780 nm and 830 nm (e.g., commercially available from Thorlabs Inc.) that is modulated at predetermined frequencies (e.g., 350 MHz, 140 MHz and 50 MHz) by an oscillator (OSC2) 90, which is connected thereto.

The primary optical switch (OS1) 36 is capable of selectively connecting the emissions from any of the excitation elements, or any combination of excitation elements, to a secondary optical switch (OS2) 38 (e.g., commercially available from Piezosystem Jena Inc.). The secondary optical switch (OS2) 38 is capable of selectively directing the emissions from the primary optical switch (OS1) 36 connected to any combination of the nine emitters 10, hence allowing the emission of radiation through the emitters 10 selected. The primary optical switch (OS1) 36 and the secondary optical switch (OS2) 38 are connected in operable communication with, and controlled by, CPU 18.

In FIG. 4(*a*), an exemplary illustration of the emission and detection of radiation using one first emitter 10 and two first detectors 12. To be more specific, first emitter 10 emits radiation 72 through tissue 6 upon an inclusion 8 disposed a distance 82 from the first emitter 10. Fluorophores within the inclusion 8 are excited by the radiation 72 and fluoresce in the form of fluorescence signals 74 and 76, which are detected by a first detector 78 and a second detector 80 that are disposed a distance 84 and a distance 86 from the first emitter 10, respectively. The fluorophores can be disposed within the inclusion 8 via the injection of a fluorophore dye, such as Cy5.5 and the like.

FIG. 4(*b*) depicts a configuration where the first emitters 10 and the first detectors 12 are disposed so as to be parallel to one another. In this configuration, the first emitters 10 and the first detectors 12 are generally perpendicular to the skin of the patient. In this configuration the light introduced into the tissue travels a crescent-like path, and thus may not impinge on inclusions that are closer to the skin.

FIG. 4(*c*) depicts a configuration where the first emitters 10 and/or the first detectors 12 are inclined at an angle of about 20 to about 30 degrees. In this configuration, shallow inclusions located less than about 0.5 to about 0.7 centimeters from the surface of the skin can be detected. Source to detector distances of about 0.5 to about 10 centimeters, specifically about 1 to about 8, more specifically about 2 to about 7 centimeters enable the detection of shallow inclusions. As will be shown later, the probe 4 with a reflection boundary is suitable for detecting shallow targets with high sensitivity.

Figure 5:
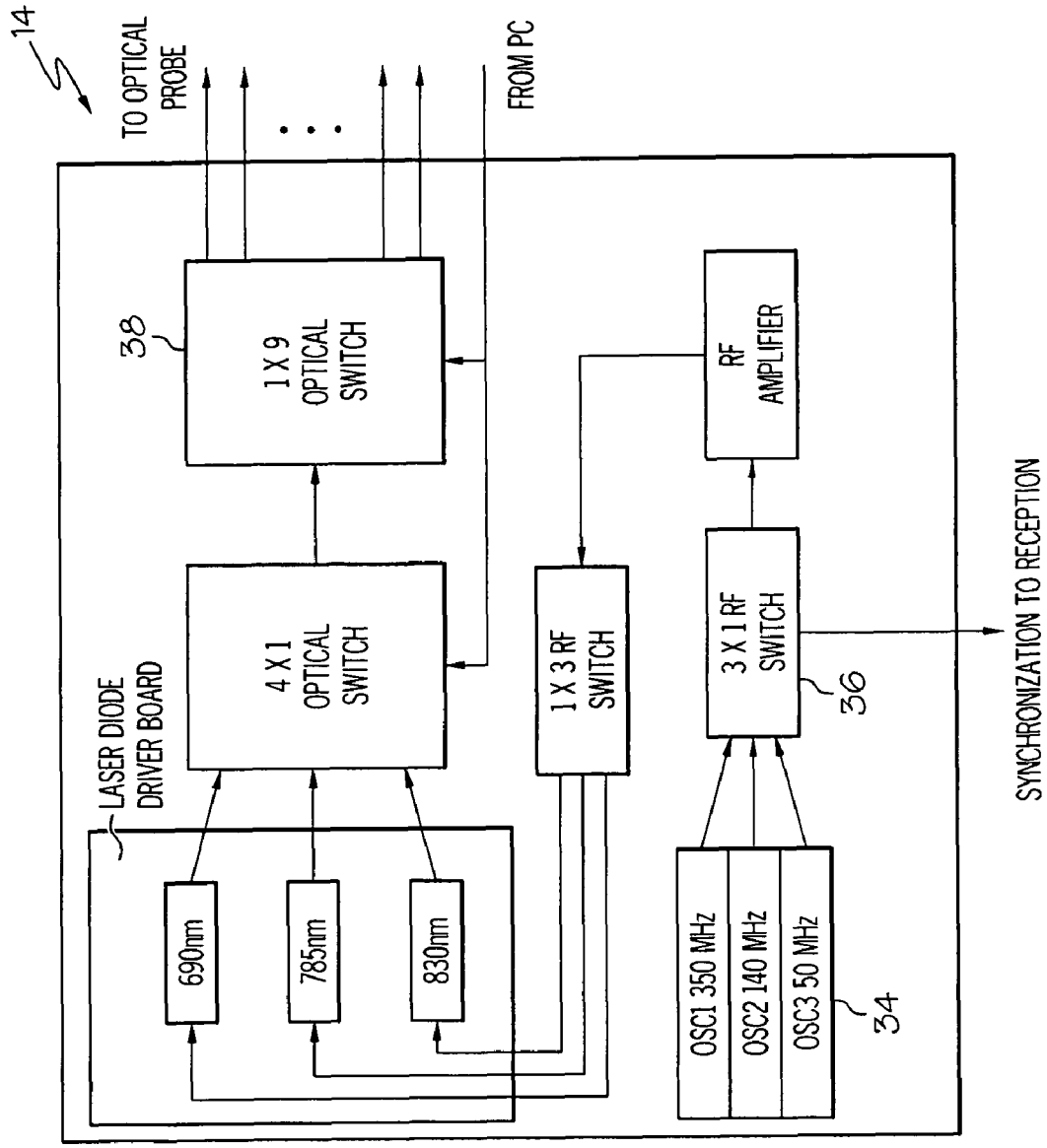
FIG. 5 is an exemplary schematic diagram of the emitter subsystem.

FIG. 5 is another exemplary depiction of a source circuit 14. The source subsystem has a plurality of pigtailed laser diodes 34 that emit light having wavelengths of about 400 to about 900 nanometers are in operative communication with a corresponding number of radio frequency (RF) oscillators. For each modulation frequency, the outputs of the laser diodes are sequentially delivered to a plurality of first emitter locations on the probe through optical switches 36 and 38.

In the embodiment depicted in the FIG. 5, three pigtailed laser diodes 34 that emit light having wavelengths of 690 nm, 780 nm and 830 nm (OZ Optics Inc) are in operative communication with and three RF oscillators of 350 MHz, 140 MHz and 50 MHz. For each modulation frequency, the outputs of the laser diodes were sequentially delivered to 9 locations on the probe through 3×1 and 1×9 optical switches 36 and 38 respectively. The laser diodes were obtained from OZ Optics Inc. and the optical switches were obtained from PiezoJena Inc.

The ten first detectors 12 on the probe 4 are operably connected to the detector circuit 16 via optical fibers 52. The detector circuit 16 comprises detector sub-circuits 54 for each first detector 12 and optically connected thereto via portions of optical fibers 52. Each detector sub-circuit 54 comprises a collimating system and filter (CSF) 54, which is capable of receiving an optical signal (e.g., light) from a first detector 12, collimating the optical signal, and optionally filtering the optical signal to a specific desired frequency range. The optical signal emitted from the collimating system and filter (CSF) 54 is then directed to a photomultiplier tube (PMT) 56 (e.g., commercially available from Hamamatsu Inc.) and converted into a voltage, which is subsequently amplified by pre-amp (PA) 58 (e.g., by about 40 mV).

The resulting voltage is mixed with an output carrier signal having a predetermined frequency (e.g., 350.02 MHz, 140.02 MHz and 50.02 MHz) by a local oscillator (OSC1) 60 that is connected in electrical communication with the voltage via mixer 62. The heterodyned signals output by mixer 62 are filtered by a narrowband filters (F1) 64 and further amplified (e.g., by 30 dB) by amplifier (AMP) 66. The amplified signals are then sampled at a predetermined frequency (e.g., 250 KHz) by an analog to digital conversion (A/D) board inside the CPU 18. The signals output by the oscillator (OSC1) 60 are directly mixed with the output of oscillator (OSC2) 90 by mixer 68 to produce a reference signal (e.g., a 20 KHz reference signal). The 20 kHz reference signal is then filtered by a narrowband filter 70 (e.g., 20 KHz) and provided as input to the CPU 18.

Figure 6:
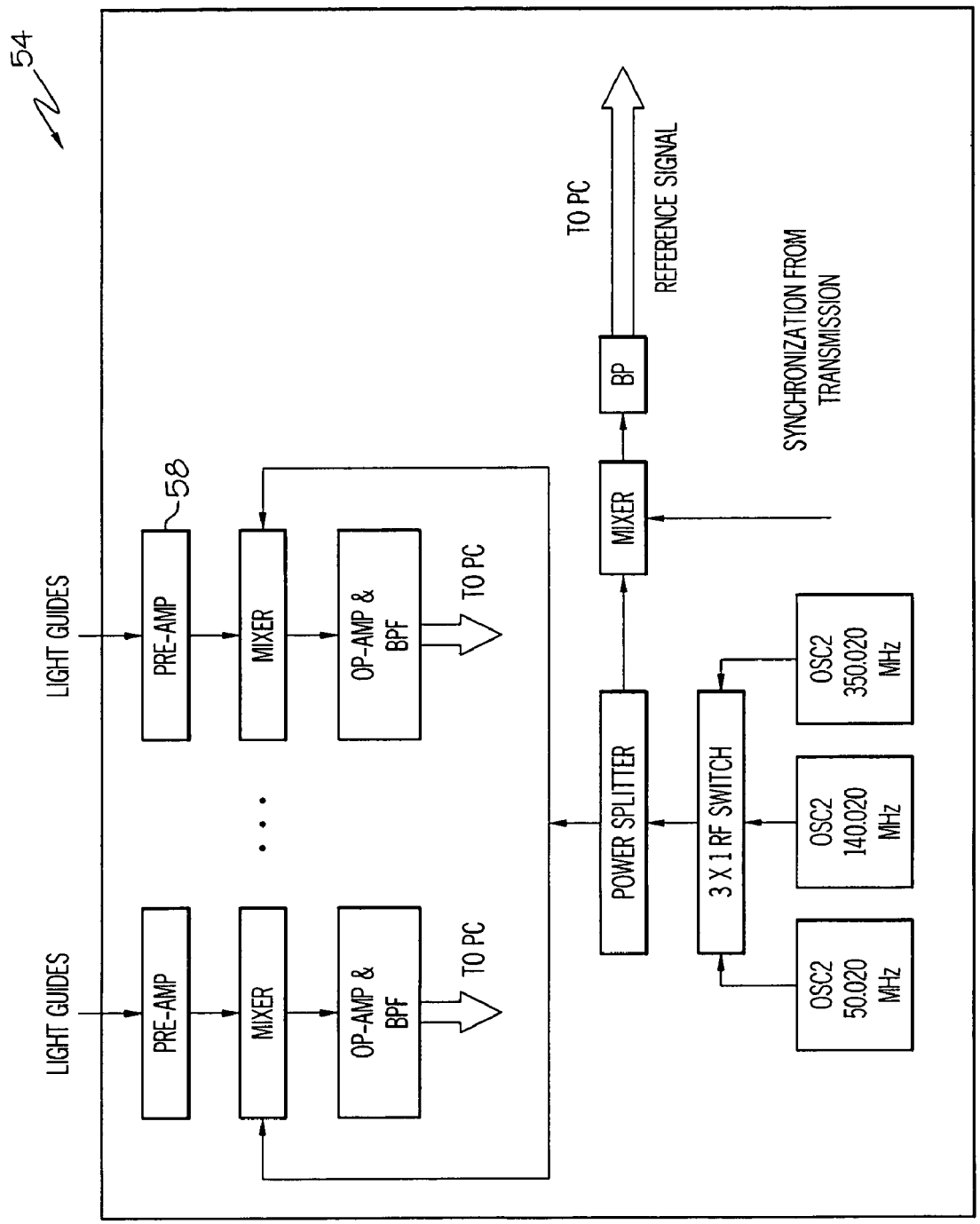
FIG. 6 is an exemplary schematic diagram of the detector subsystem.

FIG. 6 is an exemplary depiction of a detector circuit subsystem 54. The detection subsystem comprises a plurality of parallel channels. In one embodiment, the detection subsystem comprises 10 parallel channels. The light guides couple the diffusively detected light from the tissue to photomultiplier tubes (PMTs) 56. The outputs of the PMTs 56 were amplified by low-noise preamplifiers 58 and mixed with the corresponding oscillator offset 20 kHz higher to produce both sum and difference signals. The 20 kHz difference signals were further amplified by 50 dB and bandpass filtered before sampled by A/D converters. Two National Instrument (NI) data acquisition cards (8 channels on each card) were synchronized to acquire data from 10 parallel detection channels. The 20 kHz reference signal was produced by directly mixing the outputs of the corresponding transmit and receive oscillators at each modulation frequency. The sampled reference signal was used to retrieve phase information. To speed up data acquisition, one or two modulation frequencies can be selected on site for each breast lesion based on the depth and target size measured by real-time ultrasound. The entire data acquisition of 9 10 source-detector positions for three wavelengths was less than 60 seconds, specifically less than 30 seconds, and more specifically less than 10 seconds, which was fast enough to acquire data from patients and avoid potential motion artifacts.

With reference now once again to the FIG. 3, ultrasound images are available from the video output port of any connected commercial ultrasound system (US1) 92 and are readily acquired by an imaging capture card implemented in the CPU. Captured ultrasound images are directly sent to the display 20 for review and also for guiding near-infra-red imaging formation.

The imaging system 200 is capable of diffusive optical tomography (DOT) and ultrasound functions. These imaging techniques are employed to provide structural information (e.g., size, position, and so forth), as well as functional information (e.g., fluorophore concentration, hemoglobin concentration, oxygen saturation) in the form of digital images of a fluorescing target (e.g., an inclusion) within a turbid medium that can be viewed on a display 20. The methods for imaging employed herein are conducted in three main steps, the first is the location and size of the inclusion 8 using ultrasound, the second is the estimation of the structural parameters of the inclusion 8, and the third is the estimation of the functional parameters of the inclusion 8.

As noted above, once an image of an inclusion is obtained using the ultrasound transducer and the DOT and/or the FDOT, the following algorithms can be used for further determination of the structural and functional features of the inclusion. Three sets of algorithms that are detailed below have been developed, which provide more accurate and reliable optical properties of inclusions of different sizes located at different depths under the skin. As noted above these inclusion sizes and locations are provided by real-time ultrasound images.

The first set of algorithms can be applied to all parts of the body, though it is generally used to segment the imaging volume as breast tissue and chest wall layers and estimate the two layer bulk optical properties instead of one layer property to improve background estimation. In short, it can be used to study breast lesions. This first set of algorithms uses a finite element analysis method to improve the accuracy of reconstructed lesion optical properties, especially when the chestwall is located in less than 1.5 to 2 centimeters depths. The imaging is performed in FEM, which yields improved optical properties of lesions located on top of the chest-wall and closer to the skin surface.

The second set of algorithms reconstructs larger lesions layer by layer in depth instead of the entire volume. This approach significantly overcomes the ill-conditioned problem in inversion and improves the accuracy of reconstructed optical properties.

The third set of algorithms described below reconstructs both optical absorption and scattering simultaneously in a unique approach that does not suffer problems of cross-coupling between estimated absorption and scattering properties.

In another embodiment, the co-registered ultrasound and DOT and/or FDOT can be used a) to identify the chest-wall depth and the approximate tilting angle between the breast tissue and the chest-wall; b) to estimate the bulk optical properties of both breast tissue and chest-wall layer for accurate weight matrix computation using either finite element method or analytical solution; c) to improve the accuracy of reconstructed lesion optical properties, especially when the chest-wall is located in up to about 5 centimeter depths (where depths are measured from the under surface of the skin), specifically about 1.0 to about 4 centimeter depths, and more specifically about 1.5 to about 2 centimeter depths.

In another embodiment, the co-registered ultrasound and DOT and/or FDOT can be used a) to identify the size of the lesion; b) to segment the large lesions of more than 1 centimeters in size into several target layers; c) to improve the reconstruction accuracy of lesion optical properties by imaging target layer by layer, combined target layers and background layers. In yet another embodiment, the co-registered ultrasound and DOT and/or FDOT can be used a) to segment the tissue volume into target and background regions for simultaneously reconstruction of absorption and scattering variations; b) to reconstruct absorption changes using finer and coarse grids and scattering changes using coarse grid only.

Algorithm Set #1:

The first set of algorithms models the breast tissue as a two-layer medium of breast tissue and chest-wall and estimates the optical properties of both layers. The first layer depth and angle of the interface between the two-layers are estimated from the co-registered ultrasound images. The estimated optical properties of both layers are incorporated into the weight matrix calculations. As a result, more accurate target optical properties can be reconstructed.

Since conventional ultrasound is used in pulse-echo reflection geometry, it is desirable to acquire optical measurements with the same geometry. Compared with transmission geometry or ring geometry where the light sources and detectors are deployed on a pair of parallel plates or a ring, the reflection geometry has the advantage of probing reduced breast tissue thickness because patients are scanned in the supine position. Consequently, inclusions closer to the chest wall can be imaged. In general, the breast tissue thickness has been reduced to less than about 3 to about 4 centimeters. However, when the chest wall is present within about 1 to about 1.5 centimeters of the skin surface, the semi-infinite geometry is not a valid assumption for optical measurements and the chest wall underlying the breast tissue affects the optical measurements obtained from distant source-detector pairs. In general, the symmetric location of the contralateral normal breast is chosen as the reference site to minimize the effect of the chest wall.

Figure 7A:
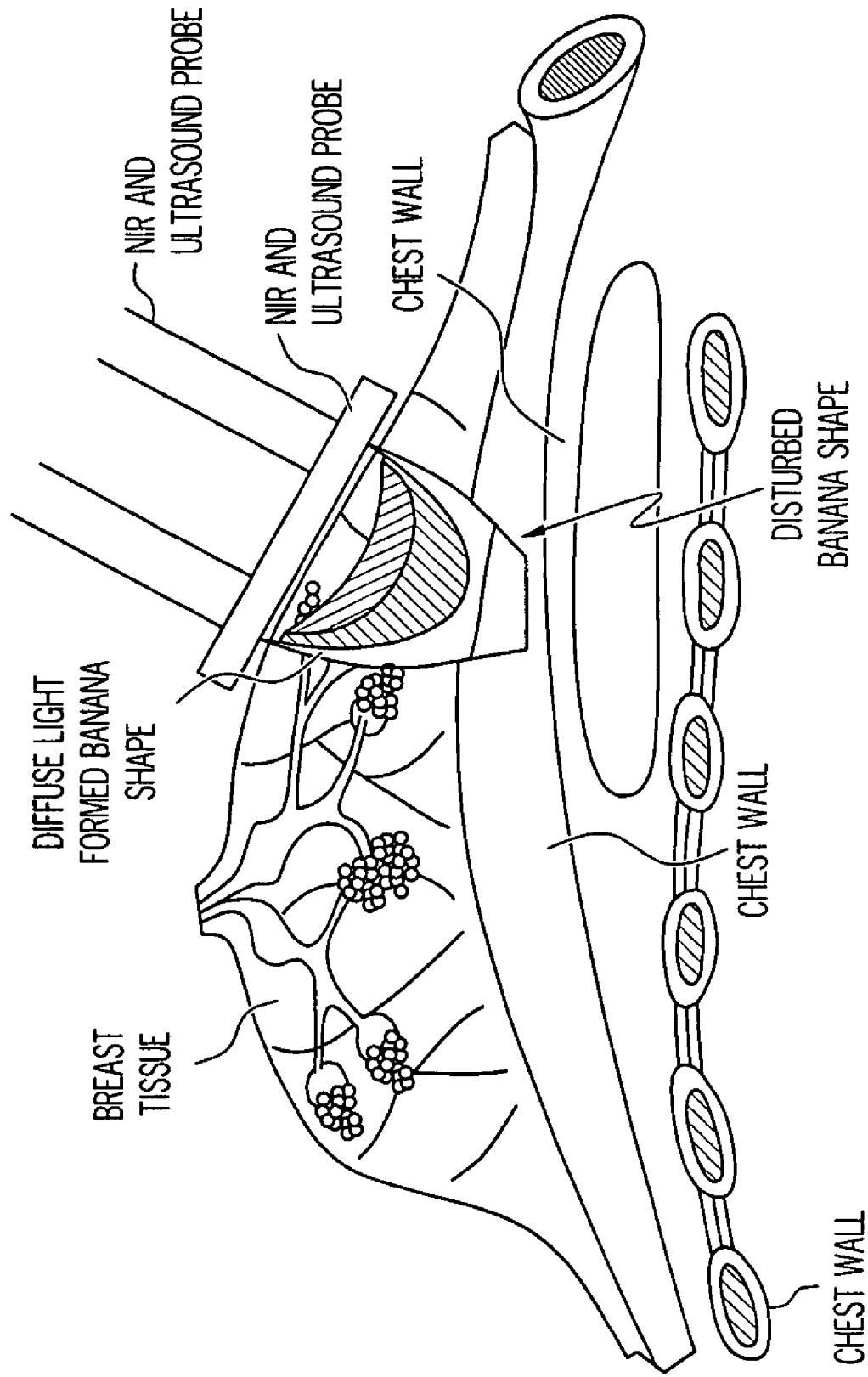
FIG. 7 (a) is a picture illustrating chest-wall induced distortion.
Figure 7B:
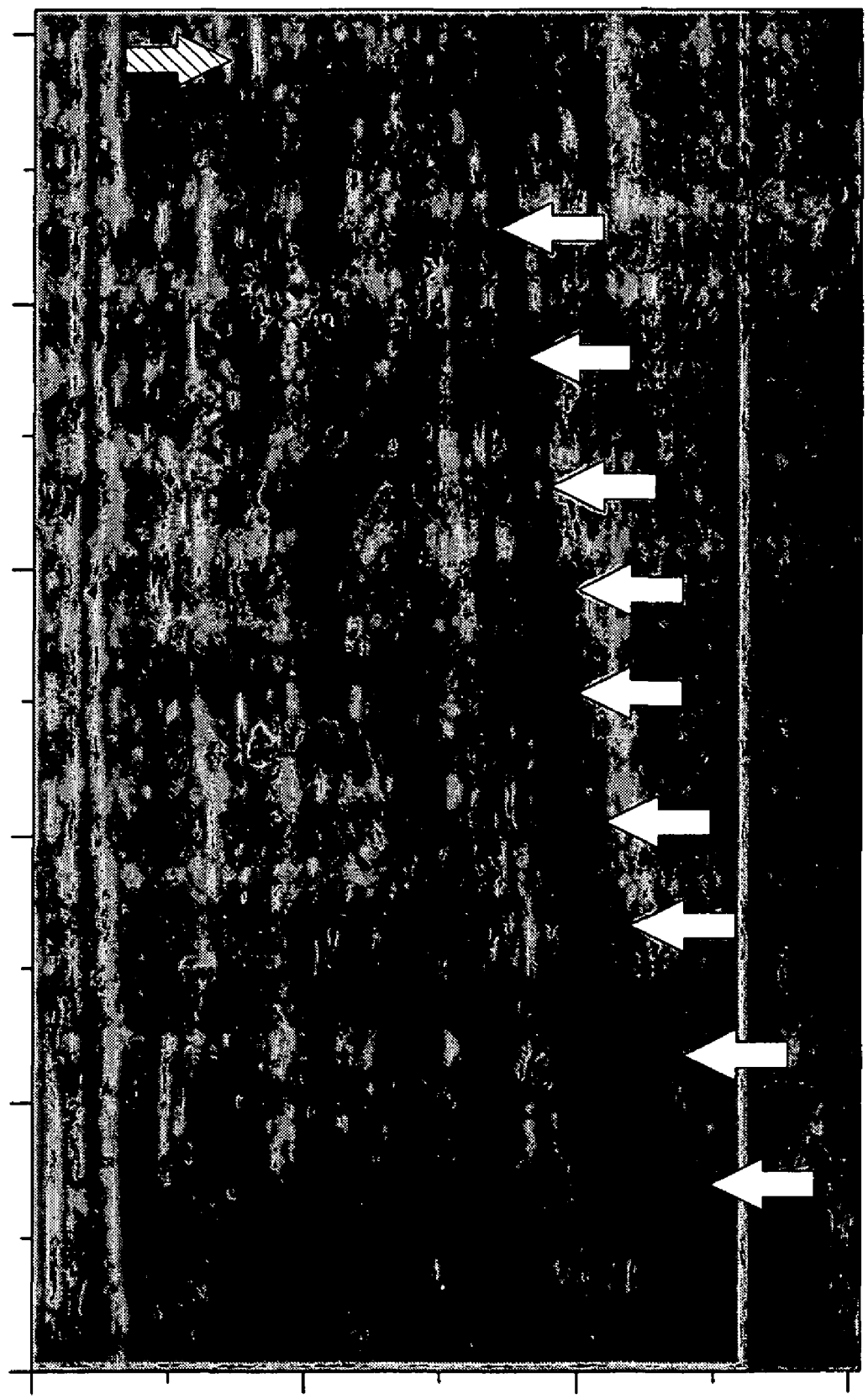
Figure 7C:
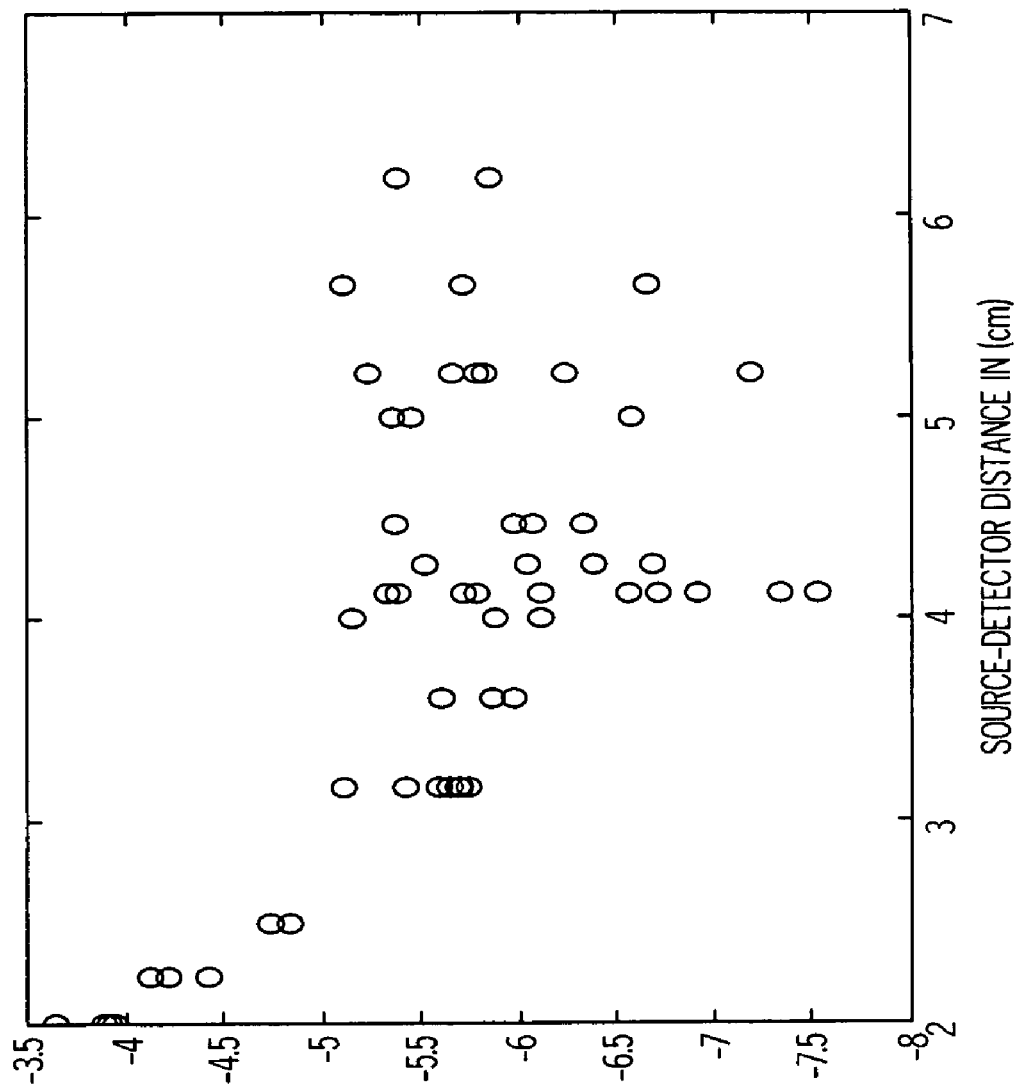

FIG. 7($a$) illustrates the problem when multiple source and detector fibers are deployed on the breast for co-registered imaging. The light reflectance measurements at distant detector positions from the sources comprises mixed signals from both breast tissue and chest wall. Because of the superposition of signals from the breast tissue and the chest wall, the signals are distorted. FIG. 7($b$) is the ultrasound image of the breast where the tilted chest wall marked by white arrows can be seen. FIG. 7($c$) plots the light reflectance (log scale) measured at the surface of the probe versus source-detector separation $\rho$. If the semi-infinite assumption were valid, the plot of reflectance (log scale) versus $\rho$ should be linear. However, as the light penetrates deeper into the tissue and is therefore received by detectors at larger distances from the sources, a deviation from linearity begins to develop which is clearly seen in the plot in FIG. 7($c$).

The distorted distant measurements can be quite complex. In some patients, the measured distant amplitude profiles consist of many random points, while in others, the amplitude profiles bend considerably from expected linear curves. In general, when the amplitude values are low, the phase profiles behave like random variables. As a result, measurements beyond a certain distance must be removed before imaging. Since the depth of chest wall and average breast tissue absorption and scattering coefficients vary from patient to patient, it is difficult to predict the cutoff source-detector distance. As a consequence, the data processing and image reconstruction must be done off-line for each individual patient by examining the data and removing distant measurements.

There are many clinical cases in which the measured amplitude and phase profiles bend considerably from the expected linear curves due to the influence of the shallower chest-wall layer. The resolution between these curved measurements and linearity results a loss of information obtained during the process. In addition, inclusions may be located on top of chest walls, and removing curved measurements may partially remove the perturbation caused by the inclusion.

In order to resolve these issues and to maximize information obtained from the curved path of the light beams, a simple fitting method based on a two-layer model can be employed. This model is used to fit the measured amplitude and phase profiles after filtering out distant source-detector measurements and to estimate the first and the second-layer optical properties, which can be incorporated into the imaging reconstruction. A numerical reconstruction algorithm based on finite element methods (FEM) has been used for solving complex boundary conditions. Summaries of these are provided below.

Figure 8A:
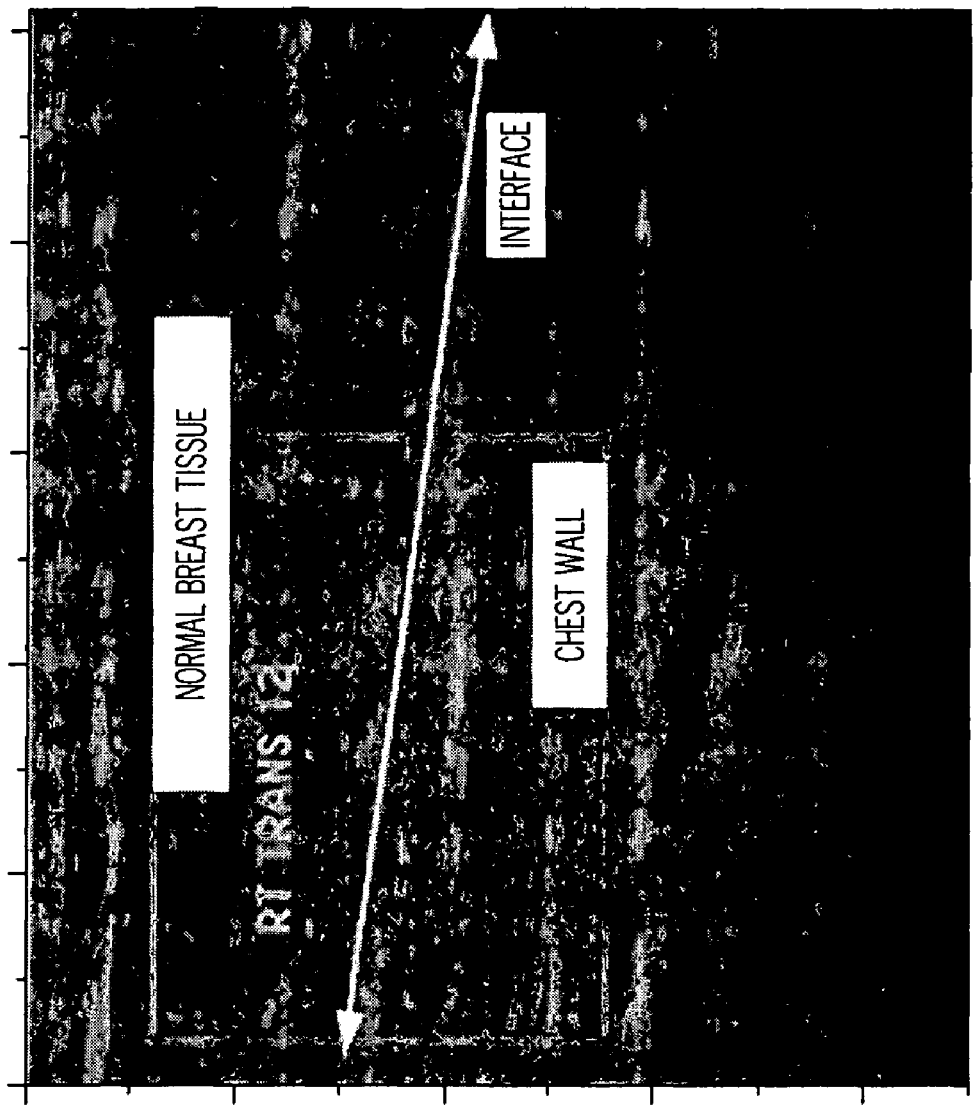
FIG. 8(a) shows a B-scan ultrasound image of a normal breast with tilted chest wall marked.
Figure 8B:
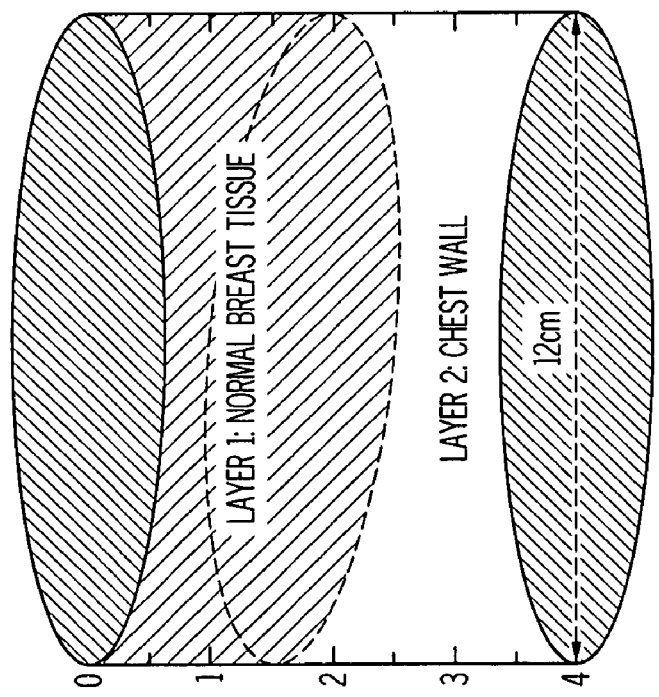
FIG. 8(b) is the corresponding two-layer model generated.

In one embodiment, a 3D cylindrical mesh was generated for forward calculation. The radius of the cylinder was large enough to approximate the semi-infinite geometry, and the height of the cylinder was chosen according to the total imaging volume obtained from co-registered ultrasound images. A smooth surface was used to model the tissue and the chest-wall interface. The chest-wall tilting angle $\alpha$ with respect to the probe and the tissue-chest interface located in depth D was determined by the co-registered ultrasound images. FIGS. 8($a$) and ($b$) gives an example of the two-layer model configuration. FIG. 8($a$) shows a B-scan ultrasound image of a normal breast with tilted chest wall marked and FIG. 8($b$) is the corresponding two-layer model generated.

Bulk absorption and reduced scattering coefficients for both first and second layers were used to estimate the photon density: $\phi\phi(r,\omega)=f(\mu_{a1},\mu'_{s1},\mu_{a2},\mu'_{s2})$, where $\mu_{a1}$, $\mu_{a2}$, $\mu'_{s1}$, and $\mu'_{s2}$ are absorption and reduced scattering coefficients of first and second layers, respectively. Absorption coefficients have the subscript "a", while scattering coefficients have the subscript "s", where the subscript "1" represents the first layer, the subscript "2" represents the second layer, and the superscript (') stands for the reduced scattering coefficient. To find the best fitting results, reasonably accurate bulk absorption and scattering coefficients $\mu_{a10}$ and $\mu'_{s10}$ of the first layer were first obtained by fitting the measurements from normal breasts after removing distorted distant measurements. The initial absorption and scattering coefficients $\mu_{a20}$ and $\mu'_{s20}$ of the second layer were set to be the same as those of the first layer. Measurements from a homogeneous Intralipid solution, which has the same optical properties as the fitted bulk values of the first layer, were used as $\phi_0(r,\omega)$. Intralipid solution is a light scattering medium used in photodynamic therapy in both phantom studies and to obtain optimum light distributions from clinical light delivery systems. When the initial estimates of $\phi_0(r,\omega)$, $\mu_{a10}$, $\mu_{a20}$, $\mu'_{s10}$, and $\mu'_{s20}$, have been obtained, the conjugate gradient method was applied to find the best fitted optical properties of the two-layer model by minimizing the least-square objective function given as $\min\|\phi(r,\omega)-\phi_0(r,\omega)\|^2$.

The forward Jacobian weight matrix $$W_{ij} = \left[\frac{\partial \phi_{ij}}{\partial \mu_{aj}}, \frac{\partial \phi_{ij}}{\partial D_j}\right],$$

which relates the photon density perturbation at detector i and imaging voxel j with absorption coefficient change $\Delta\mu_{aj}$ and diffusion coefficient change $\Delta D_j$, is calculated by using the bulk optical properties simulated from the two-layer layer model and given in equation (1) as:

$$[W_{ij}] = \begin{bmatrix} \frac{\partial \phi_{11}}{\partial \mu_{a1}} & \cdots & \frac{\partial \phi_{1L}}{\partial \mu_{aL}} & \frac{\partial \phi_{11}}{\partial D_1} & \cdots & \frac{\partial \phi_{1L}}{\partial D_L} \\ \frac{\partial \phi_{21}}{\partial \mu_{a1}} & \cdots & \frac{\partial \phi_{2L}}{\partial \mu_{aL}} & \frac{\partial \phi_{21}}{\partial D_1} & \cdots & \frac{\partial \phi_{2L}}{\partial D_L} \\ \vdots & \ddots & \vdots & \vdots & \ddots & \vdots \\ \frac{\partial \phi_{M1}}{\partial \mu_{a1}} & \cdots & \frac{\partial \phi_{ML}}{\partial \mu_{aL}} & \frac{\partial \phi_{M1}}{\partial D_1} & \cdots & \frac{\partial \phi_{ML}}{\partial D_L} \end{bmatrix}, \quad (1)$$

where M is the total number of detector readings and L is the total number of imaging voxels.

Algorithm Set #2

This algorithm provides imaging reconstruction based on a two-layer model with the layer-structure identified by co-registered ultrasound.

For a large tumor that is larger than two layers in depth (more than 1 cm in general), wherein each layer is considered to be about 0.5 centimeter, the performance of the dual-zone mesh based inversion is degraded because of the increased number of fine-mesh grids with unknown optical properties in the region of interest. As a result, the weight matrix is more ill-conditioned and underdetermined for inversion. The reconstruction of large inclusions is improved by implementing the dual-zone mesh one layer (in depth) at a time, combining the target layers, and the background layers to obtain the final absorption images.

In the dual-zone mesh based image reconstruction, two types of voxels, a first voxel and a second voxel, are used. The first voxels lie within the boundary of the inclusion, while the second voxels lie outside the boundary of the inclusion (e.g., the background). Those voxels within the boundary of the inclusion, are finer than those located outside of the boundary of the inclusion. Within the boundary of the inclusion, each first voxel has a volume of about 0.1×0.1×0.1 cubic centimeter (cm$^3$) to about 1×1×1 cm$^3$, specifically about 0.2×0.2×0.2 cm$^3$ to about 0.8×0.8×0.8 cm$^3$, to about 0.3×0.3×0.3 cm$^3$ to about 0.6×0.6×0.6 cm$^3$. Within the boundary of the inclusion, each voxel has a preferred volume of about 0.5×0.5×0.5 cm$^3$.

Outside the boundary of the inclusion, each second voxel has a volume of about 0.2×0.2×0.2 cm$^3$ to about 2.0×2.0×2.0 cm$^3$, specifically about 1.2×1.2×1.2 cm$^3$ to about 1.8×1.8×1.8 cm$^3$, and more specifically about 1.3×1.3×1.3 to about 1.7×1.7×1.7 cm$^3$. Outside the boundary of the inclusion (e.g., for imaging the tissue surrounding the inclusion), each voxel has a preferred volume of about 1.5×1.5×1.5 (cm$^3$). The total imaging volume is chosen to be about 15×15×10 cm$^3$, specifically about 12×12×8 cm$^3$, and more specifically about 9×9×4 cm$^3$.

The ratio of voxel sizes inside the boundary of the inclusion (inclusion region) to that outside the boundary of the inclusion (background region) is about 3% to about 90%, specifically about 8% to about 50%, more specifically about 10% to about 30%, and even more specifically about 12 to about 20%.

Figure 9:
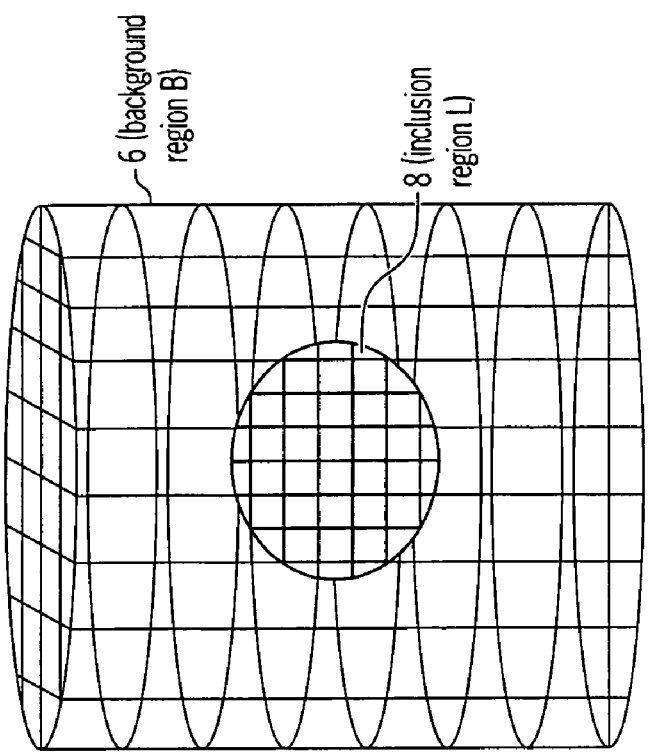
FIG. 9 is an exemplary depiction of the dual-zone mesh based image reconstruction, the entire tissue volume is segmented based on co-registered ultrasound images into an inclusion region, L (region of interest, ROI), and a background region, B.

With reference now to the FIG. 9, in the dual-zone mesh based image reconstruction, the entire tissue volume is segmented based on co-registered ultrasound images into an inclusion region, L (region of interest, ROI), and a background region, B. A modified Born approximation is used to relate the scattered field $U_{sd}(r_{si}, r_{di}, \omega)$ measured at the source (s) and detector (d) pair i to absorption variations $\Delta\mu_a(r')$ in each volume element of the two regions within the sample. The matrix form of the image reconstruction is given by the equation (2)

$$[U_{sd}]_{M\times 1} = [W_L, W_B]_{M\times N} \times [M_L, M_B]^T_{N\times 1} \quad (2)$$

where $W_L$ and $W_B$ are weight matrices for the inclusion and background regions, respectively.

$$[M_L] = \left[ \int_{1_L} \Delta\mu_a(r')d^3 r', \ldots \int_{N_L} \Delta\mu_a(r')d^3 r' \right]$$

and $$[M_B] = \left[ \int_{1_B} \Delta\mu_a(r')d^3 r', \ldots \int_{N_B} \Delta\mu_a(r')d^3 r' \right]$$

are the total absorption distributions of inclusion and background regions, respectively. The weight matrices are calculated based on the background absorption coefficient $\bar{\mu}_a$ and reduced scattering coefficient $\bar{\mu}'_s$ measurements obtained from the normal contralateral breast.

If large inclusions occupy more than one layer in depth, we divide the region of interest (ROI) into N zones in N layers denoted as ROI#1, ROI#2, . . . ROI#N respectively. The above dual-zone reconstruction algorithm will be used one layer at a time and a total of N steps is therefore needed to reconstruct the entire image.

Mathematically, the new reconstruction procedures can be written as shown in the Equations (3), (4) and (5):

Step 1:

$$[U_{sd}]_{M\times 1} = [W_{L(ROI\#1)}, W_{B_1}, W_{B_1(other\text{-}target\text{-}layers)}, W_{B(BG\text{-}layers)}] \times [M_{L(ROI\#1)}, M_{B_1}, M_{B_1(other\text{-}target\text{-}layers)}, M_{B(BG\text{-}layers)}]^T \quad (3)$$

Step 2:

$$[U_{sd}]_{M\times 1} = [W_{L(ROI\#2)}, W_{B_2}, W_{B_2(other\text{-}target\text{-}layers)}, W_{B(BG\text{-}layers)}] \times [M_{L(ROI\#2)}, M_{B_2}, M_{B_2(other\text{-}target\text{-}layers)}, M_{B(BG\text{-}layers)}]^T \quad (4)$$

. . .

Step N:

$$[U_{sd}]_{M\times 1} = [W_{L(ROI\#N)}, W_{B_N}, W_{B_N(other\text{-}target\text{-}layers)}, W_{B(BG\text{-}layers)}] \times [M_{L(ROI\#2)}, M_{B_N}, M_{B_N(other\text{-}target\text{-}layers)}, M_{B(BG\text{-}layers)}]^T \quad (5)$$

where $W_{L(ROI\#1)}$, $W_{L(ROI\#2)}$, . . . , $W_{L(ROI\#N)}$, are weight matrices of ROI#1, #2 and #N respectively, and $W_{B_1}$, $W_{B_2}$, . . . , $W_{B_N}$ are weight matrices of corresponding background regions in the same depth layer. $W_{B_1(other\text{-}target\text{-}layers)}$, $W_{B_2(other\text{-}target\text{-}layers)}$, $W_{B_N(other\text{-}target\text{-}layers)}$, are weight matrices of other target layers excluding the corresponding ROI# target layer, and $W_{B(BG\text{-}layers)}$ is the weight matrix of common background layers respectively. After N steps of imaging reconstruction, the total absorption matrix can be obtained as $[M_{L(ROI\#1)}, M_{B_1}, M_{L(ROI\#2)}, M_{B_2}, \ldots M_{L(ROI\#N)}, M_{B_N}, M_{BG(BG\text{-}layers)}]$, and the absorption distribution can be computed by dividing the corresponding voxel size in ROIs and in the background regions.

In each reconstruction step, only one layer with finer mesh or ROI # is reconstructed and the other target layers are treated as background. Therefore, the total number of imaging voxels with unknown optical properties is always comparable with the total measurements and the inversion is well-conditioned.

Algorithm Set #3

Previously conducted experiments, have shown that when optical absorption changes as well as scattering changes are reconstructed, the simultaneous reconstruction of both absorption and scattering coefficients of a target may result in a cross-coupling between the reconstructed absorption and scattering coefficients and this results in a reduced accuracy of the target absorption estimation. The algorithm described below simultaneously reconstructs the target and background absorption and scattering changes. However, the scattering changes are reconstructed in coarse mesh to significantly reduce the total number of voxels with unknown optical properties and to improve the accuracy of reconstructed absorption coefficients. The absorption estimation is directly related to the functional parameter calculation, such as hemoglobin concentration and blood oxygenation.

In the dual-zone mesh based image reconstruction, the entire tissue volume is segmented based on co-registered ultrasound images into a lesion region, L (region of interest, ROI), and a background region, B. A modified Born approximation is used to relate the scattered field $U_{sd}(r_{si}, r_{di}, \omega)$ measured at the source (s) and detector (d) pair i to absorption variations $\Delta\mu_a(r')$ in each volume element of two regions within the sample. The scattered field $U_{sd}(r_{si},r_{di},\omega)$ measured at the source (s) and detector (d) pair i is also related to the diffusion coefficient variations $\Delta D(r')$ in the target and background. However, both target and background scattering changes are reconstructed in a coarse grid to significantly reduce the number of unknowns and improve the accuracy of reconstructed optical absorption changes. The matrix form of image reconstruction is given by the Equation (6)

$$[U_{sd}]_{M\times 1} = [W_L, W_B, W_S]_{M\times N} \times [M_L, M_B, M_S]^T_{N\times 1} \quad (6)$$

where $W_L$ and $W_B$ are absorption weight matrices for lesion and background regions, respectively. $W_S$ is the scattering weight matrix for the entire imaging volume.

$$[M_L] = \left[ \int_{1_L} \Delta\mu_a(r')d^3r', \ldots \int_{N_L} \Delta\mu_a(r')d^3r' \right]$$

and $$[M_B] = \left[ \int_{1_B} \Delta\mu_a(r')d^3r', \ldots \int_{N_B} \Delta\mu_a(r')d^3r' \right]$$

are the total absorption distributions of inclusion and background regions, respectively.

$$[M_S] = \left[ \int_1 \Delta D(r')d^3r', \ldots \int_N \Delta D(r')d^3r' \right]$$

is the total diffusion distribution of the entire tissue volume segmented with the coarse grid. The weight matrices are calculated based on the background absorption coefficient $\bar{\mu}_a$ and reduced scattering coefficient $\bar{\mu}'_s$ measurements obtained from the normal contralateral breast.

By assuming that the major chromophores are deoxygenated (deoxyHb) and oxygenated (oxyHb) hemoglobin in the wavelength range studied, a direct estimate of the total hemoglobin concentration totalHb(r')=deoxyHb(r')+oxyHb(r') and oxygenation saturation $$Y\% = \frac{oxyHb(r')}{oxyHb(r') + deoxy(r')} 100\%$$

can be obtained from the Equation (7) and (8):

$$totalHb(r') = \frac{1}{\Delta}\left\{\left\{\varepsilon_{HbO_2}^{\lambda_2} - \varepsilon_{Hb}^{\lambda_2}\right\}\mu_a^{\lambda_1}(r') + \left\{\varepsilon_{Hb}^{\lambda_1} - \varepsilon_{HbO_2}^{\lambda_1}\right\}\mu_a^{\lambda_2}(r')\right\} \quad (7)$$

$$= weight(\lambda_1)\mu_a^{\lambda_1}(r') + weight(\lambda_2)\mu_a^{\lambda_2}(r') \quad (8)$$

$$\text{and } Y\% = \frac{-\varepsilon_{Hb}^{\lambda_2}\frac{\mu_a^{\lambda_1}(r')}{\mu_a^{\lambda_2}(r')} + \varepsilon_{Hb}^{\lambda_1}}{(\varepsilon_{HbO_2}^{\lambda_2} - \varepsilon_{Hb}^{\lambda_2})\frac{\mu_a^{\lambda_1}(r')}{\mu_a^{\lambda_2}(r')} - (\varepsilon_{HbO_2}^{\lambda_1} - \varepsilon_{Hb}^{\lambda_1})} 100\%, \quad (9)$$

where $\mu_a^{\lambda_1}(r')$ and $\mu_a^{\lambda_2}(r')$ are optical absorption at volume element r' and $\Delta = \varepsilon_{Hb}^{\lambda_1}\varepsilon_{HbO_2}^{\lambda_2} - \varepsilon_{HbO_2}^{\lambda_1}\varepsilon_{Hb}^{\lambda_2}$.

In principle, any two wavelengths in the NM window can be used to compute the total hemoglobin concentration from equation (7). However, positive weights of $\mu_a^{\lambda_1}(r')$ and $\mu_a^{\lambda_2}(r')$ in equation (7) ensure that the estimated total hemoglobin concentration at each voxel is positive. This is useful in the background region where the absorption coefficients are small and consequently the relative estimation errors of absorption coefficients are larger than those in the lesion region.

Figure 10:
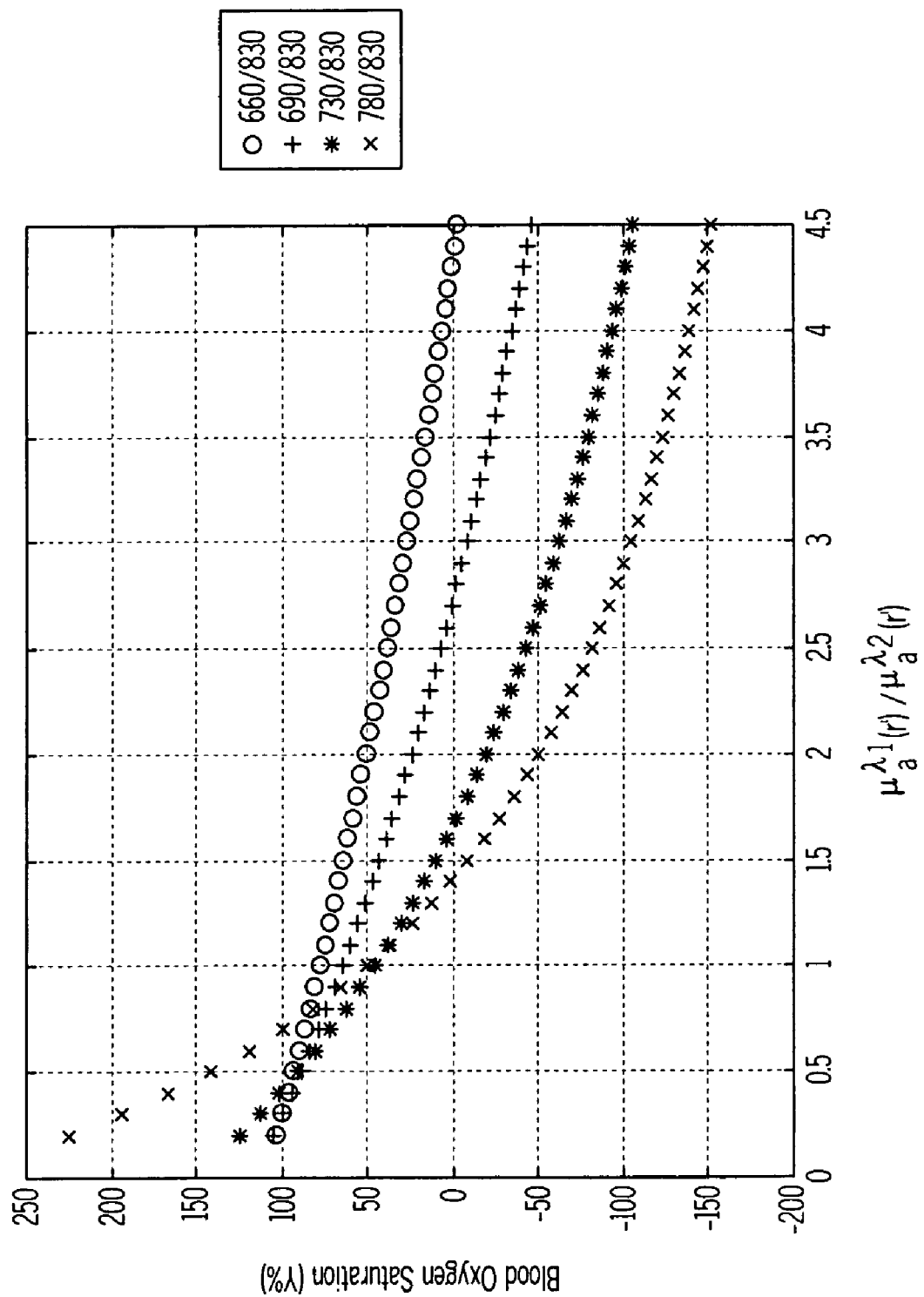
FIG. 10 is a plot showing the Y % versus the ratio for 4 wavelength pairs (660 nm/830 nm, 690 nm/830 nm, 730 inn/830 nm and 780 nm/830 nm).

Similarly, any two wavelengths in the NIR window can be used to compute the oxygenation saturation from equation (4). However, the sensitivity of Y % to ratio $$\frac{\mu_a^{\lambda_1}(r')}{\mu_a^{\lambda_2}(r')}$$

is significantly different for different wavelength pairs. FIG. 10 is a plot showing the Y % versus the ratio for four wavelength pairs (660/830 nm, 690/830 nm, 730/830 nm and 780/830 nm). For the wavelength pair 660/830 nm, the Y % lies in the physiological range between 0.3 and 4.4

$$\left(\text{e.g., } 0.3 < \frac{\mu_a^{\lambda_1}(r')}{\mu_a^{\lambda_2}(r')} < 4.4\right).$$

However, for the wavelength pair of (780 nm and 830 nm), the Y % is greater than 100% for $$\frac{\mu_a^{\lambda_1}(r')}{\mu_a^{\lambda_2}(r')}$$

is less than or equal to about 0.7 and reduces quickly to zero for a ratio greater than or equal to about 1.4. Any estimation error on $\mu_a^{\lambda_1}(r')$ and $\mu_a^{\lambda_2}(r')$ can cause the estimated Y % to fall outside the expected physiological range, particularly when the (r') and $\mu_a^{\lambda_2}(r')$ are small in the background tissue regions. For example, the estimated absorption coefficients from normal breasts are within 0.01 to 0.06 cm$^{-1}$ at 780 nm and 0.02 to 0.07 cm$^{-1}$ at 830 nm. The computed blood oxygen saturation values using these background absorption coefficients may exceed 100%. Considering both factors, robust estimation of total hemoglobin concentration favors the wavelength pair of 780 nm and 830 nm whereas blood oxygenation saturation estimation is best for the wavelength pair of 660 nm and 830 nm.

With the real-time co-registered ultrasound guidance on inclusion size and location, an optimal light modulation frequency can be selected which may yield more accurate estimates of lesion angiogenesis and hypoxia. As will be shown in the examples below, large and small absorbers of both high and low optical contrasts have shown that a high modulation frequency, such as 350 MHz, is preferable for probing small lesions closer to the surface while a low modulation frequency, such as 50 MHz, is desirable for imaging deeper and larger lesions.

Data from many clinical cases have shown that NIR measurements at 660 nm are subject to higher background light scattering because the reduced scattering coefficient $\mu'_s = a\lambda^{-b}$ increases with the decreased wavelength. In this prototype system, we have chosen the wavelength pair of (690 nm, 830 nm) for blood oxygen estimation. 690 nm is the longest wavelength in the visible range and laser diodes at this wavelength are available. As a result, three typical wavelengths of 690 nm, 780 nm, and 830 nm are implemented in our system for estimation of total hemoglobin concentration and blood oxygen saturation.

The present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

The invention is further illustrated by the following non-limiting examples.

EXAMPLES

Example 1

This example was conducted to validate the accuracy of the fitting method for estimating the two-layer optical properties. To well-condition the inversion, a dual-zone mesh method with a target region (region of interest (ROI)) identified by co-registered ultrasound and a background region for weight matrix calculation was used. For simulation and phantom experiments, the imaging voxel size within ROI was chosen as 0.25 cm×0.25 cm×0.5 cm, the pixel size outside of ROI was chosen as 0.5 cm×0.5 cm×1 cm. For clinical cases, the inclusion boundary was not well identified in general and the ROI was chosen to be much larger than the inclusion boundary measured by ultrasound. Because of the dual-mesh scheme, the total number of unknown voxels was significantly reduced.

Imaging experiments were performed with simulated targets imbedded in a two-layer media and reconstructed with the corresponding layered-structure using a semi-infinite model. In these imaging experiments performed with simulated targets, the chest wall layers were placed at depth of 1.3 cm, 1.6 cm and 2.0 cm, respectively. The first layer absorption and scattering parameters ($\mu_{a1}$ and $\mu'_{s1}$) were kept as 0.02 cm$^{-1}$ and 6 cm$^{-1}$ respectively, and the second layer absorption and scattering parameters ($\mu_{a2}$ and $\mu'_{s2}$) were kept at 0.08 cm$^{-1}$ and 10 cm$^{-1}$, respectively.

Figure 11:
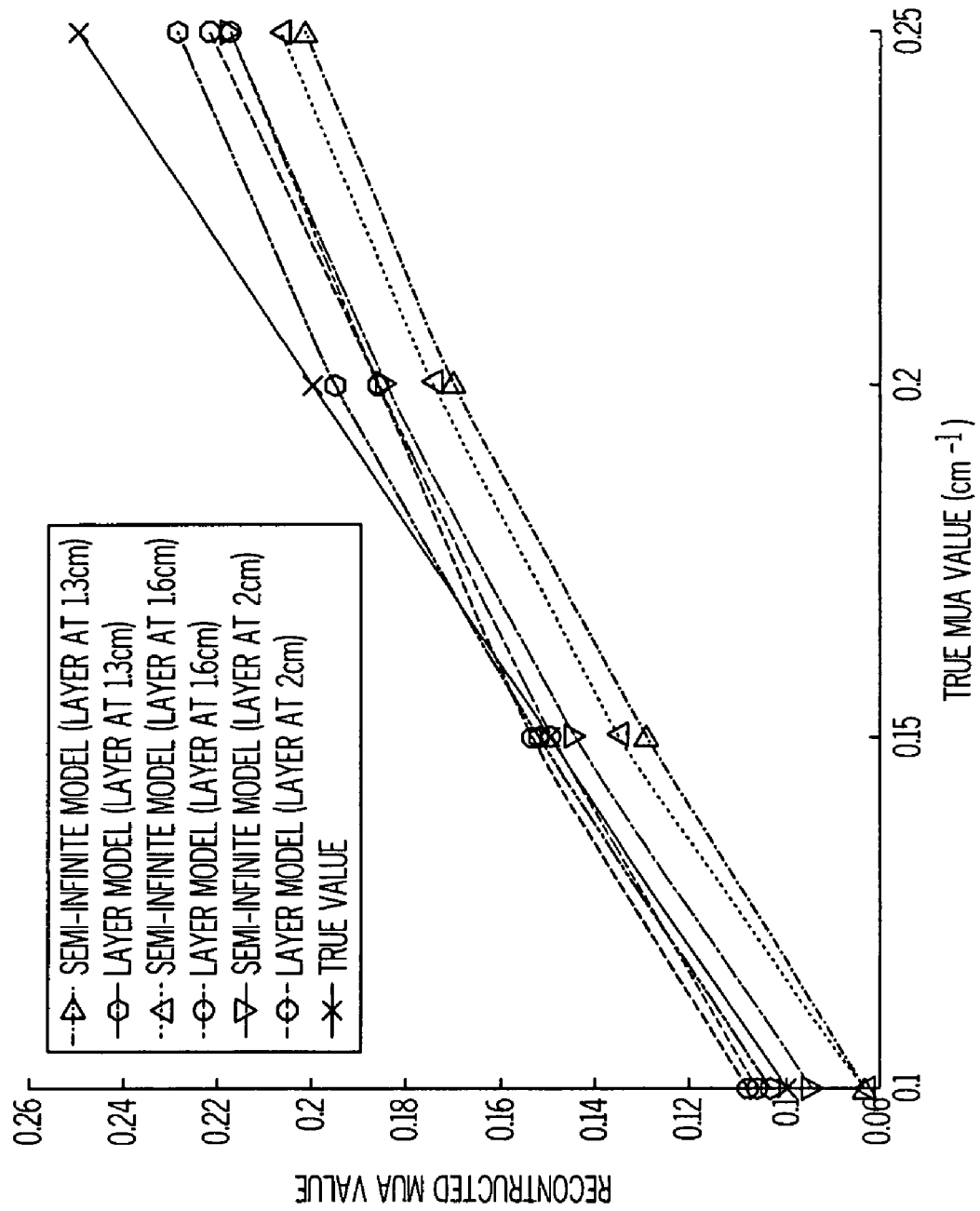
FIG. 11 is a plot showing a reconstructed target optical absorption versus true values; the circles are results obtained from a two-layer model and triangles are from a semi-infinite model.
Figure 12B:
FIG. 12 (a) depicts a B-scan ultrasound image of a two-layer tissue model. First layer is made of the homogeneous 0.5% Intralipid solution, and the second layer is made of a silicone tissue model.
Figure 12A:
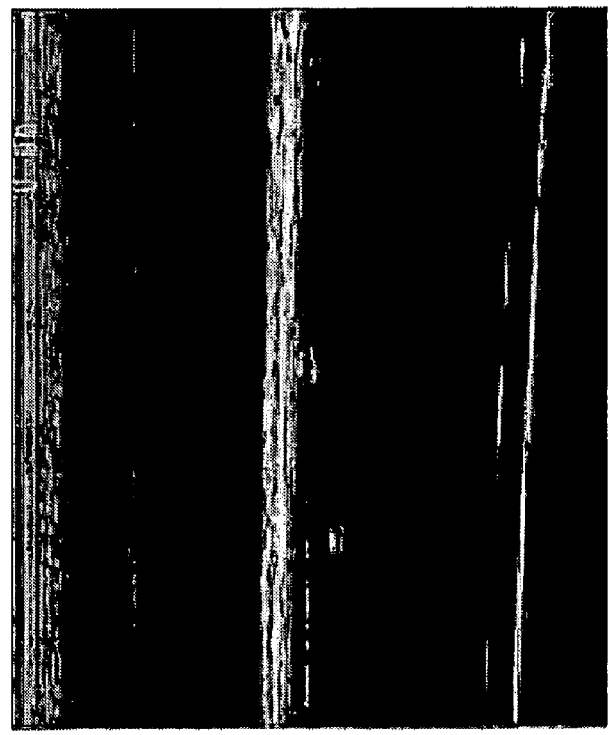
Figure 12C:
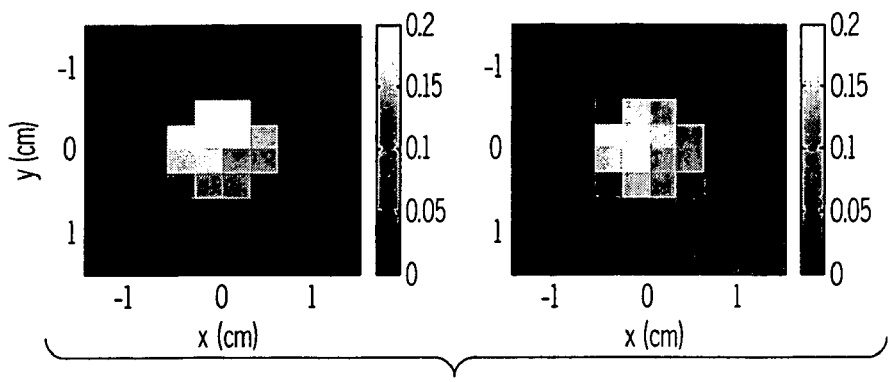
Figure 12D:
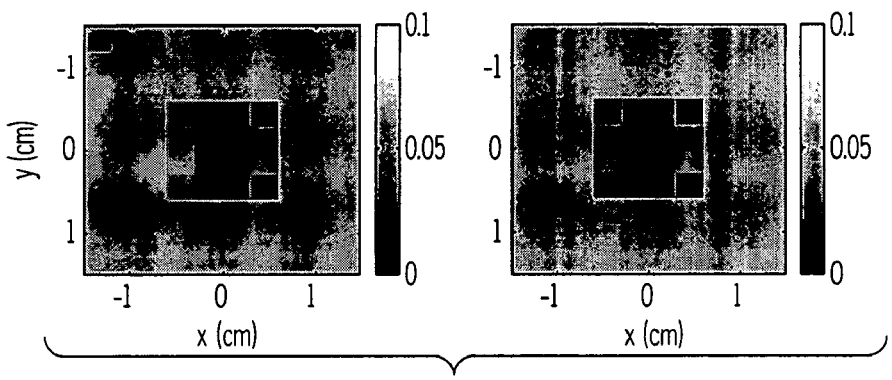
Figure 12E:
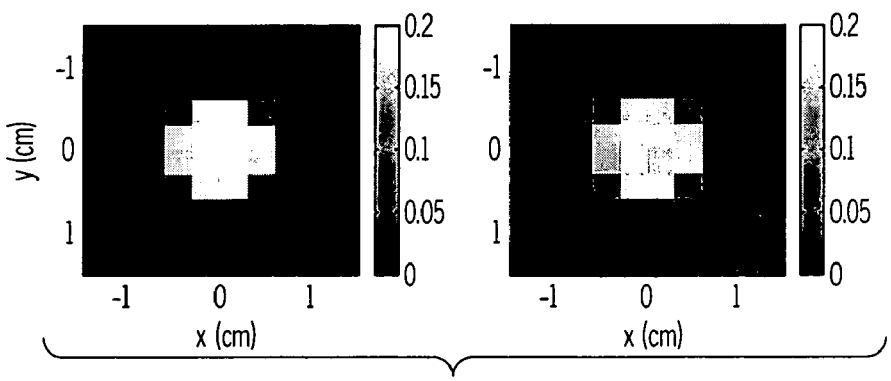
Figure 12F:
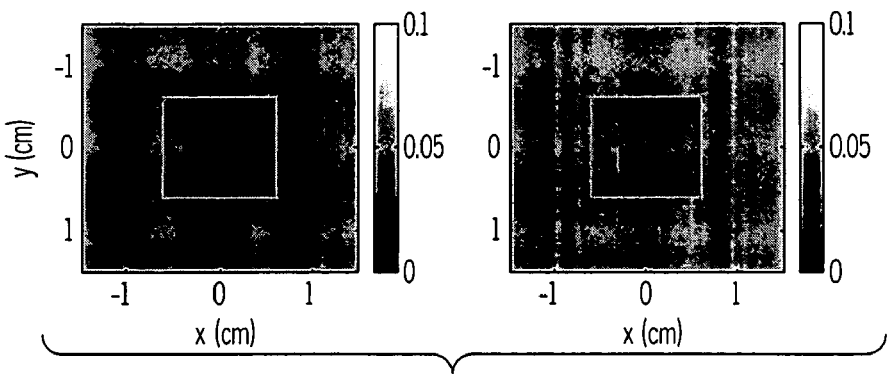
Figure 13B:
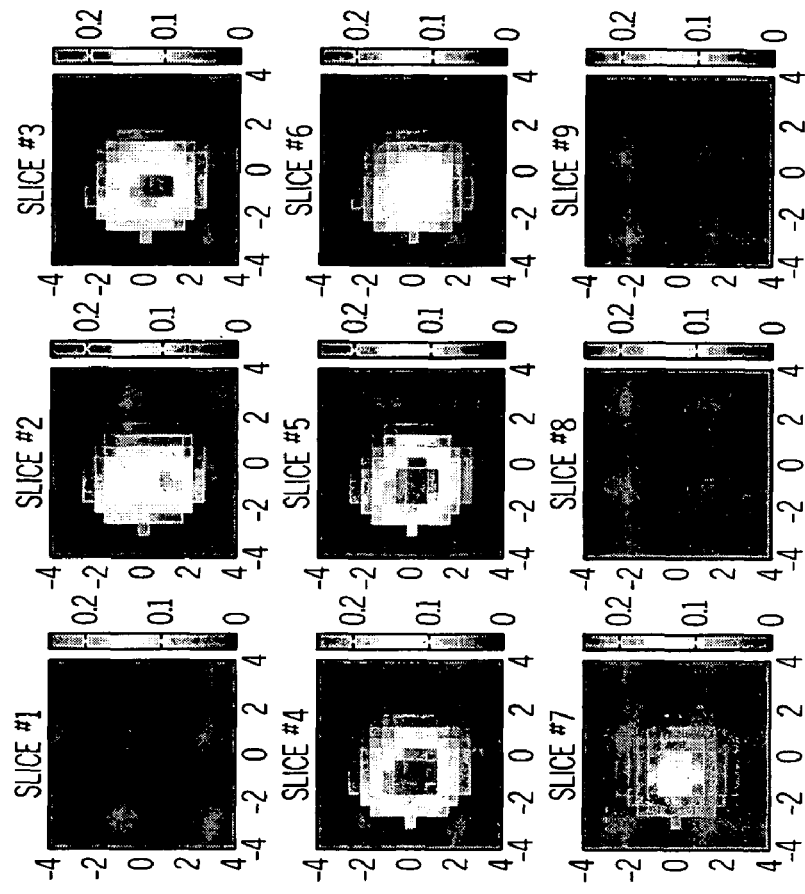
FIG. 13 depicts the co-registered ultrasound images (first column) and reconstructed optical absorption maps of the 3-cm-diameter high-contrast absorber obtained at 50 MHz (second column), 140 MHz (third column), and 350 MHz (fourth column) modulation frequencies.
Figure 13A:
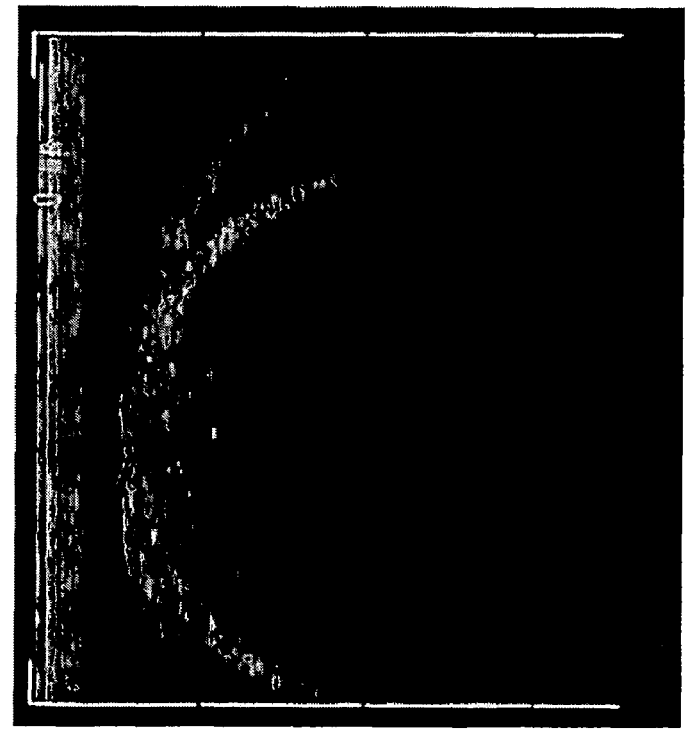
Figures 13C, 13D:
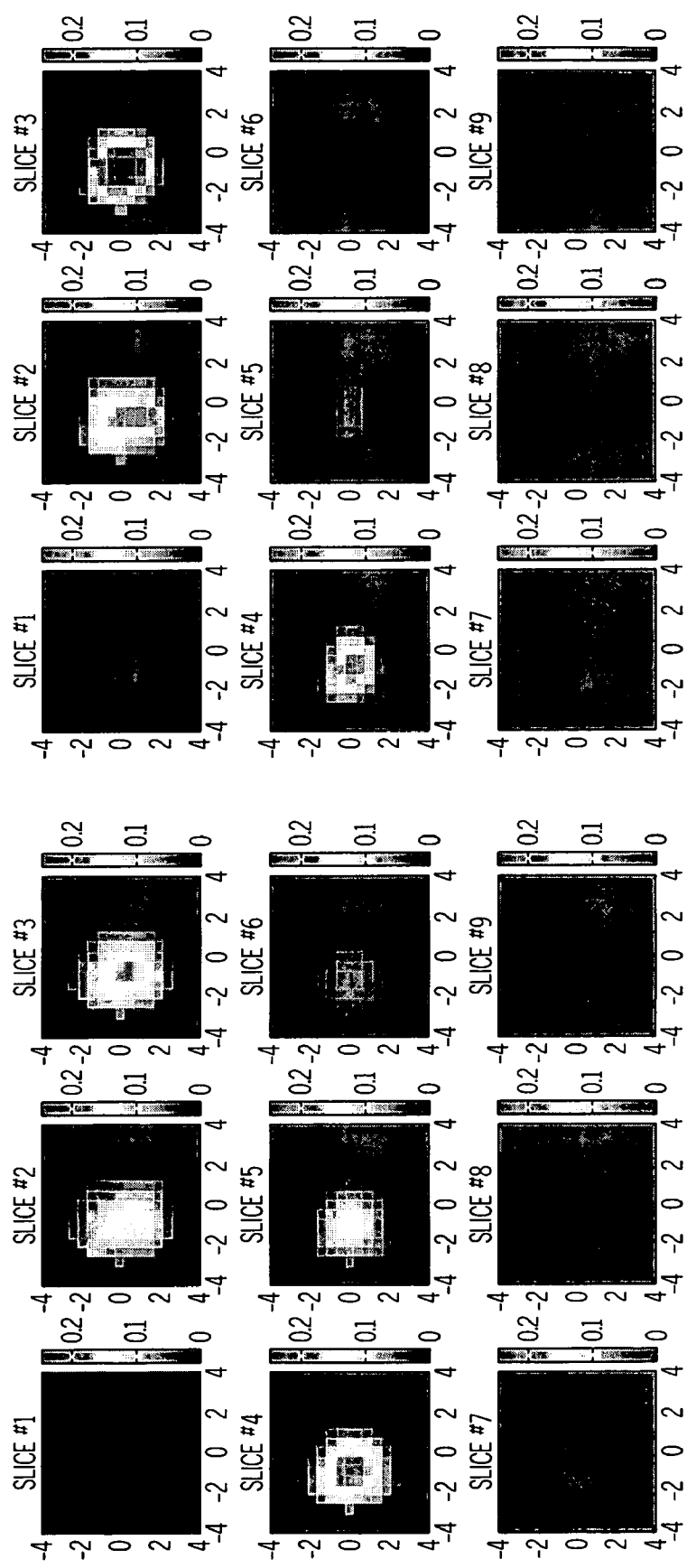
Figure 13F:
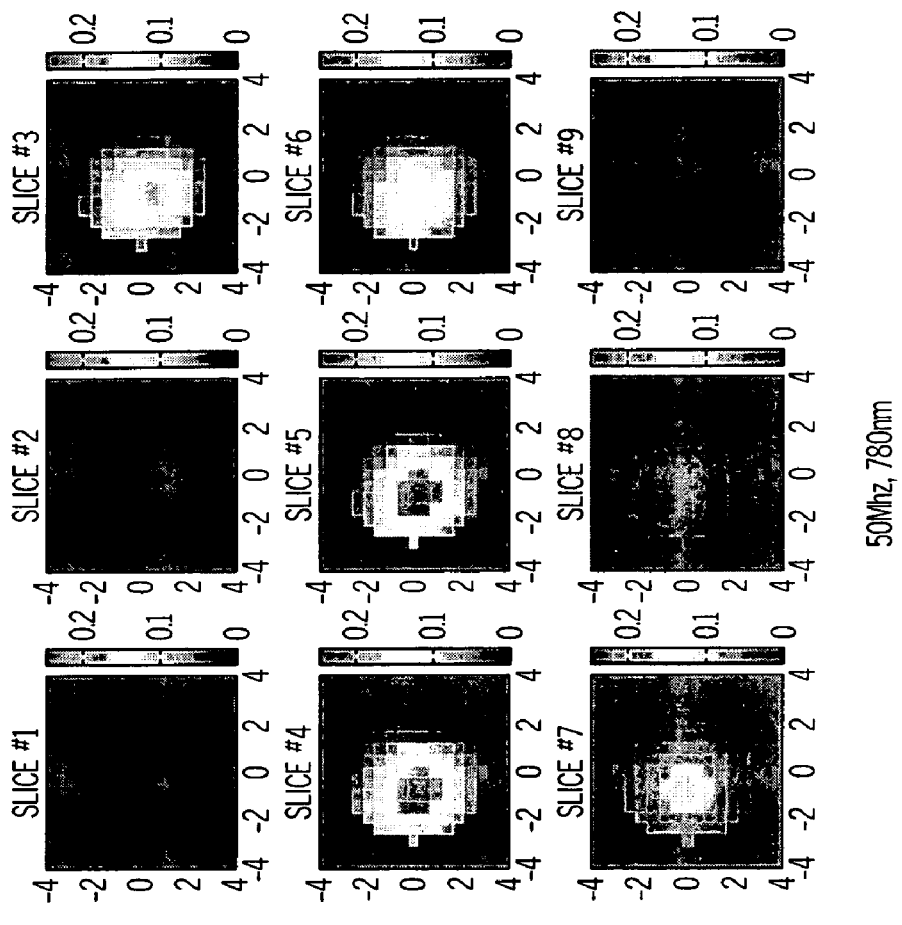
Figure 13E:
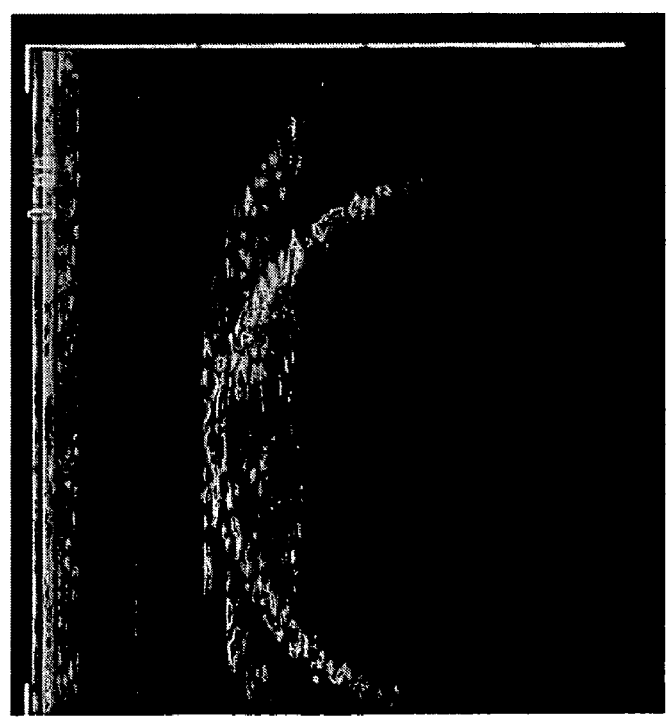
Figure 13J:
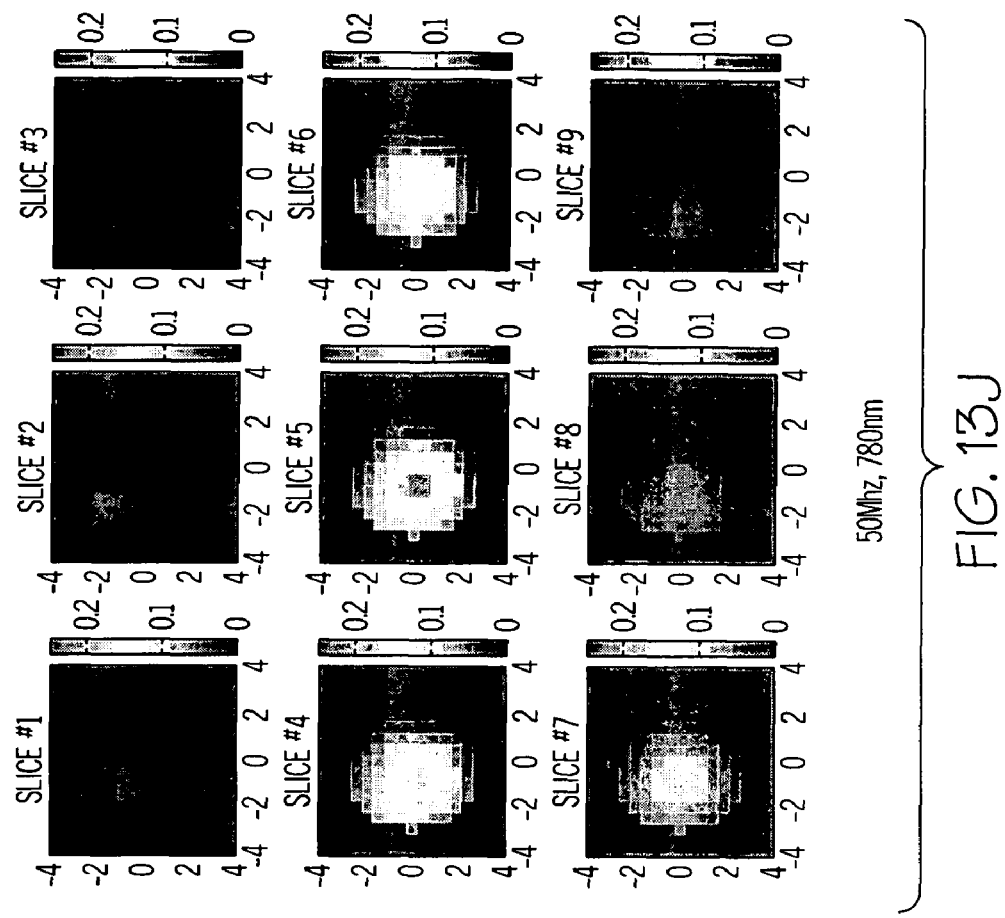
Figure 13I:
Figure 13N:
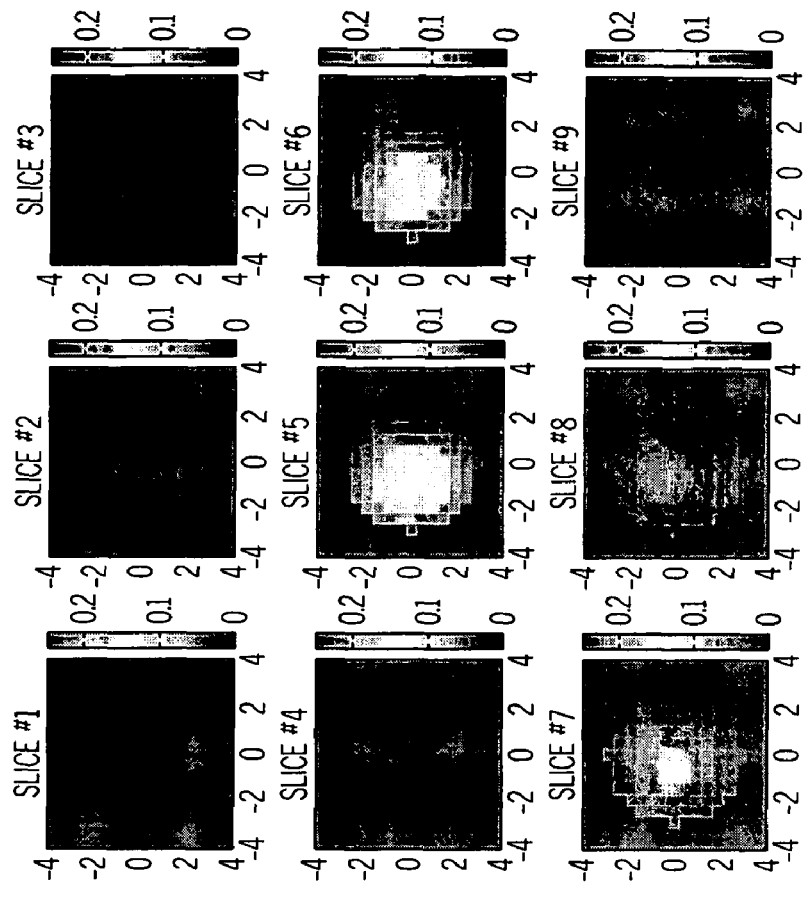
Figure 13M:
Figures 13O, 13P:
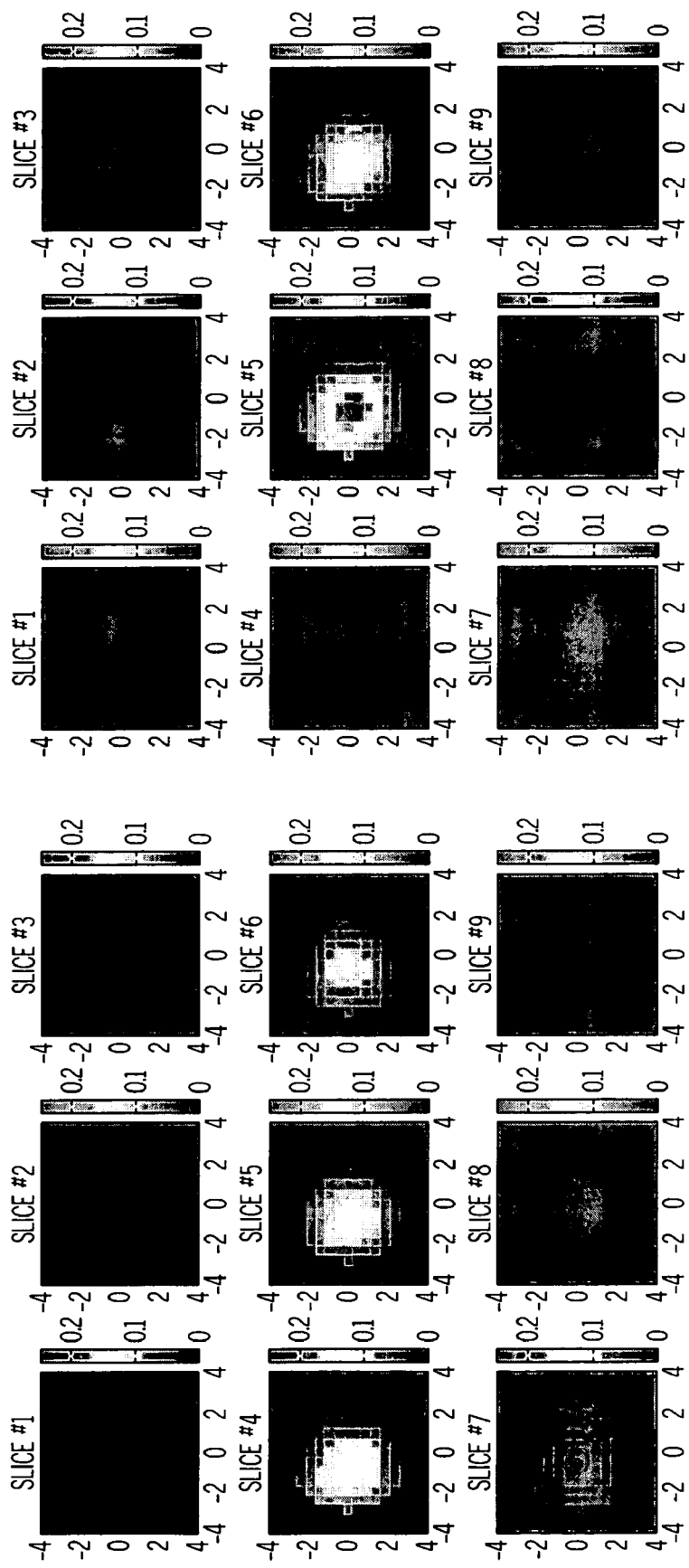
Figures 14C, 14D:
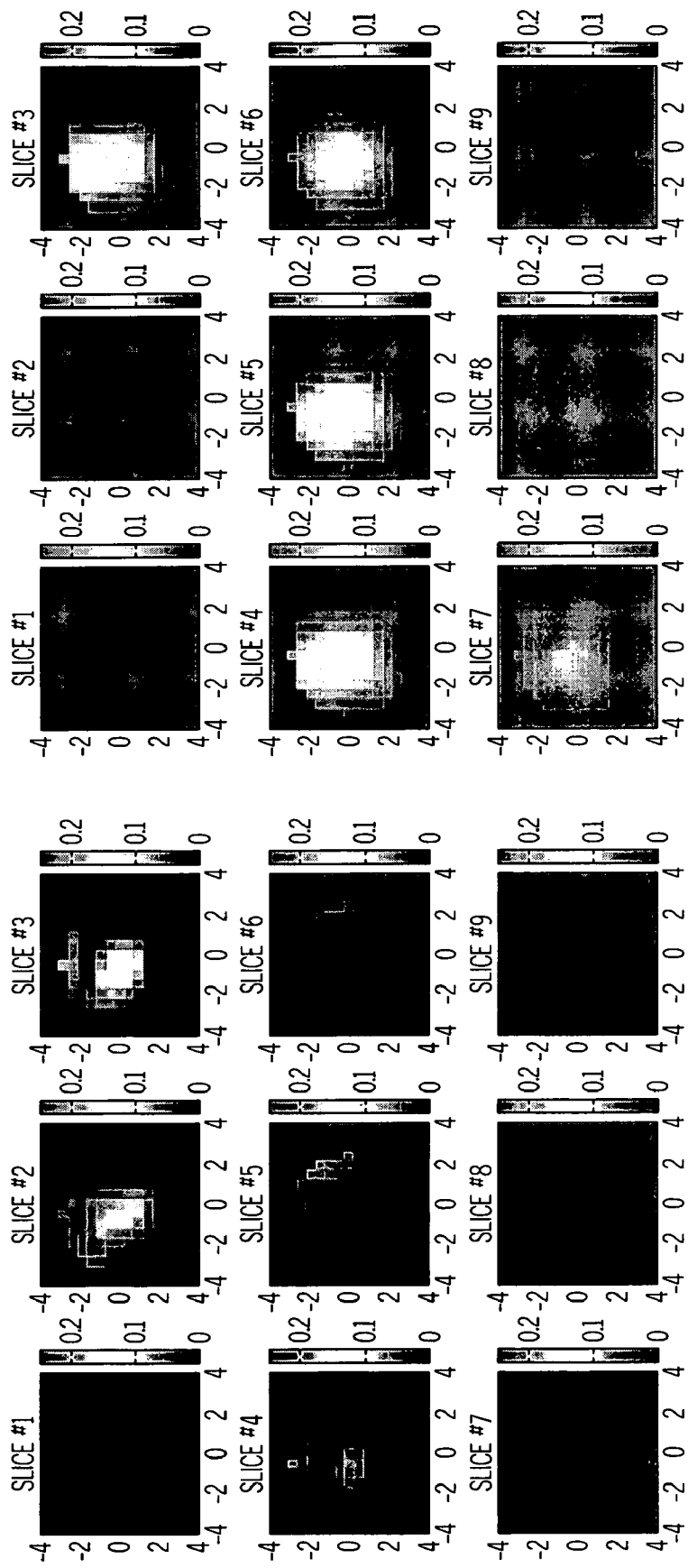
FIG. 14 depicts the reconstructed optical absorption maps of the 3-cm-diameter low-contrast absorber obtained at 50 MHz (first column), 140 MHz (second column) and 350 MHz (third column) modulation frequencies, respectively.
Figures 14E, 14F:
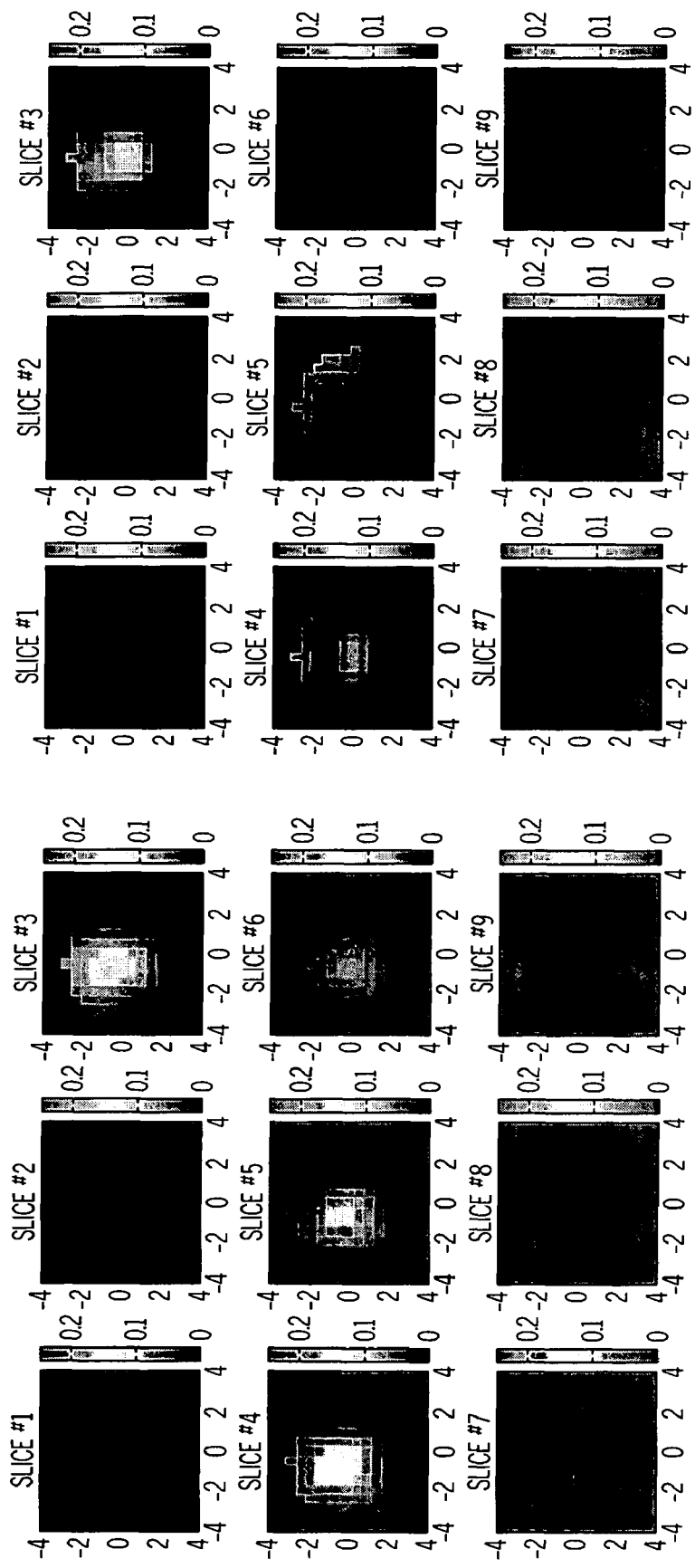
Figures 14G, 14H:
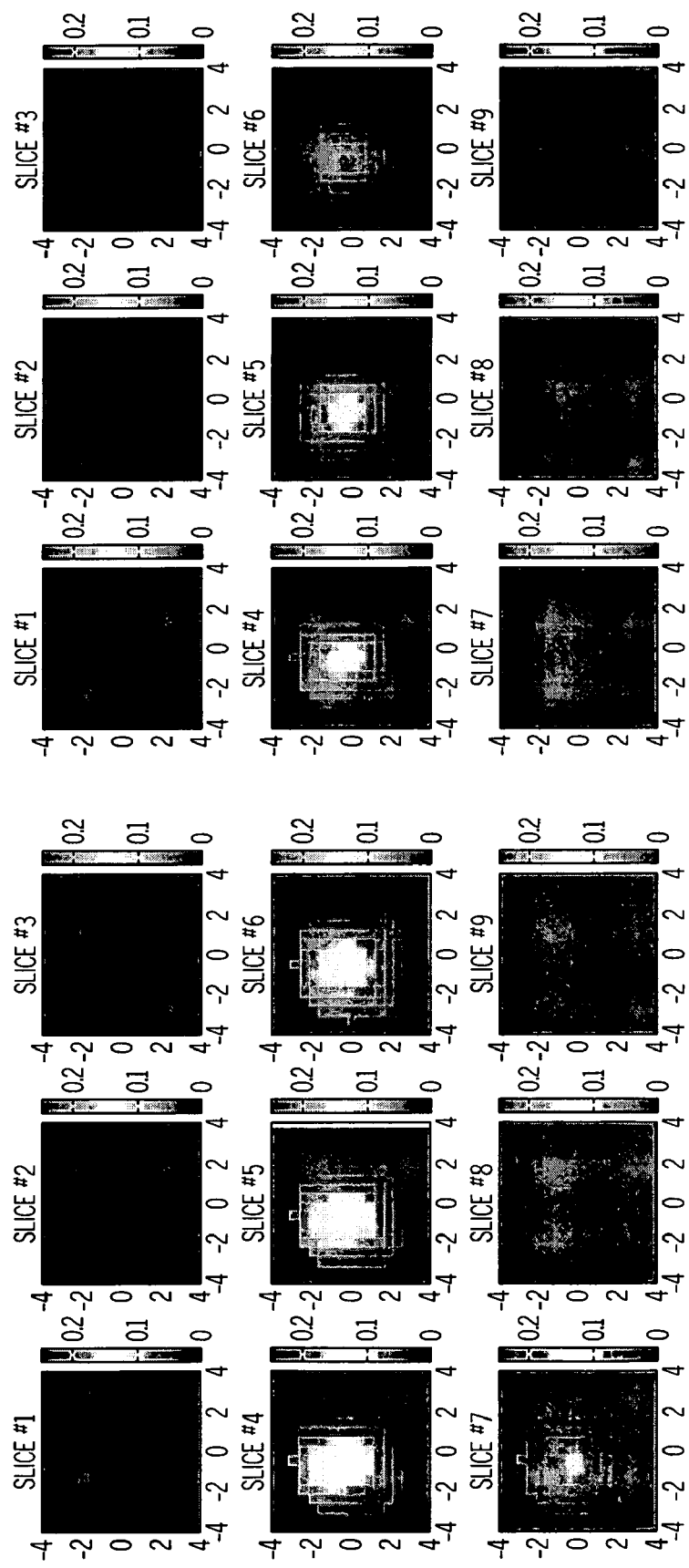
Figures 14I, 14J:
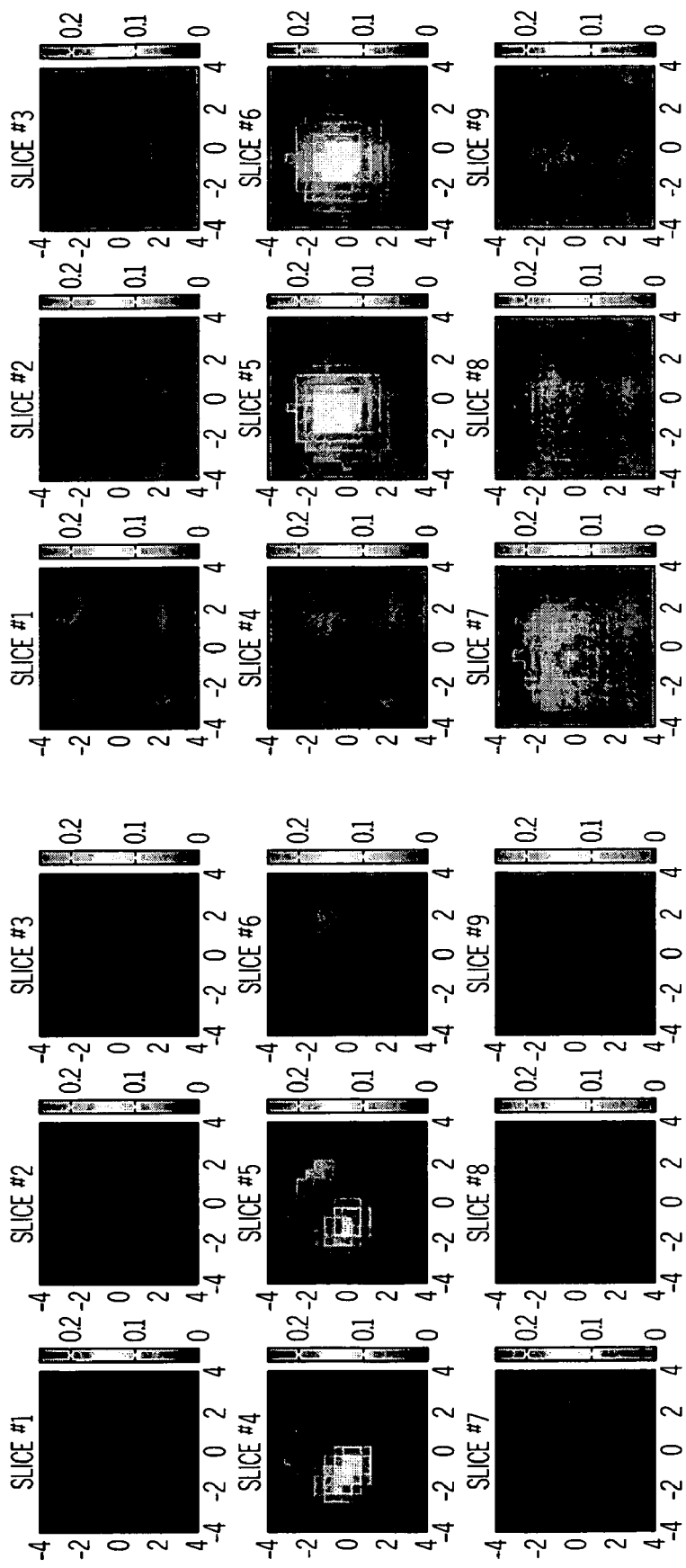
Figure 15B:
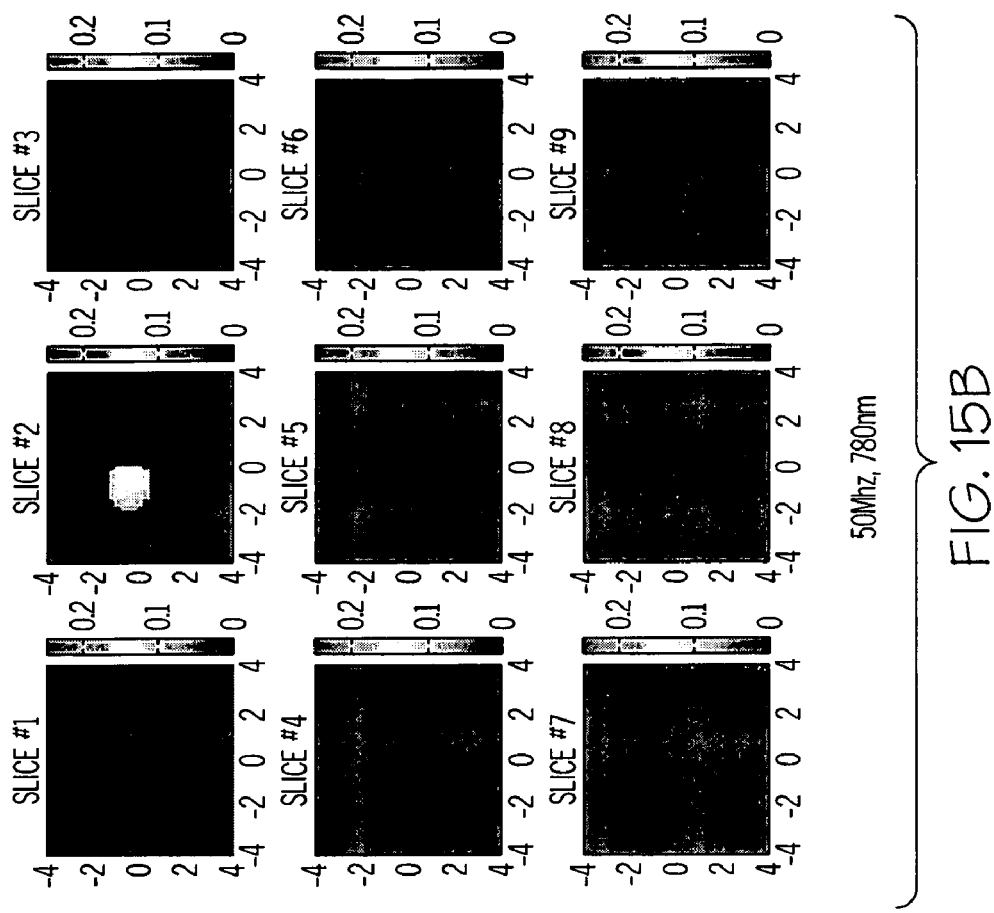
FIG. 15 depicts the co-registered ultrasound images (first column) and reconstructed optical absorption maps of the 1-cm high-contrast absorber obtained at 50 MHz (second column), 140 MHz (third column) and 350 MHz (fourth column) modulation frequencies, respectively.
Figure 15A:
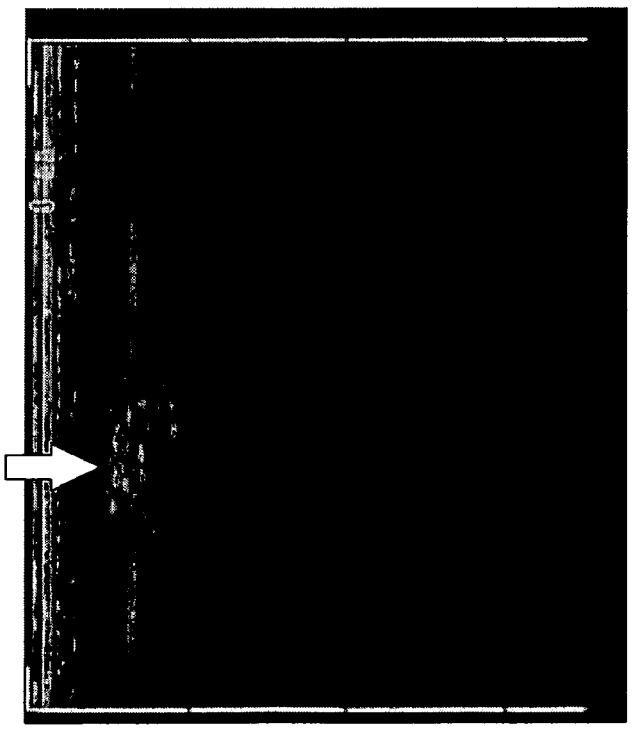
Figure 15F:
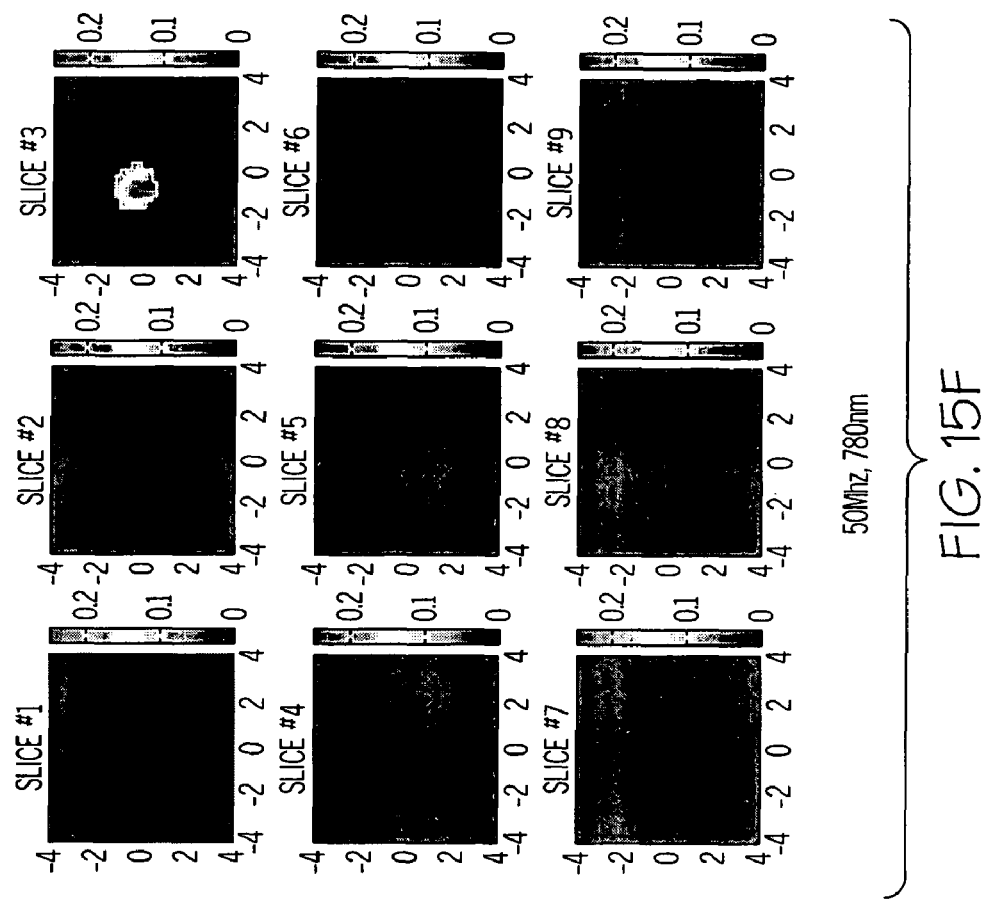
Figure 15E:
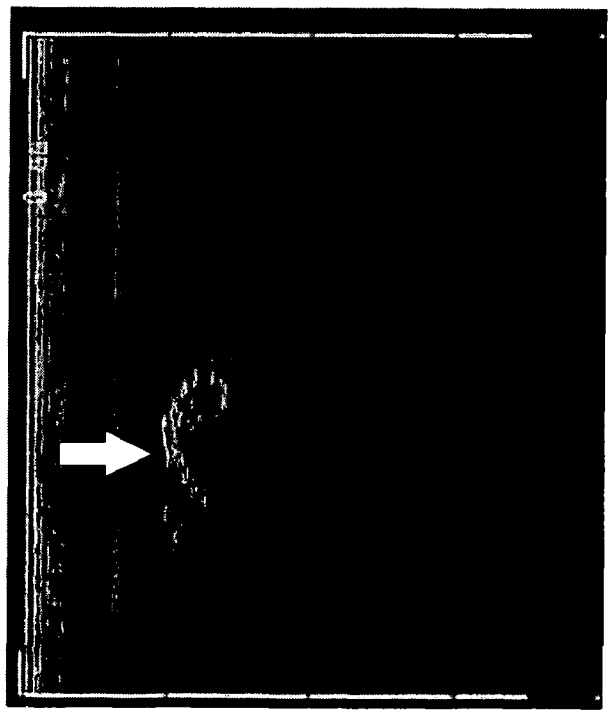
Figure 15J:
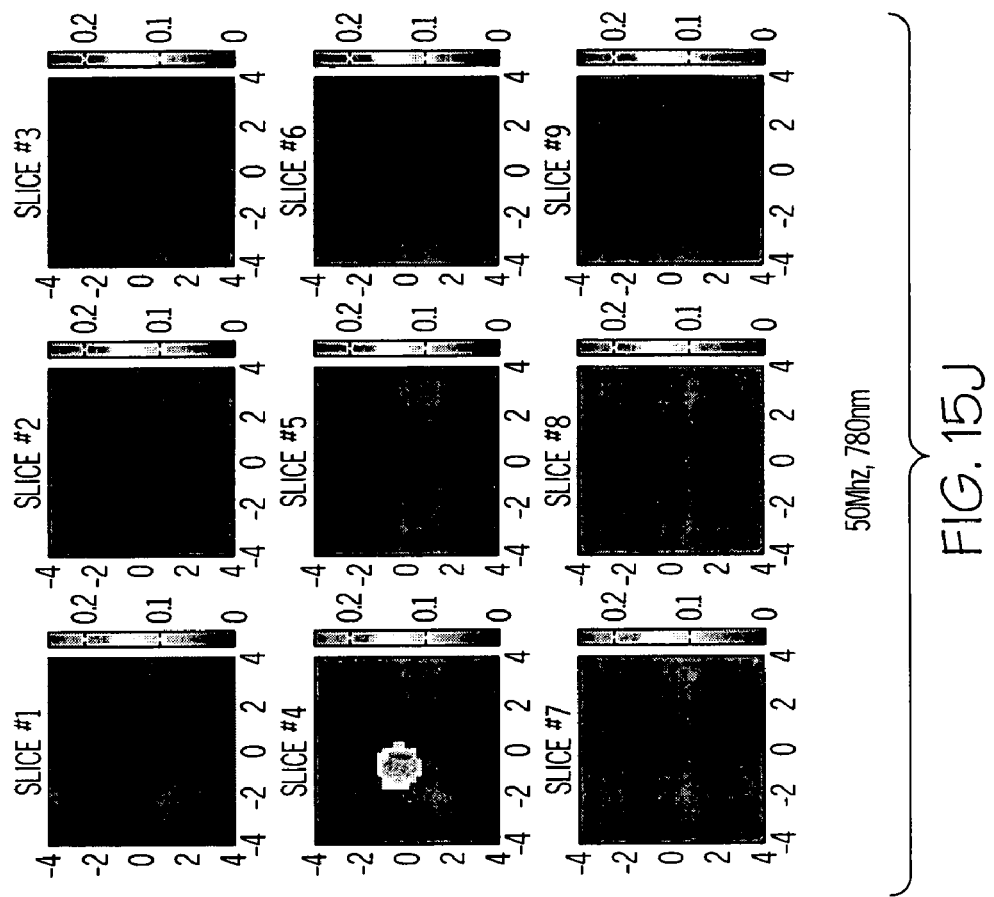
Figure 15I:
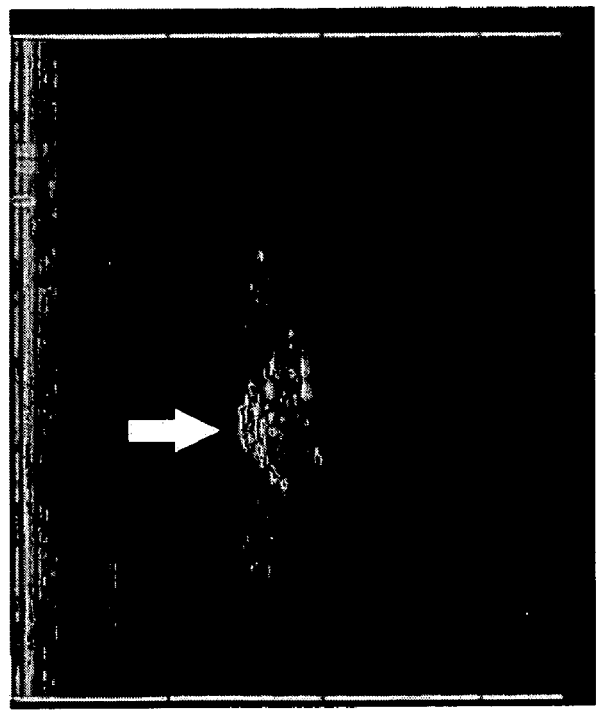
Figure 15N:
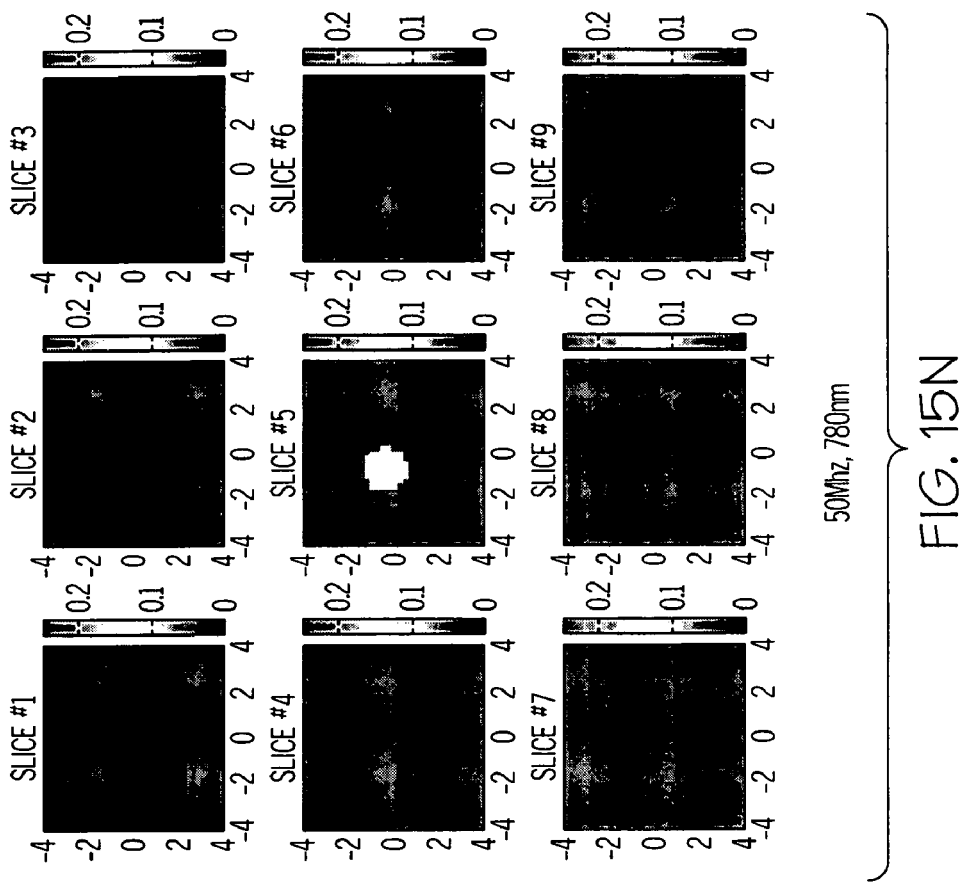
Figure 15M:
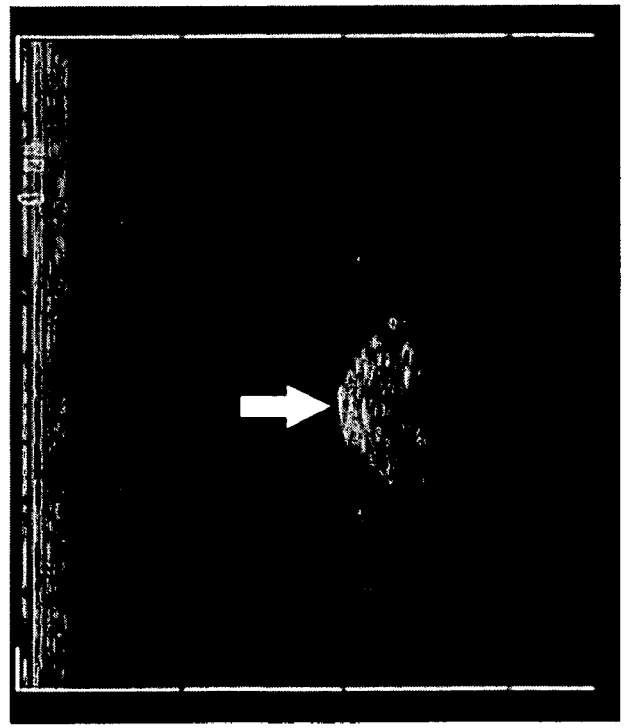
Figures 15O, 15P:
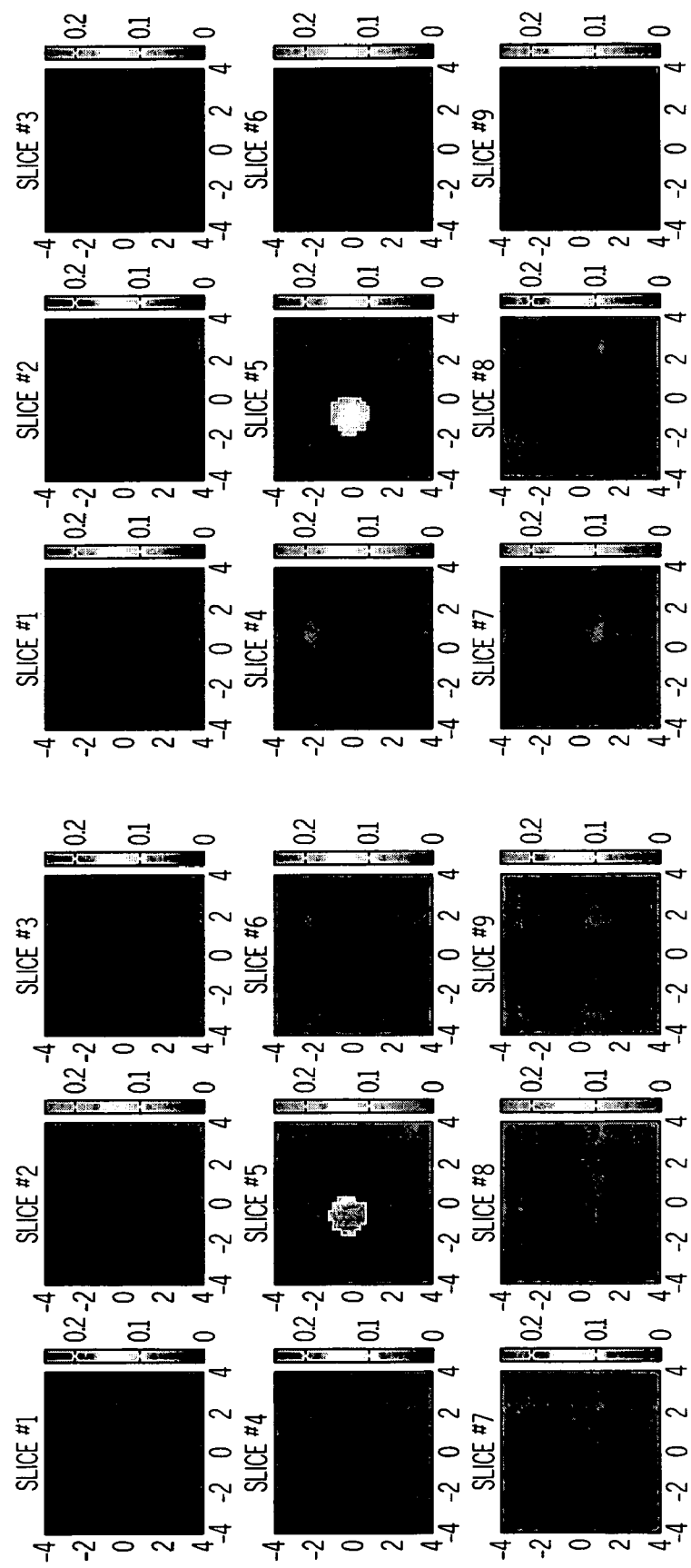
Figure 15R:
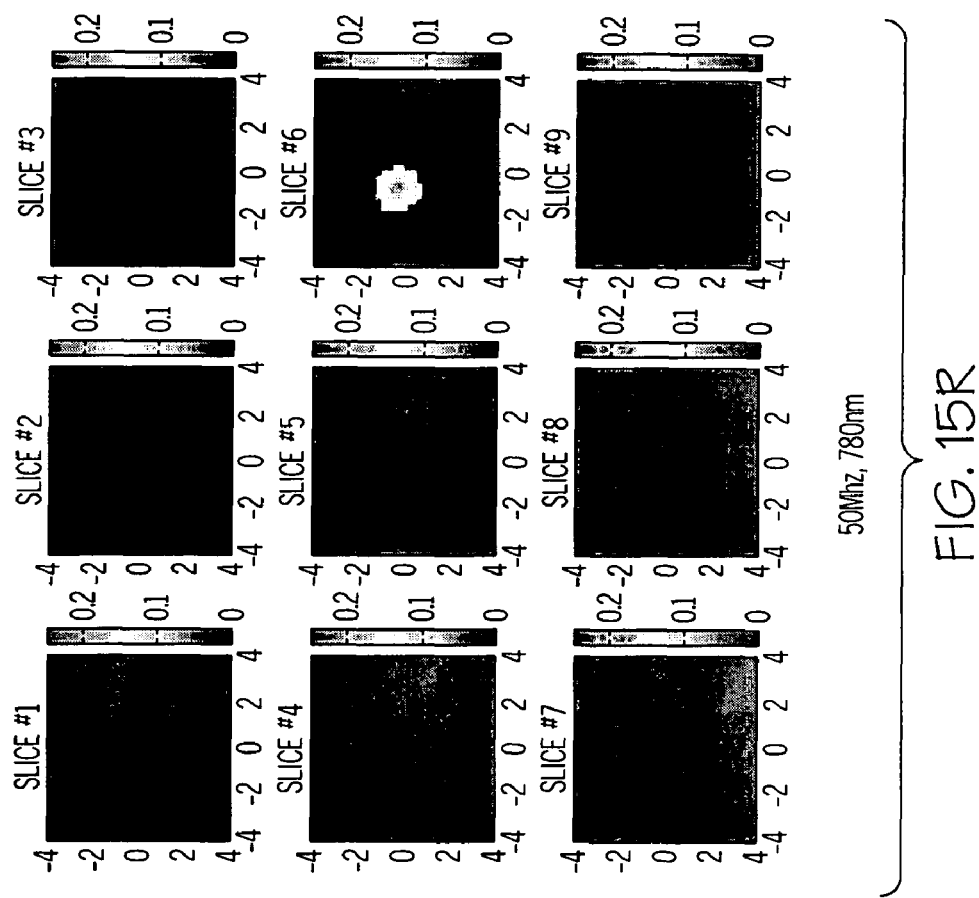
Figure 15Q:
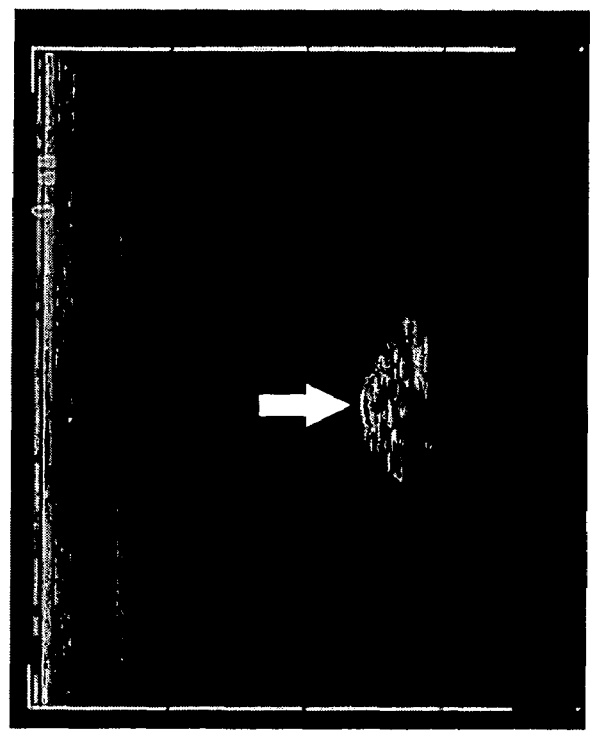
Figure 15V:
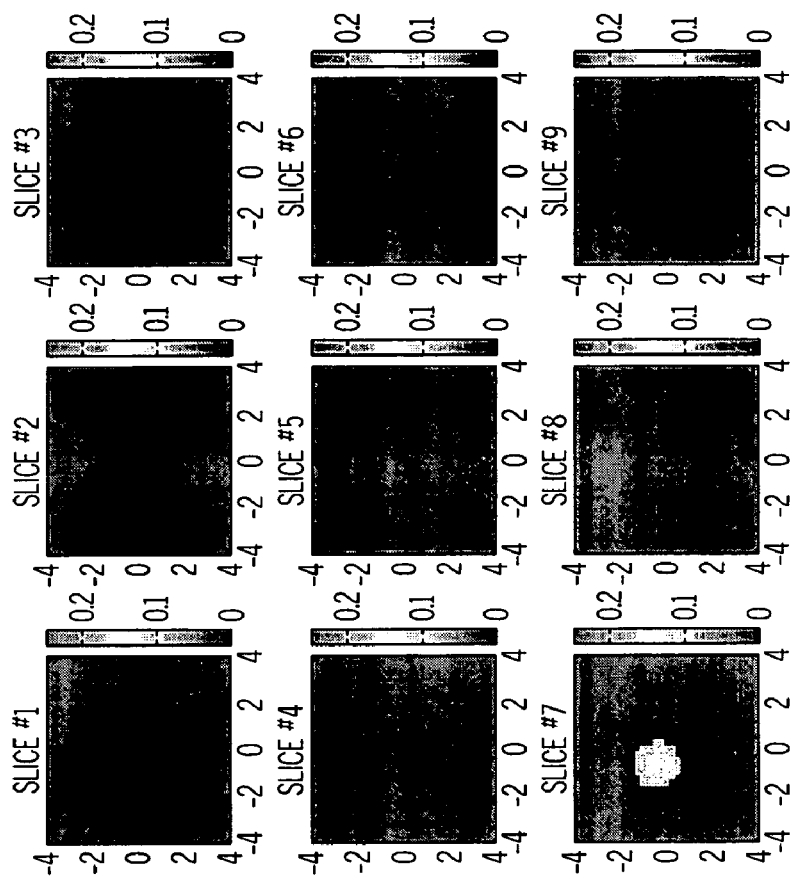
Figure 15U:
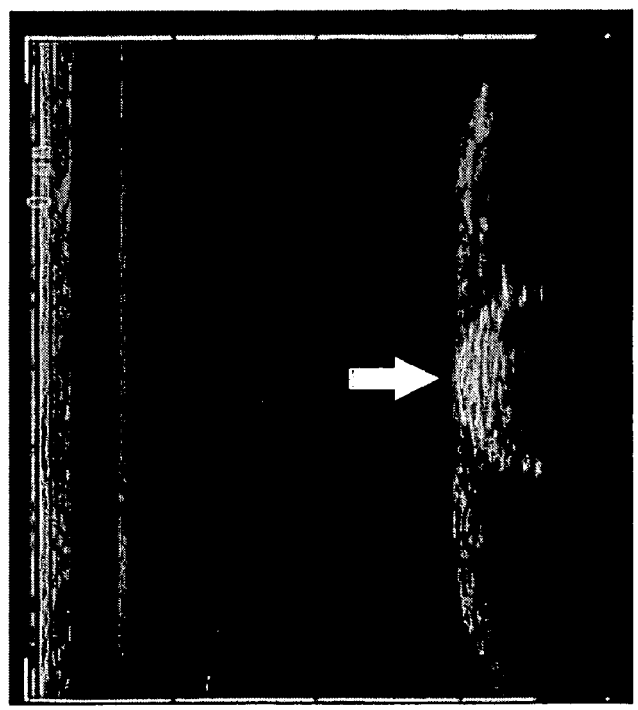
Figures 15W, 15X:
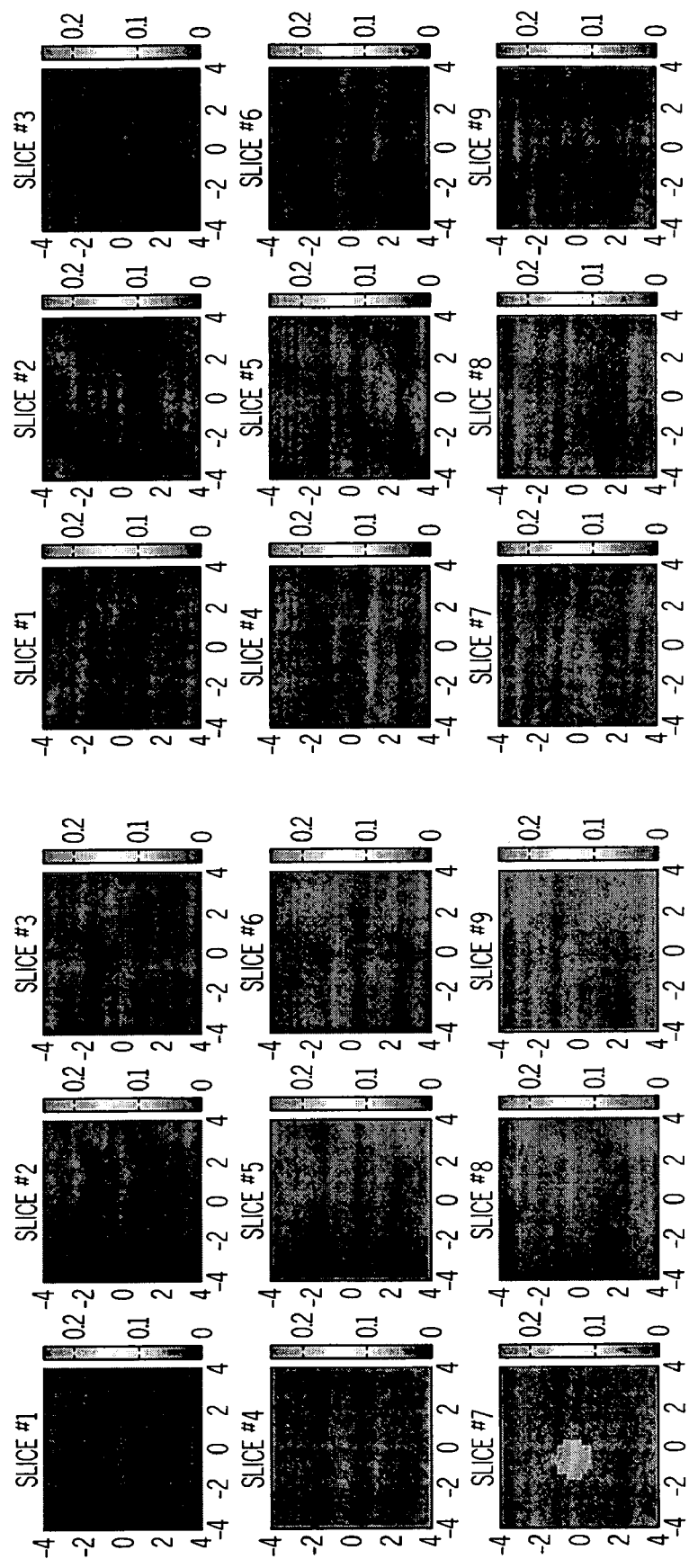
Figures 16C, 16D:
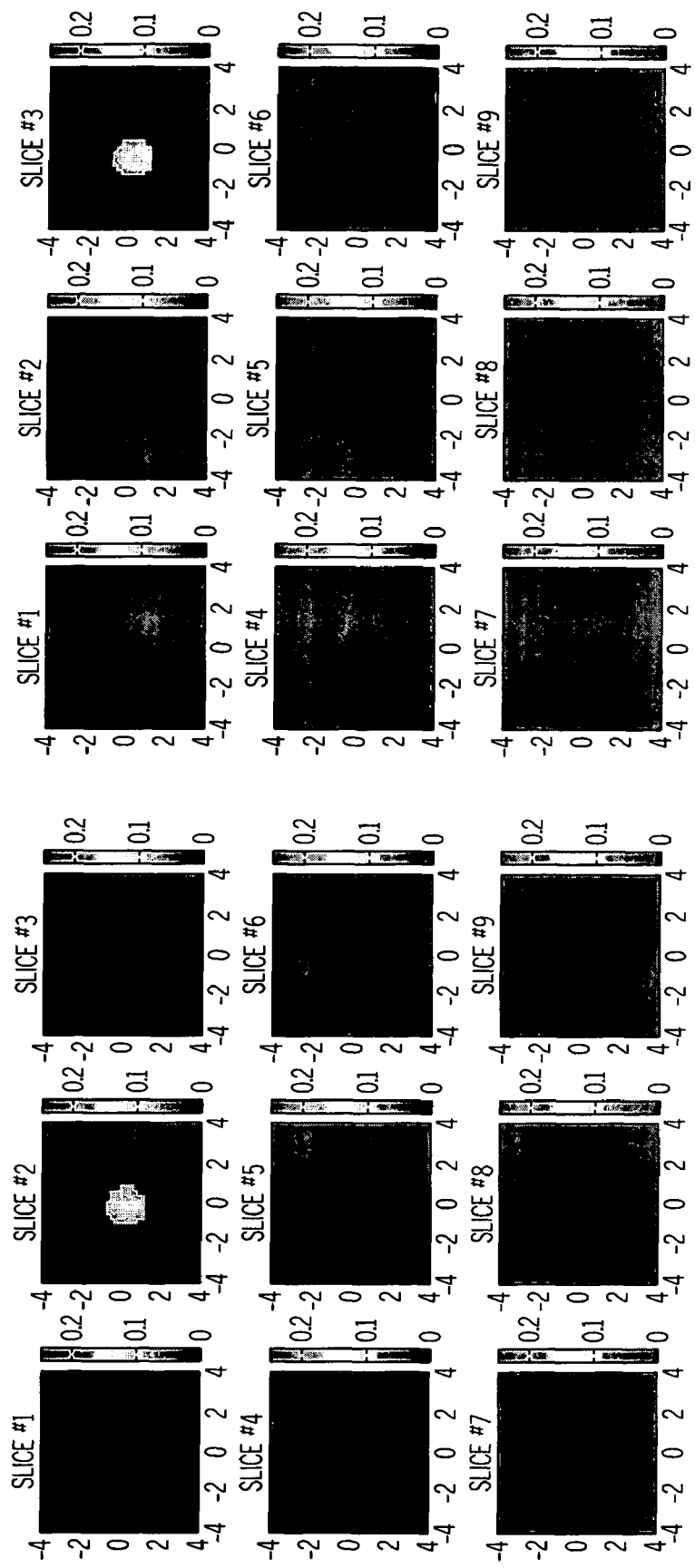
FIG. 16 depicts the reconstructed optical absorption maps of the 1-cm low-contrast absorber obtained at 50 MHz (first column), 140 MHz (second column) and 350 MHz (third column) modulation frequencies.
Figures 16G, 16H:
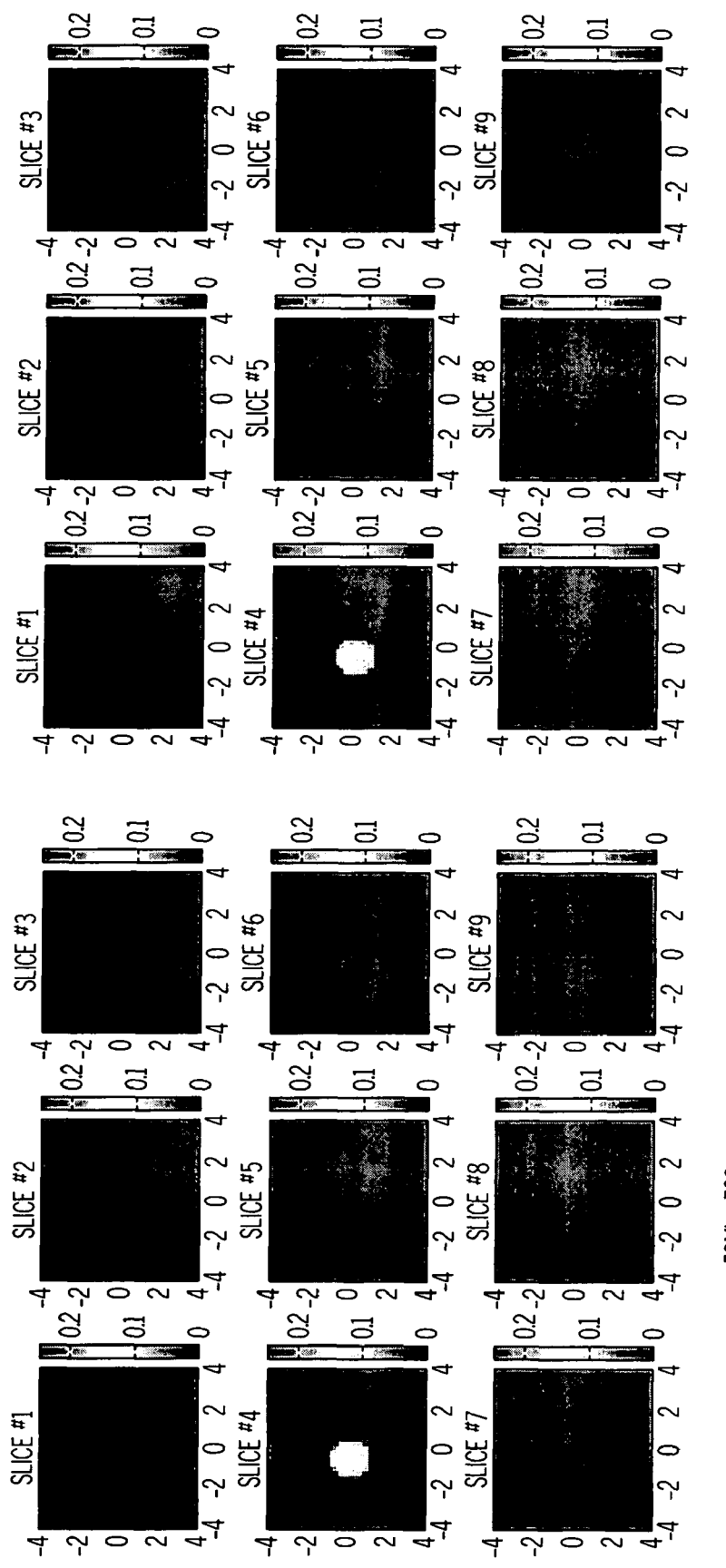
Figures 16I, 16J:
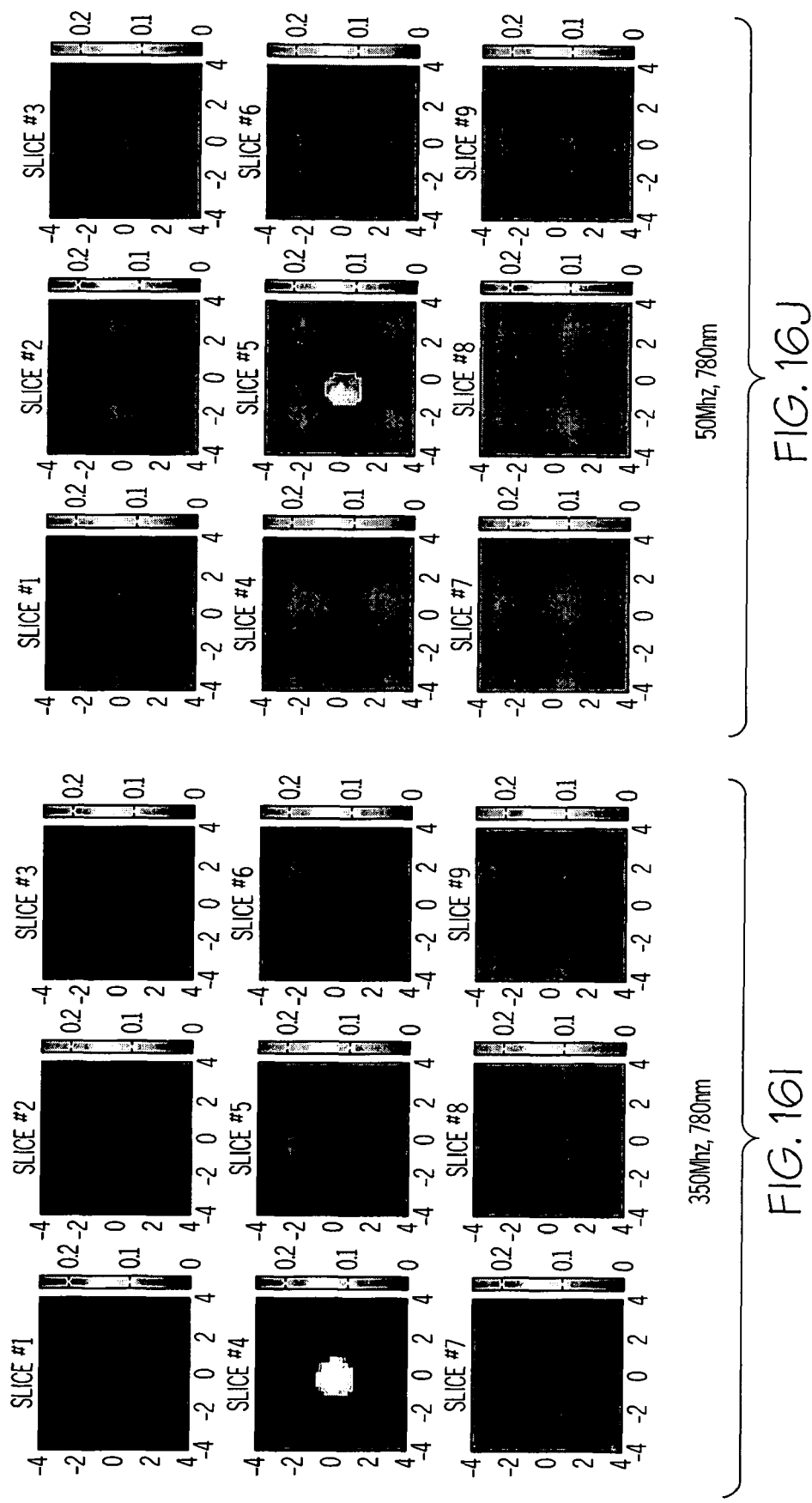
Figures 16M, 16N:
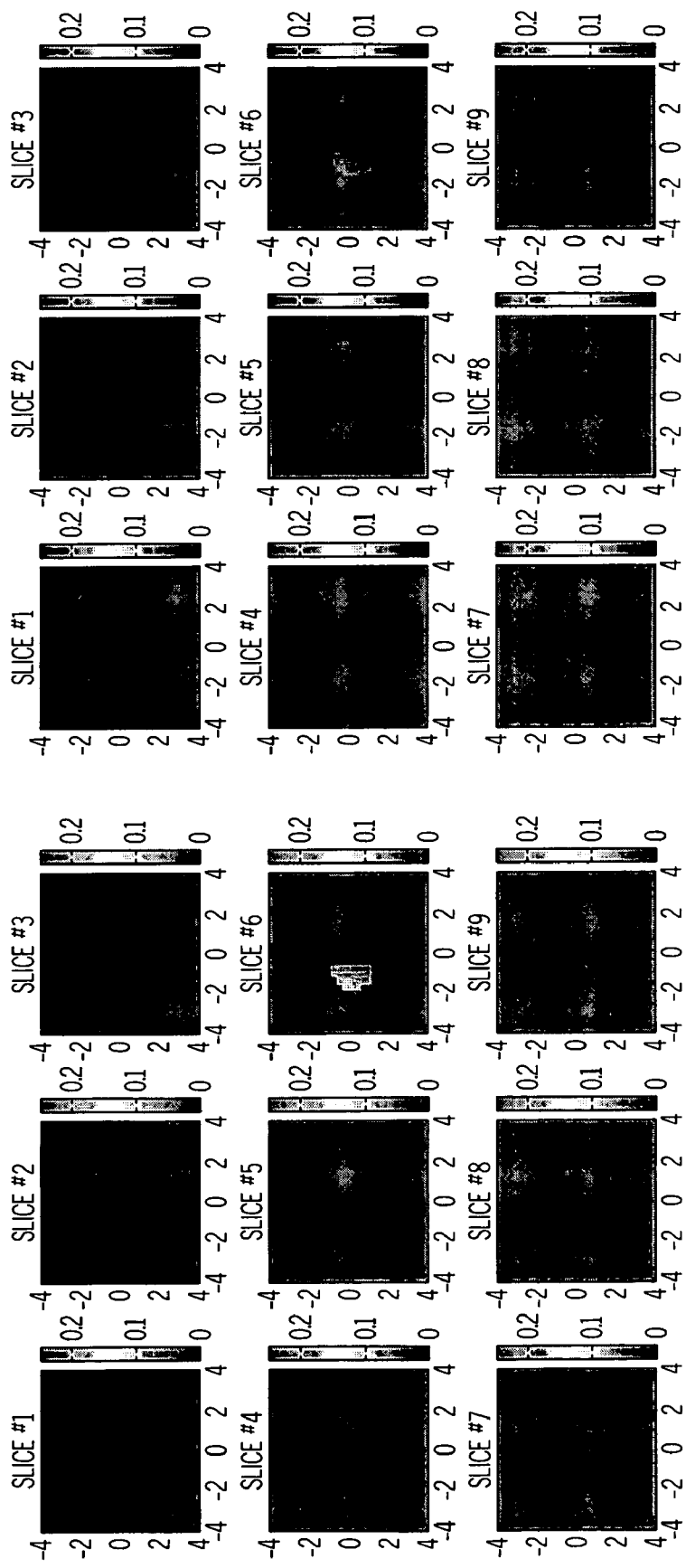

For each set of simulations, the optical absorption coefficient of the target placed at [0, 0, 1.0 cm] was varied in an amount of 0.1 cm$^{-1}$ to 0.25 cm$^{-1}$. When the chest wall was located at 1.6 cm and 2.0 cm, the target was a 1 cm cube. When the chest wall was located at 1.3 cm, a smaller target of size 1 cm×1 cm×0.5 cm was used. The reduced scattering coefficient of the target was always kept at 15 cm$^{-1}$. The reconstructed average $\mu_a$ obtained from the corresponding two-layer model and the semi-infinite model are shown in the FIG. 11. The average was computed within 6 dB of the maximum value. Results obtained from the layered model are more accurate than those obtained from the semi-infinite model. The improvement of reconstructed $\mu_a$ varies from 10.6% to 13.8% when the second layer is located at 1.3 cm depth. As the first layer thickness increases to 2 cm, the improvement is negligible.

To evaluate the simulation results, two sets of experiments were conducted. The top layer was made of homogeneous 0.5% Intralipid solution of fitted values $\mu_a$=0.02 cm$^{-1}$ and $\mu'_s$=4.78 cm$^{-1}$, and the bottom layer was a silicone having values $\mu_a$=0.08 cm$^{-1}$ and $\mu'_s$=8.3 cm$^{-1}$. The silicone was placed 1.4 cm and 1.8 cm beneath the Intralipid solution in the first and second experiment set, respectively. Measurements were made from the homogeneous Intralipid solution, the layered medium, and the layered medium with a 1 cm$^3$ silicone absorber. Two absorbers of high and low optical contrasts were used. The calibrated $\mu_a$ of the high contrast absorber was between 0.2 cm$^{-1}$ and 0.3 cm$^{-1}$, and the $\mu'_s$ value was 9.6 cm$^{-1}$. The calibrated $\mu_a$ of the low contrast absorber was 0.07 cm$^{-1}$, and the $\mu'_s$ was 9.6 cm$^{-1}$.

FIG. 12 (a) shows a B-scan (background scan) ultrasound image of a two-layer medium for reference measurement. The center depth of the bottom layer is 1.4 cm underneath the Intralipid surface. FIG. 12 (b) is a B-scan ultrasound image of the target located on top of the silicone phantom. The high absorber is located at [0, 0, 0.9 cm] inside the Intralipid solution. With the reported fitting procedure, the estimated bulk absorption and reduced scattering coefficients for the top layer were 0.025 cm$^{-1}$ and 6.6 cm$^{-1}$, and the corresponding values for the second layer were 0.078 cm$^{-1}$ and 7.6 cm$^{-1}$. FIG. 12 (c) and (d) are the reconstructed absorption and diffusion maps at 780 nm obtained from the semi-infinite model. FIG. 12 (e) and (f) are the reconstructed absorption and diffusion maps obtained from the layered model at the same wavelength. The uniformity of the images is slightly improved by applying the layered model. Table I gives a comparison of the reconstructed results obtained from the semi-infinite model and the layered model. When the semi-infinite model was used for reconstruction, the average reconstructed absorption coefficients within the top and bottom layers of the target region were 0.147 cm$^{-1}$ and 0.147 cm$^{-1}$, respectively, while the average reconstructed $\mu'_s$s within the top and bottom layers of the target region were 11.6 cm$^{-1}$ and 13.1 cm$^{-1}$, respectively. When the layered model was used, the average reconstructed absorption coefficients of the top and bottom layers of the target region were 0.17 cm$^{-1}$ and 0.16 cm$^{-1}$, respectively, while the average reconstructed $\mu'_s$s of the top and bottom layers of the target region were 12.2 cm$^{-1}$ and 11.4 cm$^{-1}$, respectively. The accuracy of reconstructed average $\mu_a$ and $\mu'_s$ was improved by 9.4% and 5.6% assuming $\mu_a$=0.2 cm$^{-1}$, respectively, when the corresponding two-layer model instead of the semi-infinite model was used.

The reconstruction results obtained from the low contrast absorber centered at [0, 0, 0.9 cm] with the second silicone layer located 1.4 cm deep in the Intralipid solution are given in Table I. Using the reported fitting procedure, the estimated bulk absorption and reduced scattering coefficients of the top layer were 0.025 cm$^{-1}$ and 6.6 cm$^{-1}$, and the corresponding values of the second layer were 0.082 cm$^{-1}$ and 8.3 cm$^{-1}$. When the semi-infinite model was used for reconstruction, the average reconstructed absorption coefficients within the top and bottom layers of the target region were 0.068 cm$^{-1}$ and 0.065 cm$^{-1}$, respectively, while the average reconstructed $\mu'_s$s within the top and bottom layers of the target region were 8.56 cm$^{-1}$ and 8.6 cm$^{-1}$, respectively. When the layered model was used for reconstruction, the average reconstructed absorption coefficients within the top and bottom layers of the target region were 0.074 cm$^{-1}$ and 0.078 cm$^{-1}$, respectively, while the average reconstructed $\mu'_s$s within the top and bottom layers of the target region were 8.54 cm$^{-1}$ and 8.96 cm$^{-1}$, respectively. The reconstructed average values of $\mu_a$ and $\mu'_s$ were very similar when the corresponding two-layer model instead of the semi-infinite model was used.

The results of second set experiment are also given in Table I. When the second layer was located at 1.8 cm deep in the intralipid, the improvement of using the layered model compared with using semi-infinite model was smaller than that obtained from the first set of experiments. For the high contrast absorber, the reconstructed absorption coefficients within the top and bottom layers of the target region were improved from 0.187 cm$^{-1}$ and 0.173 cm$^{-1}$ to 0.198 cm$^{-1}$ and 0.188 cm$^{-1}$, respectively, while the average reconstructed $\mu'_s$s within the top and bottom layers of the target region were changed from 9.1 cm$^{-1}$ and 9.09 cm$^{-1}$, to 9.02 cm$^{-1}$ and 8.99 cm$^{-1}$, respectively.

By applying the two-layer model instead of the semi-infinite model, the accuracy of reconstructed top layer $\mu_a$ and bottom layer $\mu'_s$ was improved by 6.5% of the expected value assuming $\mu_a$=0.2 cm$^{-1}$, while $\mu'_s$ changed slightly. For the low contrast absorber, slight change was observed between the results obtained from the layered model and the semi-infinite model. When the semi-infinite model was used, the reconstructed absorption coefficients within the top and bottom layers of the target region were 0.073 cm$^{-1}$ and 0.076 cm$^{-1}$, respectively, while the average reconstructed $\mu'_s$ within the top and bottom layers of the target region were 10.26 cm$^{-1}$ and 9.16 cm$^{-1}$, respectively. When the layered model was used, the reconstructed absorption coefficients within the top and bottom layers of the target region were 0.074 cm$^{-1}$ and 0.075 cm$^{-1}$, respectively, while the average reconstructed $\mu'_s$s within the top and bottom layers of the target region were 10.24 cm$^{-1}$ and 9.07 cm$^{-1}$, respectively.

ers, it is desirable for the region of interest to be twice the size of the absorber to ensure accurate reconstruction of target optical properties.

Absorbers having diameters of 1-cm and 3-cm of low contrast (calibrated value at 780 nm $\mu_a$=0.07 cmP$^{-1P}$, $\mu'_s$=5.50 cmP$^{-1P}$) and high contrast (calibrated value at 780 nm $\mu_a$=0.23 cmP$^{-1P}$, $\mu'_s$=5.45 cmP$^{-1P}$) were imbedded in Intralipid™ solution of 0.07% concentration. The fitted background $\overline{\mu_a}$ and $\overline{\mu'_s}$ were in the range of 0.02 to 0.031 cmP$^{-1P}$ and 4.9 to 6.1 cmP$^{-1P}$ in different sets of experiments. In each set of 1-cm absorber experiments, the absorber was centered at depths of 0.5, 1.0, 1.5, 2.0, 2.5, 3, and 3.5 cm from the center of the probe. In each set of 3-cm absorber experiments, the absorber was centered at depths of 2, 2.5, 3, and 3.5 cm. For each target location, three sets of measurements obtained from three modulation frequencies were used to reconstruct target absorption maps. The average $\mu_a$ value measured within full width and half maximum (FWHM) of each x-y target layer was used to quantitatively compare the reconstruction results.

To evaluate the possible effect of region of interest or fine-mesh zone selection on the accuracy of the reconstructed absorption coefficients, the target using a region of interest twice the size of the real target in x-y dimensions (2×) and three times (3×) the size of the target in x-y dimensions was reconstructed. Results obtained from these two ROIs were compared.

Clinical studies were performed at the Radiology Department of the University of Connecticut Health Center. The

TABLE 1

| Target located on top of the second layer phantom | | High contrast absorber | | Low contrast absorber | |
|---|---|---|---|---|---|
| | | $\mu_a$ | $\mu'_s$ | $\mu_a$ | $\mu'_s$ |
| Expected values (cm$^{-1}$) | | 0.2-0.3 | 9.6 | 0.07 | 9.6 |
| Second layer at 1.4 cm | Reconstructed values* using a semi-infinite model | 0.147/0.147 | 11.60/13.13 | 0.068/0.065 | 8.56/8.60 |
| | Reconstructed values* using a layered model | 0.172/0.160 | 12.20/11.39 | 0.074/0.078 | 8.54/8.96 |
| Second layer at 1.8 cm | Reconstructed values* using a semi-infinite model | 0.187/0.173 | 9.10/9.09 | 0.073/0.076 | 10.26/9.16 |
| | Reconstructed values* using a layered model | 0.198/0.188 | 9.02/8.99 | 0.074/0075 | 10.24/9.07 |

*Mean values obtained within target region for each target layer.

Thus, with the proposed fitting method, optical properties of the two-layer model can be obtained with acceptable accuracy. The accuracy of $\mu'_s$ for the second layer can always reach about 105% to about 114.6% of the estimated value, and the accuracy of corresponding $\mu_a$ is around about 82.7% to about 160% of the estimated value. The accuracy of $\mu_a$ for the first layer is about 70% of the estimated value, and the accuracy of corresponding $\mu'_s$ is around about 130% to about 137% of the estimated value. As expected, the greater thickness of the first layer results in greater errors in the derived optical coefficients.

Example 2

This example was conducted to evaluate the possible effect of fine-mesh zone selection on accuracy of the reconstructed absorption coefficients. In order to do so, the target was reconstructed using regions of interest (ROIs) twice the size of the real target in x-y dimensions and three times the size of the target in x-y dimensions. The results show that the ROI has negligible effect on reconstructed optical properties of larger 3-centimeters absorbers. For smaller 1-centimeters absorb- Health Center IRB committee approved the human subject protocol. A state-of-the art US machine, ATL Sono CT, was used for the study. Ultrasound images and optical measurements were acquired simultaneously at multiple locations including the lesion region, a normal region of the same breast, and a symmetric normal region of the contralateral breast. The optical data acquired at normal regions were used as reference to calculate the scattered field caused by inclusion.

FIG. 13 shows the co-registered ultrasound images (first column) and reconstructed optical absorption maps of the 3-cm-diameter high-contrast absorber obtained at 50 MHz (second column), 140 MHz (third column), and 350 MHz (fourth column) modulation frequencies. The reconstructed absorption maps shown in FIG. 13 were obtained at 780 nm with the ROI in x-y dimensions equal to twice the size of the real target. The same target was translated in 0.5 cm depth steps to target centers at 2 cm, 2.5 cm, 3 cm, and 3.5 cm. In other words, slices at distances of 0.5 centimeter were examined for the image. In each image, there are 9 x-y images of 9 cm by 9 cm obtained from 0.5 cm (slice #1) to 4.5 cm (slice #9) in depth with steps of 0.5 cm. The slices are numbered from left to right and top to bottom.

Ideally, the target should uniformly occupy 6 layers in z direction. However, the last two target layers close to the bottom were visible only in images obtained at 50 Mhz when the target center was located at 2.0, 2.5 and 3.0 cm, respectively. In images obtained at 140 Mhz, the top four target layers were seen whereas in images obtained at 350 Mhz only the top three target layers were seen. This is due to the significant light absorption of the top target layers that limits the number of photons penetrating into the deep layers and ultimately detected at the surface. This light-shadowing phenomenon is very similar to the well-known ultrasound shadow effect of a large inclusion, where bottom layers of the inclusion or normal tissues underneath the lesion appear black in the image (little sound reflection) due to significant sound absorption of top layers. The shadowing effect is more pronounced at high RF light modulation frequencies.

Table 2 provides the reconstructed average target $\mu_a$ measured within FWHM of each target layer and obtained at three modulation frequencies. The first column lists the target center depth and the second through fourth columns present the reconstructed average $\mu_a$ obtained at the corresponding layer for 50, 140, and 350 MHz, respectively. Results are listed for ROIs of two (2×) and three (3×) the real target size in x-y dimensions. The percentage ratio of the calculated to the calibrated value of $\mu_a=0.23$ cmP$^{-1P}$ is given in parenthesis. The average $\mu_a$ calculated from the first five target layers is also given at the bottom of each row. The highest reconstructed values, (68%, 50 Mhz) and (63%, 140 Mhz), are obtained at the third target layer when the target center is located at 2 cm depth. The average values over the first five target layers are 59% (50 Mhz) and 47% (140 Mhz), respectively. If the data are averaged over the first four layers, the reconstruction accuracy at 140 Mhz improves to 53%. For 350 Mhz, the highest value, 83%, is obtained at the second target layer and the average value is 48%. If the data are averaged over the first three layers, the reconstruction accuracy improves to 67%. The reconstructed average values drop quickly when the target center is translated deeper. In our clinical study, the breast is scanned with the combined probe compressed against the chest wall. The lesions are often located within a 3 to 4 cm depth. Clinical imaging conditions therefore most closely resemble targets at the 2 cm or 2.5 cm depths.

TABLE 2

| Center Depth | 50 MHz | | | 140 MHz | | | 350 MHz | | |
|---|---|---|---|---|---|---|---|---|---|
| High Contrast 3 cm absorber | ROI Layers | 2 x | 3 x | ROI Layers | 2 x | 3 x | ROI: Layers | 2 x | 3 x |
| 2.0 cm | #1: | 0.123(54) | 0.118(51) | #1: | 0.110(48) | 0.107(47) | #1: | 0.140(61) | 0.139(60) |
| | #2: | 0.135(59) | 0.132(57) | #2: | 0.123(54) | 0.121(53) | #2: | 0.192(83) | 0.190(83) |
| | #3: | 0.156(68) | 0.153(67) | #3: | 0.144(63) | 0.143(62) | #3: | 0.149(65) | 0.148(64) |
| | #4: | 0.152(66) | 0.150(65) | #4: | 0.111(48) | 0.111(48) | #4: | 0.040(18) | 0.036(16) |
| | #5: | 0.110(48) | 0.108(47) | #5: | 0.055(24) | 0.055(24) | #5: | 0.029(13) | 0.029(13) |
| | #6: | 0.073(31) | 0.071(31) | #6: | 0.024(11) | 0.023(10) | #6: | 0.027(12) | 0.027(12) |
| | Ave: | 0.135(59) | 0.132(57) | Ave | 0.109(47) | 0.107(47) | Ave: | 0.110(48) | 0.108(47) |
| 2.5 cm | #1: | 0.123(53) | 0.120(52) | #1: | 0.109(47) | 0.107(47) | #1: | 0.159(69) | 0.159(69) |
| | #2: | 0.143(62) | 0.140(61) | #2: | 0.132(57) | 0.130(57) | #2: | 0.178(77) | 0.177(77) |
| | #3: | 0.143(62) | 0.139(60) | #3: | 0.112(48) | 0.110(48) | #3: | 0.123(53) | 0.122(53) |
| | #4: | 0.110(48) | 0.109(47) | #4: | 0.067(29) | 0.066(29) | #4: | 0.043(19) | 0.038(17) |
| | #5: | 0.074(32) | 0.072(31) | #5: | 0.038(17) | 0.038(17) | #5: | 0.029(13) | 0.028(12) |
| | #6: | 0.048(21) | 0.044(19) | #6: | 0.023(10) | 0.023(10) | #6: | 0.026(11) | 0.026(11) |
| | Ave: | 0.119(52) | 0.116(50) | Ave: | 0.092(40) | 0.090(39) | Ave: | 0.106(46) | 0.105(46) |
| 3.0 cm | #1: | 0.119(52) | 0.117(51) | #1: | 0.107(47) | 0.106(46) | #1: | 0.165(72) | 0.163(71) |
| | #2: | 0.126(55) | 0.123(53) | #2: | 0.109(47) | 0.107(47) | #2: | 0.167(73) | 0.167(73) |
| | #3: | 0.103(45) | 0.102(44) | #3: | 0.083(36) | 0.081(35) | #3: | 0.088(38) | 0.088(38) |
| | #4: | 0.075(33) | 0.073(32) | #4: | 0.057(25) | 0.057(25) | #4: | 0.034(15) | 0.030(13) |
| | #5: | 0.050(22) | 0.047(20) | #5: | 0.032(14) | 0.028(12) | #5: | 0.026(11) | 0.026(11) |
| | #6: | 0.040(18) | 0.036(16) | #6: | 0.024(11) | 0.023(10) | #6: | 0.025(11) | 0.025(11) |
| | Ave: | 0.095(41) | 0.092(40) | Ave: | 0.078(34) | 0.076(33) | Ave: | 0.096(42) | 0.095(41) |
| 3.5 cm | #1: | 0.095(41) | 0.092(40) | #1: | 0.090(39) | 0.087(38) | #1: | 0.141(61) | 0.140(61) |
| | #2: | 0.086(37) | 0.083(36) | #2: | 0.091(39) | 0.088(38) | #2: | 0.110(48) | 0.110(48) |
| | #3: | 0.066(29) | 0.064(28) | #3: | 0.076(33) | 0.075(33) | #3: | 0.042(18) | 0.042(18) |
| | #4: | 0.049(21) | 0.043(19) | #4: | 0.048(21) | 0.048(21) | #4: | 0.026(11) | 0.026(11) |
| | #5: | 0.040(17) | 0.037(16) | #5: | 0.030(13) | 0.027(12) | #5: | 0.025(11) | 0.025(11) |
| | Ave: | 0.067(29) | 0.064(28) | Ave: | 0.067(29) | 0.065(28) | Ave: | 0.069(30) | 0.069(30) |

This controlled study clearly shows that large absorbing tumors are under-reconstructed and advanced system and non-linear algorithmic developments are needed to improve the reconstruction accuracy of target optical properties. CW systems offer the best penetration but will not provide phase information that enhances sensitivity for imaging smaller lesions.

One issue is the selection of ROI or fine-mesh zone used in image reconstruction. As can be seen from Table I, the ROI has negligible effect as the maximum change observed from two different ROIs (2× and 3×) is only 3% for targets located at different depths and probed with different modulation frequencies.

FIG. 14 shows the reconstructed optical absorption maps of the 3-cm-diameter low-contrast absorber obtained at 50 Mhz (first column), 140 Mhz (second column) and 350 Mhz (third column) modulation frequencies, respectively. Since co-registered ultrasound images of the low-contrast absorber are essentially the same as the images of high-contrast absorber shown in FIG. 13, these images are not shown in FIG. 14. Table 3 provides the reconstructed average target $\mu_a$ obtained at three modulation frequencies. The 3× data was similar to the 2× data and therefore only the averages are shown in the Table 3. The percentage ratio of the calculated value to the calibrated value of $\mu_a=0.07$ cmP$^{-1P}$ is given in parenthesis. It is clear that the accuracy of reconstructed target absorption maps has been improved in all modulation frequencies. At 50 Mhz, the average reconstructed value over the first five-layers is 136%, 124%, 105%, and 87% for targets located at 2 cm, 2.5 cm, 3 cm and 3.5 cm, respectively. At 140 Mhz, the average reconstructed value over the first five-layers is 101%, 90%, 81%, and 69%, for the corresponding target locations. If the data are averaged over the first four layers, the reconstruction accuracy improves to 113%, 102%, 90%, and 76%, respectively. At 350 Mhz, the target mass only appears at top two to three layers. The average reconstructed value over the first five-layers is 86%, 64%, 60% and 29%, at the corresponding target locations. The average reconstructed value considering the first three-layers is 104%, 86%, 90%, and 41% for the respective depths.

and 350 MHz (fourth column of images) modulation frequencies, respectively. The target was translated in depth in 0.5 cm steps to centers at 1, 1.5, 2, 2.5, 3, and 3.5 cm, respectively. Table 4 provides the reconstructed average absorption coefficients obtained at each layer with the percentage ratio of the calculated to the calibrated $\mu_a = 0.23$ cmP$^{-1P}$ given in parenthesis. The ROI used were twice the target size (2×) and three times the target size (3×). The reconstructed $\mu_a$ has been significantly improved across all target depth and modulation frequencies compared to the corresponding results for the corresponding 3 cm absorber. For 50 MHz probing frequency,

TABLE 3

| Center-Depth Low-Contrast 3-cm absorber | ROI | 50 Mhz 2 x | 3 x | ROI: | 140 Mhz 2 x | 3 x | ROI: | 350 Mhz 2 x | 3 x |
|---|---|---|---|---|---|---|---|---|---|
| 2 cm | #1: | 0.090(129) | | #1: | 0.074(106) | | #1: | 0.073(104) | |
| | #2: | 0.097(139) | | #2: | 0.082(117) | | #2: | 0.103(146) | |
| | #3: | 0.106(151) | | #3: | 0.093(133) | | #3: | 0.044(63) | |
| | #4: | 0.103(146) | | #4: | 0.067(96) | | #4: | 0.049(69) | |
| | #5: | 0.080(114) | | #5: | 0.039(55) | | #5: | 0.033(48) | |
| | #6: | 0.057(81) | | #6: | 0.025(36) | | #6: | 0.017(25) | |
| | Ave: | 0.095(136) | 0.089(127) | Ave: | 0.071(101) | 0.071(101) | Ave: | 0.06(86) | 0.059(85) |
| 2.5 cm | #1: | 0.090(129) | | #1: | 0.077(110) | | #1: | 0.076(108) | |
| | #2: | 0.100(143) | | #2: | 0.089(127) | | #2: | 0.049(70) | |
| | #3: | 0.099(142) | | #3: | 0.072(103) | | #3: | 0.056(80) | |
| | #4: | 0.083(118) | | #4: | 0.046(66) | | #4: | 0.030(43) | |
| | #5: | 0.061(87) | | #5: | 0.032(45) | | #5: | 0.013(18) | |
| | #6: | 0.046(66) | | #6: | 0.025(36) | | #6: | 0.007(10) | |
| | Ave: | 0.087(124) | 0.083(119) | Ave: | 0.063(90) | 0.060(86) | Ave: | 0.045(64) | 0.044(63) |
| 3.0 cm | #1: | 0.087(125) | | #1: | 0.074(106) | | #1: | 0.095(136) | |
| | #2: | 0.091(130) | | #2: | 0.073(104) | | #2: | 0.066(94) | |
| | #3: | 0.080(114) | | #3: | 0.060(86) | | #3: | 0.027(39) | |
| | #4: | 0.062(89) | | #4: | 0.044(63) | | #4: | 0.015(21) | |
| | #5: | 0.048(69) | | #5: | 0.031(44) | | #5: | 0.007(10) | |
| | #6: | 0.040(57) | | #6: | 0.025(36) | | #6: | 0.007(10) | |
| | Ave: | 0.074(105) | 0.070(100) | Ave: | 0.056(81) | 0.054(77) | Ave: | 0.042(60) | 0.041(59) |
| 3.5 cm | #1: | 0.080(114) | | #1: | 0.061(87) | | #1: | 0.047(67) | |
| | #2: | 0.074(106) | | #2: | 0.060(86) | | #2: | 0.030(43) | |
| | #3: | 0.061(87) | | #3: | 0.052(74) | | #3: | 0.009(13) | |
| | #4: | 0.049(70) | | #4: | 0.039(56) | | #4: | 0.007(10) | |
| | #5: | 0.041(59) | | #5: | 0.029(41) | | #5: | 0.007(10) | |
| | Ave: | 0.061(87) | 0.056(80) | Ave: | 0.048(69) | 0.046(66) | Ave: | 0.02(29) | 0.019(27) |

As stated above, when the hybrid probe is compressed against the chest wall in the clinical studies, the inclusions are often located in less than 3 to 4 cm depth. The accuracy of reconstructed absorption maps of the low-contrast absorber is quite high at these depths, especially at 140 Mhz. This indicates that the aforementioned method has the capability to characterize benign lesions accurately. At a higher modulation frequency (e.g. 350 Mhz), the system detection sensitivity is reduced and the penetration of diffusive waves is also reduced.

As for the selection of the ROI or fine-mesh zone, the maximum change of $\mu_a$ is 0.011 cmP$^{-1P}$, which is obtained when the target is located at 2 cm and probed with 50 MHz modulation frequency (target layer #1, data not shown). This maximum change in $\mu_a$ will not cause any benign lesions ($\mu_a < 0.15$ cmP$^{-1P}$) to be misdiagnosed as malignant lesions ($\mu_a > 0.15$ cmP$^{-1P}$). Therefore, the region of interest selection is not critical for reconstruction of large absorbers.

FIG. 15 shows the co-registered ultrasound images (first column of images) and reconstructed optical absorption maps of the 1-cm high-contrast absorber obtained at 50 MHz (second column of images), 140 MHz (third column of images)

the average reconstructed values are 60%, 67%, 72%, 64% 70%, and 53% for 1 cm to 3.5 cm depths, respectively, when the ROI is twice the target size. For 140 MHz, the target is reconstructed as 61%, 71%, 75%, 76% 77%, and 30% for 1 cm to 3.5 cm depths, respectively, with the same ROI. The highest reconstruction accuracy is achieved at 350 MHz and the reconstructed values are 74%, 79% 81% and 54%, for 1 cm to 2.5 cm target depths. No solid target mass was observed in images beyond 2.5 cm depth. The better reconstruction accuracy for 350 MHz for shallow targets suggests that a higher RF modulation frequency could be useful to probe breast lesions near the surface of the skin.

The selection of the ROI for imaging small absorbers has a significant effect on accuracy of reconstructed target absorption coefficients. Table 4 indicates that the average reconstructed value for a 3×ROI was approximately 21% lower than if an ROI of twice the target size was used. Fortunately, with the ultrasound guidance, we have the knowledge about the approximate target size and can select appropriate ROI for dual-mesh based optical imaging reconstruction.

TABLE 4

| High-Contrast | 50 Mhz | | 140 Mhz | | 350 Mhz | |
|---|---|---|---|---|---|---|
| 1-cm absorber | ROI: 2 x | 3 x | ROI: 2 x | 3 x | ROI 2 x | 3 x |
| 1.0 cm | 0.138(60) | 0.134(58) | 0.141(61) | 0.086(37) | 0.171(74) | 0.099(43) |
| 1.5 cm | 0.153(67) | 0.098(43) | 0.163(71) | 0.129(56) | 0.182(79) | 0.129(56) |
| 2.0 cm | 0.166(72) | 0.103(45) | 0.173(75) | 0.111(48) | 0.187(81) | 0.131(57) |
| 2.5 cm | 0.147(64) | 0.096(42) | 0.175(76) | 0.111(48) | 0.124(54) | 0.083(36) |
| 3.0 cm | 0.160(70) | 0.110(48) | 0.177(77) | 0.112(49) | No target | |
| 3.5 cm | 0.123(53) | 0.098(43) | 0.068(30) | 0.062(27) | No target | |

FIG. 16 shows the reconstructed optical absorption maps of the 1-cm low-contrast absorber obtained at 50 MHz (first column), 140 MHz (second column) and 350 MHz (third column) modulation frequencies. The target was translated in depth in 0.5 cm steps and the target center was located at 1, 1.5, 2, 2.5, 3, and 3.5 cm, respectively. Because co-registered ultrasound images of the low-contrast absorber are essentially the same as the images of high-contrast absorber shown in column one of FIG. 15, these images are not shown in FIG. 16. Table 5 provides the reconstructed average absorption coefficients obtained at the target layer with the percentage ratio of the calculated to the calibrated $\mu_a = 0.07$ cmP$^{-1P}$ given in parenthesis. The low contrast small absorber was over-reconstructed by 0.019 cmP$^{-3}$ on average (27%) across the depth at 50 MHz, and by 0.021 cmP$^{-1}$ on average (30%) at 140 MHz. As discussed previously, these small changes will not cause errors in classification of benign and malignant tumors. At 350 MHz, the over-reconstruction is 0.059 cmP$^{-1P}$ (84%) on average. The main reason is the higher noise level of our system at 350 MHz modulation frequency, which is more pronounced when the perturbation is smaller.

tion. Because the cancer has irregular margins in x-y dimensions, the ROI is chosen as the size of the hand-held probe (9 cm×9 cm). FIG. 17(b1, b2), (c1, c2) and (d1, d2) are corresponding reconstructed absorption maps obtained from 50 MHz and 140 MHz at 690 nm, 780 nm and 830 nm, respectively. Similar to the 3-cm high-contrast absorber experiment, the absorption is high at the first three target layers in the 140 MHz images. At the fourth target layer, the absorption mass is barely visible in 690 nm and 830 nm images at 140 MHz. When the 50 MHz was used to probe the lesion, the absorption mass in the fourth target layer is readily seen. Also the light penetration at 830 nm is significantly improved at the 50 Mhz frequency. The total hemoglobin maps and the blood oxygen saturation maps at 50 MHz and 140 MHz are computed and the images are shown in FIG. 17(e1, e2) and (f1, f2), respectively.

Table 6 lists the average absorption coefficients measured within FWHM of each target layer at three wavelengths and two modulation frequencies, as well as computed total hemoglobin concentrations of both maximum and average values.

TABLE 5

| Low-Contrast | 50 Mhz | | 140 Mhz | | 350 Mhz | |
|---|---|---|---|---|---|---|
| 1 cm absorber | ROI: 2 x | 3 x | ROI: 2 x | 3 x | ROI: 2 x | 3 x |
| 1.0 cm | 0.089(127) | 0.059(84) | 0.086(123) | 0.055(79) | 0.114(163) | 0.066(94) |
| 1.5 cm | 0.094(134) | 0.063(90) | 0.099(141) | 0.063(90) | 0.139(199) | 0.081(116) |
| 2.0 cm | 0.092(131) | 0.063(90) | 0.093(133) | 0.061(87) | 0.134(191) | 0.085(120) |
| 2.5 cm | 0.087(124) | 0.065(93) | 0.107(153) | 0.079(113) | No target | |
| 3.0 cm | 0.083(119) | 0.032(46) | 0.069(99) | 0.066(94) | No target | |
| 3.5 cm | No target | | No targte | | No target | |

Figure 17A:
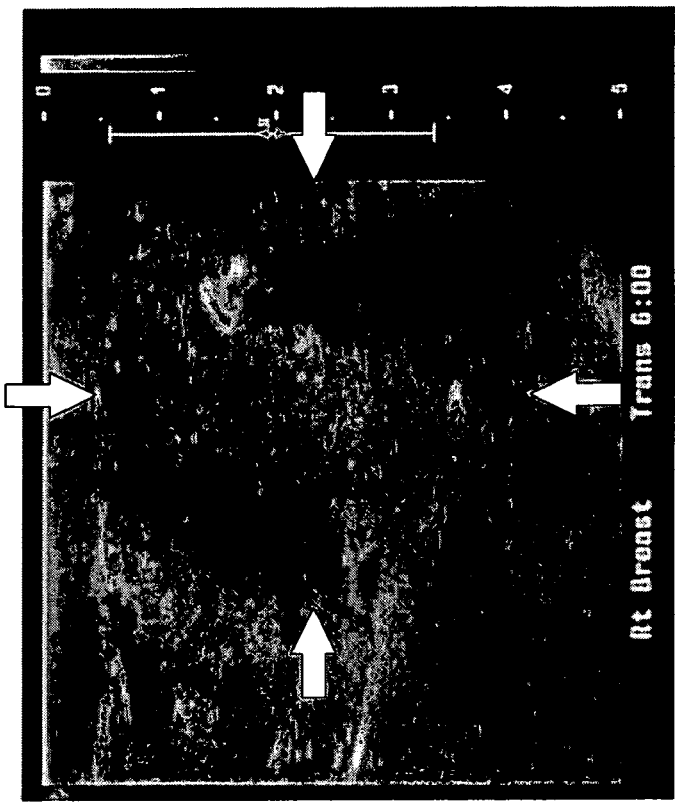
FIG. 17 (a) shows the ultrasound image of the cancer, which is located between 0.5 cm and 3.5 cm in depth.
Figure 16G:
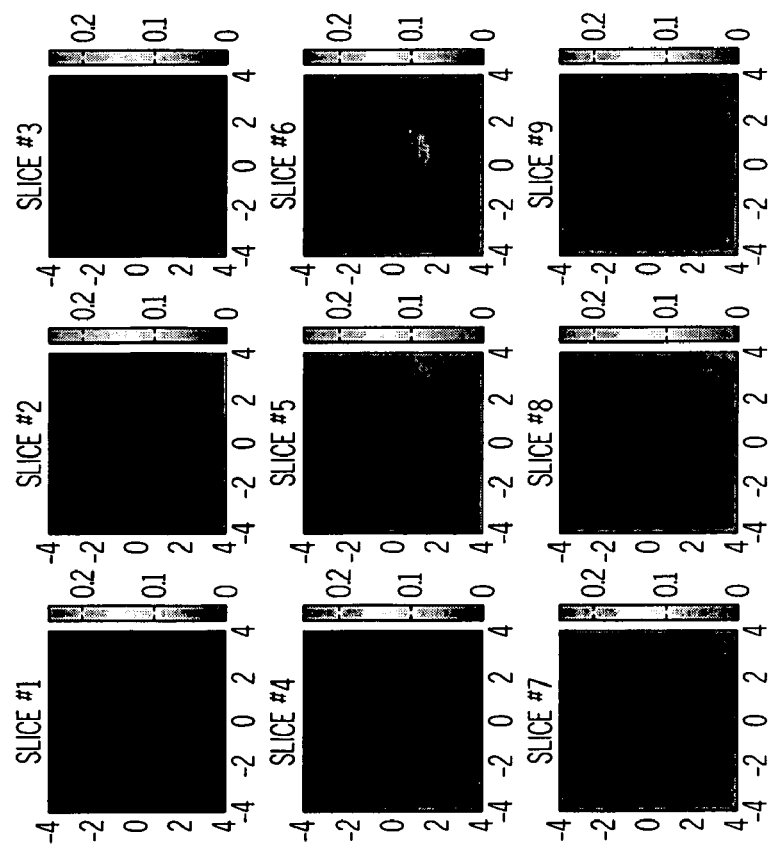

This example was conducted on a 53 year-old woman who had a 3 cm×3 cm×3 cm invasive ductal carcinoma of high grade (III) located at the 6 o'clock position in her right breast. The patient was scheduled for chemotherapy treatment and she was scanned her before the treatment. Two light modulation frequencies of 50 MHz and 140 MHz were used in the scan. FIG. 17(a) shows the ultrasound image of the cancer, which is located between 0.5 cm and 3.5 cm in depth direc- The significant improvement in computed hemoglobin concentration occurs in the fourth layer and about 20 (μ/liter) difference is observed. Furthermore, the estimated oxygen saturation distribution has dramatically improved because of the increased light penetration at 830 nm. As can be seen, the oxygen saturation patterns are similar at both modulation frequencies in slice 4 and 5, and the improvements occur at slice 6 and 7.

TABLE 6

| Lesion-Depth | | 50 Mhz | 140 Mhz | | 50 Mhz | 140 Mhz | | 50 Mhz | 140 Mhz | 50 Mhz   140 Mhz Hemoglobin Con. (μ/liter) Maximum/Ave. |
|---|---|---|---|---|---|---|---|---|---|---|
| | | 690 nm | | | 780 nm | | | 830 nm | | |
| 0.5 to | #1: | 0.152 | 0.156 | #1: | 0.183 | 0.209 | #1: | 0.185 | 0.141 | 125.2/86.9   115.1/80.0 |
| 3.5 cm | #2: | 0.159 | 0.166 | #2: | 0.190 | 0.211 | #2: | 0.193 | 0.143 | 125.9/91.0   112.6/81.3 |
| | #3: | 0.187 | 0.136 | #3: | 0.197 | 0.239 | #3: | 0.203 | 0.170 | 130.3/94.0   129.2/92.1 |
| | #4: | 0.106 | 0.026 | #4: | 0.162 | 0.174 | #4: | 0.173 | 0.094 | 108.7/79.9   82.1/60.7 |
| | #5: | 0.043 | 0.026 | #5: | 0.085 | 0.064 | #5: | 0.106 | 0.014 | 65.2/46.1   49.3/15.3 |
| | #6: | 0.027 | 0.026 | #6: | 0.044 | 0.019 | #6: | 0.073 | 0.014 | 59.6/28.2   47.7/7.7 |

TABLE 6-continued

| Lesion-Depth | 50 Mhz | 140 Mhz | 50 Mhz | 140 Mhz | 50 Mhz | 140 Mhz | 50 Mhz | 140 Mhz |
|---|---|---|---|---|---|---|---|---|
| | 690 nm | | 780 nm | | 830 nm | | Hemoglobin Con. (μ/liter) Maximum/Ave. | |
| Ave4: | 0.122 | 0.121 | 0.183 | 0.208 | 0.188 | 0.137 | 122.6/87.9 | 109.8/78.5 |
| Ave5: | 0.102 | 0.102 | 0.163 | 0.179 | 0.172 | 0.111 | 111.1/79.6 | 597.6/65.9 |

It is interesting to note that the absorption maps as well as the total hemoglobin concentration map reveal heterogeneous tumor vasculature patterns with more microvessels distributed at the tumor periphery. This type of angiogenesis distribution has been in many larger carcinomas. In the literature, the periphery enhancement or rim enhancement of breast lesions in contrast enhanced MR images has been reported. It is therefore concluded that the rim enhancement is due to a combination of angiogenesis, distribution and degree of fibrosis, expression pattern of growth factors, and various histologic features.

Although the higher modulation frequencies can provide improved reconstruction accuracy, their range is limited by the reduced signals detected at greater penetration depths. Many components affect the system performance at higher RF frequencies. In the present system, the minimal bandwidth of preamplifiers, mixers, and RF switches is 500 MHz. The component that limits the frequency response is the photo multiplier tube (PMT (R928)) that has 3 dB bandwidth of 160 MHz. As a result, the average signal decreases by approximately about 60 to about 70% from 140 MHz to 350 MHz in 0.6%-0.7% Intralipid solution at a fixed PMT high voltage gain. In addition, diffusive waves modulated at higher RF frequencies penetrate less deep due to the exponential damping. Both factors affect the sensitivity of the system at the higher end of the RF modulation (e.g. 350 Mhz). In the present system, higher coherent interference noise at 350 MHz further limited the sensitivity and contrast relative to the lower frequencies.

In these phantom studies, the absorbers were immersed in Intralipid™ solution of 0.07% concentration. The fitted background absorption and reduced scattering coefficients were in the range of 0.02 to 0.031 $cmP^{-1}$ and 4.9 to 6.1 $cmP^{-1}$ in different sets of experiments. The fitted bulk absorption and reduced scattering coefficients from normal breasts are within the range of 0.01 to 0.07 $cmP^{-1P}$ and 2 to 13 $cmP^{-1}$. With higher background tissue absorption and scattering, the penetration depth of diffusive waves will be further reduced.

In summary, a new frequency domain optical tomography system utilizing three RF modulation frequencies, which are optimized for probing breast lesions of different size located at different depths was constructed. With the real-time co-registered ultrasound guidance on lesion size and location, an optimal light modulation frequency can be selected which yields more accurate estimates of lesion angiogenesis and hypoxia. Phantom experiments of large and small absorbers of both high and low optical contrasts have demonstrated that a high modulation frequency, such as 350 MHz, is preferable for probing small lesions closer to the surface while a low modulation frequency, such as 50 MHz, is desirable for imaging deeper and larger lesions. A clinical example of a large invasive carcinoma is presented and significant modulation-frequency-dependent and wavelength-dependent tissue penetration of diffusive-waves has been observed.

To evaluate the possible effect of ROI or fine-mesh zone selection on accuracy of the reconstructed absorption coefficients, a reconstructed target using ROIs twice the size of the real target in x-y dimensions and three times the size of the target in x-y dimensions was used. The results have shown that the ROI has negligible effect on reconstructed optical properties of larger 3-cm absorbers. For smaller 1-cm absorbers, the ROI has to be twice the size of the absorber to ensure accurate reconstruction of target optical properties. It was also found that the readily available wavelength pair of 780 nm and 830 nm (weight($\lambda_1$)=0.20 and weight($\lambda_2$)=0.27) is robust for estimation of total hemoglobin concentration.

Example 4

This example was conducted to demonstrate the effects of a partially reflecting boundary method for diffusive optical imaging of shallow targets in turbid media. By reflecting boundary, it is understood that the surface of the probe 4 in contact with tissue is non-black in color. It is desirable for the surface of the probe 4 to be reflecting i.e., white in color.

Before focusing on imaging of shallow targets, the accuracy of using extrapolated boundary condition to approximate partial-current boundary condition for different reflection coefficients has to be addressed. This approximation is essential for simplifying the forward model. The partial-current boundary condition can be expressed formally as $$\phi = l_s \frac{\partial \phi}{\partial z}\bigg|_{z=0}, \text{ where } l_s = \frac{1+R_{eff}}{1-R_{eff}} 2D. \quad (10)$$

where φ is the fluence rate of photons and z is the direction normal to the surface and points to the medium. $R_{eff}$ is defined as the effective reflection coefficient that can be determined experimentally or by Monte Carlo simulation. D is the diffusive coefficient of photons in tissue. According to this boundary condition, distribution of photon density in a semi-infinite homogenous medium generated by a harmonic modulated point source can be described by the following Green's function as shown in equation (11)

$$\phi_{in}^{pc} = \frac{1}{4\pi D}\left(\frac{\exp(-kr_{sd}^{pc})}{r_{sd}^{pc}} + \frac{\exp(-kr_{sid}^{pc})}{r_{sid}^{pc}} - \frac{2}{l_s}\int_0^\infty dl \exp(-l/l_s)\frac{\exp(-kr_{ld})}{r_{ld}}\right), \quad (11)$$

where $\phi_{in}^{pc}$ is the fluence rate of incident wave with the partial-current boundary condition. k is wave vector of photon density wave. $r_{sd}^{pc}$ is the distance between the point source and the detector and $r_{sid}^{pc}$ is the distance between the image of the point source and the detector. Both $r_{sd}^{pc}$ and $r_{sid}^{pc}$ are calculated based on partial-current boundary condition. $r_{ld}$ is the distance between a point on the integral line l and the detector, which is a function of the integral variable l. Equation (11) includes a line integral, which complicates the calculation of scattering field for image reconstruction. Therefore, an approximated boundary condition named extrapolated boundary condition has been widely used in the literature. The corresponding Green's function is written as shown in equation (12):

$$\phi_{in}^{ext} = \frac{1}{4\pi D}\left(\frac{\exp(-kr_{sd}^{ext})}{r_{sd}^{ext}} - \frac{\exp(-kr_{sid}^{ext})}{r_{sid}^{ext}}\right) \quad (12)$$

where $r_{sd}^{ext}$ and $r_{sid}^{ext}$ are similar to those in Equation (11) but calculated from extrapolated boundary condition.

Figure 18B:
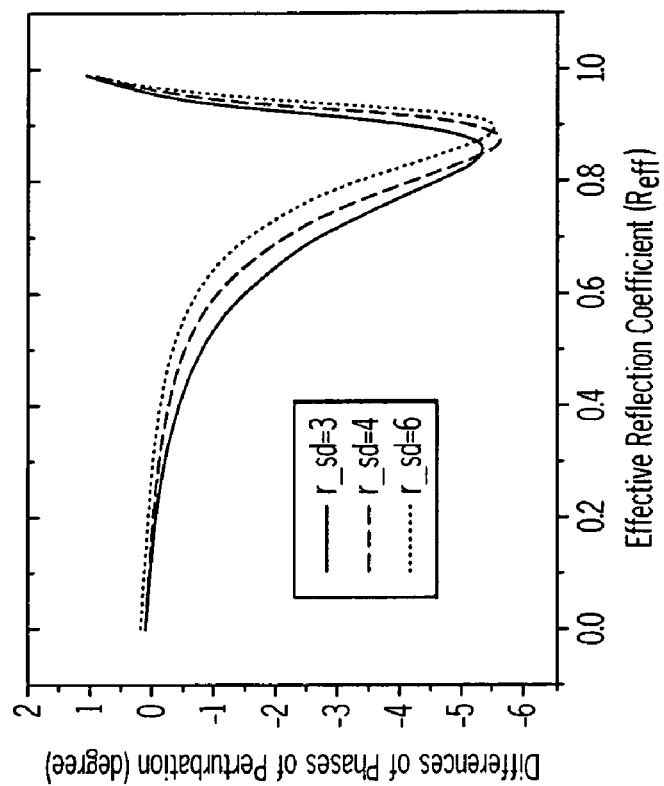
FIG. 18 (a) is a graphical representation showing amplitude versus effective reflection coefficient ($R_{eff}$)
Figure 18A:
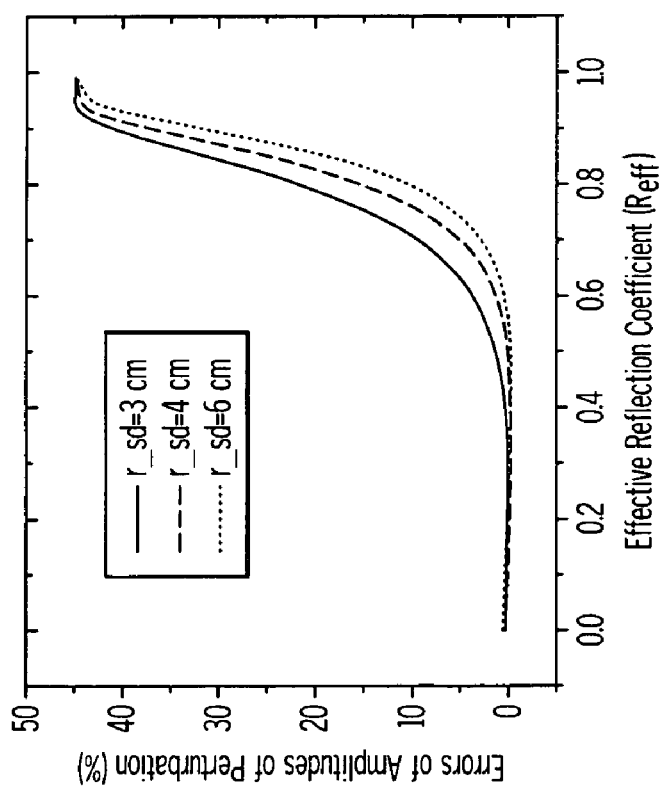

Based on Equations (11) and (12) and the Born approximation, the scattering fields of the photon density wave was calculated for a spherical target from two boundary conditions. The target has a radius of 0.5 cm and is centered at 0.5 cm below the surface. The absorption coefficients of the target and the background are about 0.25 cm$^{-1}$ and 0.03 cm$^{-1}$, respectively. The perturbation is defined as $\phi_{sc}^{pc}/\phi_{in}^{pc}$ for partial-current boundary condition and $\phi_{sc}^{ext}/\phi_{in}^{ext}$ for the extrapolated boundary condition. A relative error of amplitude of the perturbations between two boundary conditions is defined as $E_{am}=(|\phi_{sc}^{pc}/\phi_{in}^{pc}|-|\phi_{sc}^{ext}/\phi_{in}^{ext}|)/(\phi_{sc}^{pc}/\phi_{in}^{pc}|)$. The phase difference of perturbations between the two boundary conditions is defined as $E_{pha}$=phase($\phi_{sc}^{pc}/\phi_{in}^{pc}$)−phase($\phi_{sc}^{ext}/\phi_{in}^{ext}$). Numerical calculations have shown that if Born approximation is assumed, the $E_{am}$ and $E_{pha}$ are independent of the target radius and the absorption coefficient but slightly depend on the target depth. The errors of amplitude and phase of perturbation $E_{am}$ and $E_{pha}$ as a function of effective reflection coefficient $R_{eff}$ are plotted in FIG. 18 (a) and (b), respectively. The results for three typical source-detector separation distances (3 cm, 4 cm and 6 cm) are given in the FIG. 18 (a) and (b). When $0.0<R_{eff}<0.4$, the amplitude error is less than 1% and phase error is less than 0.5 degrees, which are negligible, so that the extrapolated boundary condition can be accurately used to approximate partial-current boundary condition. When $R_{eff}>0.7$, the errors increase very quickly and become remarkable so that the use of extrapolated boundary conditions should be avoided. When $0.4<R_{eff}<0.7$, the maximum errors of amplitude and phase are about 8% and 2.7 degrees, respectively, for $R_{eff}=0.7$ and $r_{sd}=3.0$ cm.

A combined probe was used with an ultrasound transducer centrally located to provide target size, shape, and depth information. A total of 12 emitter fibers and 8 detector fibers are employed in the probe. The distance between emitters and detectors was distributed from about 1 cm to about 7 cm. In general, only the emitter-detector pairs with separation distances from 2.5 cm to 6 cm can be used for imaging. For pairs with distances less than 2.5 cm, the measured signals are saturated; while for pairs larger than 6 cm, the measured signals are too weak and noisy. The entire imaging region is 9×9×3.5 (x, y and z) cm$^3$. The dual-mesh technique discussed above was adopted for imaging reconstruction. The background region was divided into the relatively coarse mesh and each voxel had a size of 1.5×1.5×1.0 cm$^3$. Based on the target localization provided by ultrasound, the target region is limited to a small volume of 2.5×2.5×1 cm$^3$, which is determined by the target size. This inclusion region had finer voxels of 0.25×0.25×0.5 cm$^3$ in size. In these phantom experiments, the radius of the target was fixed to about 0.5 cm and the target was located at the center of x-y plane at an approximate depth of about 0.6 to about 0.7 cm. Therefore the target occupied two layers near the surface. 0.6% Intralipid solution was used to emulate soft tissue. The results obtained at 780 nm and 830 nm. The results obtained at 780 nm are reported below. The calibrated absorption coefficient of the target ranges from 0.2 to 0.3 cm$^{-1}$ and 0.25 cm$^{-1}$ was used as an approximate value. The Born approximation was used to relate the measured perturbation and the medium absorption distribution and a conjugate gradient technique has been used for inverse reconstruction.

The reflecting boundary was obtained by covering the black probe with an aluminum foil, and its effective reflection coefficient can be estimated by fitting the measurement data of homogeneous Intralipid to theoretical data of homogeneous medium obtained from the diffusion equation. It was estimated that $R_{eff} \approx 0.6$ for a regular-aluminum foil. The amplitude errors were about 3.0%, 1.26% and 0.34% for emitter-detector separation distances of 3 cm, 4 cm and 6 cm respectively. Correspondingly, the phase errors are −1.45 degrees, −1.05 degrees and −0.72 degrees respectively.

The reconstructed phantom images are shown in the FIG. 19, in which only the first two target layers are shown. The slice #1 is the spatial x-y image of the top layer, which is 0.5 cm deep in the Intralipid, and the slice #2 is the layer 0.5 cm below slice #1. FIG. 19(a) and (b) are the images reconstructed from an absorbing boundary ($R_{eff} \approx 0$) and a reflection boundary ($R_{eff} \approx 0.6$), respectively. In FIG. 19 (a), the position of the maximum is at (5.0, 5.0) for layer #1 and (5.0, 4.5) for layer #2. The corresponding maximum reconstructed-values are 0.0867 and 0.2967 cm$^{-1}$, which are 34.68% and 118.68% of the expected value (~0.25 cm$^{-1}$). In the FIG. 19(b), the positions of the maxima agree with the position of the true target (4.5, 4.5). The corresponding maxima are 0.212 and 0.194 cm$^{-1}$ for the two layers, respectively, which are 84.80% and 77.60% of the expected value. A striking difference of the reconstructed values between the two layers in the FIG. 19(a) implies that the absorbing boundary is not good in detecting shallow targets less than 0.5 cm deep. However, the reflection boundary provides considerable uniform values in the two layers. Furthermore, in the FIG. 19(a) the mean value obtained by averaging absorption coefficients within −6 dB of the maximum value is 0.073 for layer #1 and 0.236 cm$^{-1}$ for layer #2. The percentages of the mean values relative to the expected value are 29.2% for layer #1 and 94.8% for layer #2, respectively. Correspondingly, in the FIG. 19(b) they are 0.167 cm$^{-1}$ and 0.152 cm$^{-1}$ and the related percentages are 66.8% and 60.8%, respectively. It is obvious that the uniformity of mean values in two layers is improved when the reflecting boundary is used.

This work is useful in clinical applications for breast imaging. Currently, a fixed black probe is used for all patients and the shallow inclusions less than 0.5 to 0.7 cm in depth do not reconstruct correctly in both target location and optical properties. This work provides that a probe having a reflecting surface that is not black can be used for imaging shallow inclusions While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:
1. A method for medical imaging of an inclusion comprising:
  imaging a tissue volume with a probe comprising:
    an ultrasound transducer that is operative to provide an on-site estimation of inclusion size and location;
    a first emitter and a first detector; the first emitter having light of a wavelength of about 400 to about 900 nanom- eters; the first detector detecting light of a wavelength of about 400 to about 900 nanometers;

a source circuit connected in operational communication to the emitter;

a detector circuit connected in operational communication to the detector; and a central processing unit connected to the source circuit and the detector circuit;

scanning the tissue volume with light having a wavelength of about 400 to about 900 nanometers; the tissue volume comprising a first layer and a second layer;

segmenting the scanned tissue volume into an inclusion region comprising a plurality of first voxels and a background region comprising a plurality of second voxels; the volume of each second voxel being larger than the volume of each first voxel;

identifying a tissue layer thickness and an approximate tilting angle between the tissue layer and the probe;

estimating photon density: $\phi(r,\omega)=f(\mu_{a1}, \mu'_{s1}, \mu_{a2}, \mu'_{s2})$, where $\mu_{a1}, \mu_{a2}, \mu'_{s1}$, and $\mu'_{s2}$ are absorption and reduced scattering coefficients of first and second layers, respectively; wherein absorption coefficients have the subscript "a", scattering coefficients have the subscript "s", wherein the subscript "1" represents the first layer, the subscript "2" represents the second layer, and the superscript (') stands for the reduced scattering coefficient;

applying a conjugate gradient method to estimate fitted optical properties of the first layer and the second layer;

minimizing a least-square objective function given as $\min\|\phi(r,\omega)-\phi_0(r,\omega)\|^2$; wherein a forward Jacobian weight matrix $$W_{ij} = \left[\frac{\partial \phi_{ij}}{\partial \mu_{aj}}, \frac{\partial \phi_{ij}}{\partial D_j}\right],$$

that relates the photon density perturbation at detector i and imaging voxel j with absorption coefficient change $\Delta\mu_{aj}$ and diffusion coefficient change $\Delta D_j$, is calculated by using the bulk optical properties simulated from the two-layer layer model and given in equation (1) as:

$$[W_{ij}] = \begin{bmatrix} \frac{\partial \phi_{11}}{\partial \mu_{a1}} & \cdots & \frac{\partial \phi_{1L}}{\partial \mu_{aL}} & \frac{\partial \phi_{11}}{\partial D_1} & \cdots & \frac{\partial \phi_{1L}}{\partial D_L} \\ \frac{\partial \phi_{21}}{\partial \mu_{a1}} & \cdots & \frac{\partial \phi_{2L}}{\partial \mu_{aL}} & \frac{\partial \phi_{21}}{\partial D_1} & \cdots & \frac{\partial \phi_{2L}}{\partial D_L} \\ \vdots & \ddots & \vdots & \vdots & \ddots & \vdots \\ \frac{\partial \phi_{M1}}{\partial \mu_{a1}} & \cdots & \frac{\partial \phi_{ML}}{\partial \mu_{aL}} & \frac{\partial \phi_{M1}}{\partial D_1} & \cdots & \frac{\partial \phi_{ML}}{\partial D_L} \end{bmatrix}, \quad (1)$$

where M is the total number of detector readings; L is the total number of imaging voxels and $\phi_0(r,\omega)$ is the photon density of the first layer.

2. The method of claim 1, further comprising estimating $\phi_0(r,\omega)$, $\mu_{a10}$, $\mu_{a20}$, $\mu'_{s10}$, or $\mu'_{s20}$ by using a solution that has similar values as that of the tissue.

3. The method of claim 1, wherein the inclusion region comprising a first voxel that has a volume of about $0.1\times0.1\times0.1$ cubic centimeter ($cm^3$) to about $1\times1\times1$ $cm^3$; the background region comprising a second voxel that has dimensions of about $0.2\times0.2\times0.2$ $cm^3$ to about $2.0\times2.0\times2.0$ $cm^3$.

4. The method of claim 1, wherein the scanning the tissue volume comprises scanning a cylindrical volume of tissue having a radius large enough to approximate semi-infinite geometry.

5. The method of claim 1, wherein the first layer comprises a breast tissue, while the second layer comprises a chest wall.

6. The method of claim 1, wherein the inclusion comprises a tumor, a lesion, or a cancerous region.

7. The method of claim 1, wherein an interface between the first layer and the second layer is smooth.

8. The method of claim 5, wherein the inclusion and a nearest surface of the chest wall are separated by less than 2 centimeters.

9. The method of claim 1, further comprising scanning the tissue volume with a plurality of lights, each light having a wavelength of about 400 to about 900 nanometers.

10. The method of claim 1, further comprising scanning the tissue volume with light having a wavelength of 690, 780 and 830 nanometers.

11. The method of claim 10, wherein the light having wavelengths of 690, 780 and 830 nanometers is emitted from laser diodes.

12. The method of claim 11, wherein the laser diodes are in operative communication with radio frequency oscillators.

13. The method of claim 12, wherein the radio frequency oscillators operate at frequencies of 350 MHz, 140 MHz and 50 MHz.

14. The method of claim 1, wherein the scanned tissue comprises fluorescence targets or dyes or fluorophores.

* * * * *